(12) United States Patent
Helms et al.

(10) Patent No.: US 12,084,544 B2
(45) Date of Patent: Sep. 10, 2024

(54) DIVERSITY-ORIENTED POLYMERS OF INTRINSIC MICROPOROSITY AND USES THEREOF

(71) Applicant: The Regents of the University of California, Oakland, CA (US)

(72) Inventors: Brett A. Helms, Oakland, CA (US); Swagat Sahu, La Jolla, CA (US); Miranda J. Baran, Onartio (CA); Miles N. Braten, San Francisco, CA (US); Mark E. Carrington, Port of Spain (TT); Stephen M. Meckler, Redwood City, CA (US)

(73) Assignee: The Regents of the University of California, Oakland, CA (US)

( * ) Notice: Subject to any disclaimer, the term of this patent is extended or adjusted under 35 U.S.C. 154(b) by 699 days.

(21) Appl. No.: 17/269,228

(22) PCT Filed: Aug. 16, 2019

(86) PCT No.: PCT/US2019/046886
§ 371 (c)(1),
(2) Date: Feb. 17, 2021

(87) PCT Pub. No.: WO2020/037246
PCT Pub. Date: Feb. 20, 2020

(65) Prior Publication Data
US 2021/0309802 A1    Oct. 7, 2021

Related U.S. Application Data

(60) Provisional application No. 62/719,498, filed on Aug. 17, 2018.

(51) Int. Cl.
*C08G 65/48* (2006.01)
*B01D 67/00* (2006.01)
(Continued)

(52) U.S. Cl.
CPC ....... *C08G 65/48* (2013.01); *B01D 67/00091* (2022.08); *B01D 69/02* (2013.01);
(Continued)

(58) Field of Classification Search
CPC .......................... C08G 65/48; C08G 65/4006; B01D 67/0009; B01D 69/02; B01D 71/52;
(Continued)

(56) References Cited

U.S. PATENT DOCUMENTS

| 4,397,922 A | 8/1983 | Pokhodenko et al. |
| 4,485,154 A | 11/1984 | Remick et al. |

(Continued)

FOREIGN PATENT DOCUMENTS

| CN | 107213807 | 9/2017 |
| CN | 107213807 A | 9/2017 |

(Continued)

OTHER PUBLICATIONS

Ghanem et al., "Polymers of Intrinsic Microporosity Derived from Bis(phenazyl) Monomers," 2008, Macromolecules, 41, 1640-1646. (Year: 2008).*

(Continued)

*Primary Examiner* — Matthew W Van Oudenaren
(74) *Attorney, Agent, or Firm* — Kilpatrick Townsend & Stockton LLP

(57) ABSTRACT

The present disclosure is directed to microporous ladder polymers containing amine-functionalized monomer segments, amidoxime-functionalized monomer segments, or a combination thereof. Monomer compounds for preparation of the polymers are also described, as well as membranes and electrochemical cells containing the polymers.

(Continued)

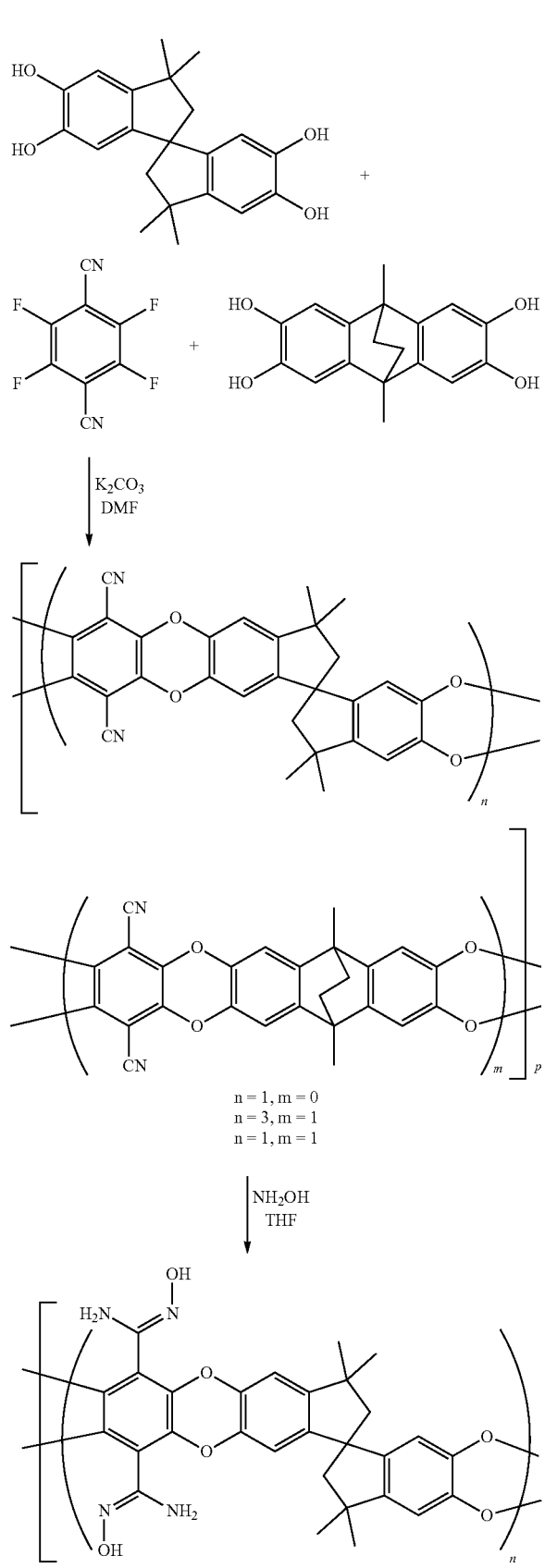

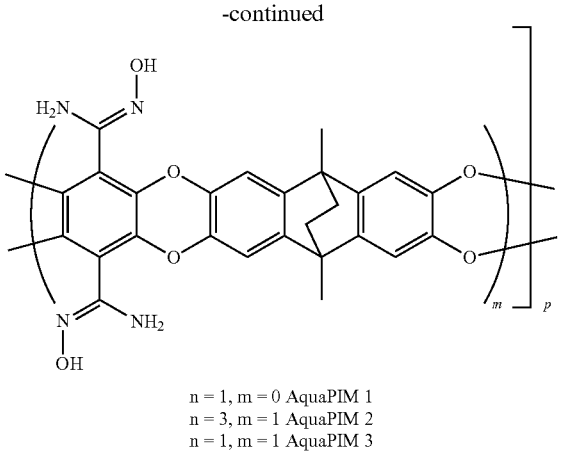

n = 1, m = 0 AquaPIM 1
n = 3, m = 1 AquaPIM 2
n = 1, m = 1 AquaPIM 3

28 Claims, 21 Drawing Sheets

(51) Int. Cl.
    *B01D 69/02*     (2006.01)
    *B01D 71/52*     (2006.01)
    *B01J 39/07*     (2017.01)
    *B01J 39/19*     (2017.01)
    *C07C 215/64*     (2006.01)
    *C07D 211/46*     (2006.01)
    *C07D 295/135*     (2006.01)
    *C07D 295/205*     (2006.01)
    *C08G 65/40*     (2006.01)
    *H01M 10/24*     (2006.01)
    *H01M 50/403*     (2021.01)
    *H01M 50/414*     (2021.01)
    *H01M 50/491*     (2021.01)

(52) U.S. Cl.
    CPC ........... *B01D 71/5211* (2022.08); *B01J 39/07* (2017.01); *B01J 39/19* (2017.01); *C07C 215/64* (2013.01); *C07D 211/46* (2013.01); *C07D 295/135* (2013.01); *C07D 295/205* (2013.01); *C08G 65/4006* (2013.01); *H01M 10/24* (2013.01); *H01M 50/403* (2021.01); *H01M 50/414* (2021.01); *H01M 50/491* (2021.01); *B01D 2325/02831* (2022.08); *H01M 2300/0014* (2013.01)

(58) Field of Classification Search
    CPC .... B01D 71/82; B01D 71/72; B01D 2325/02; B01J 39/07; B01J 39/19; C07C 215/64; C07C 2603/94; C07D 211/46; C07D 295/135; C07D 295/205
    See application file for complete search history.

(56) References Cited

U.S. PATENT DOCUMENTS

| | | |
|---|---|---|
| 4,592,973 A | 6/1986 | Pemsler et al. |
| 5,858,264 A | 1/1999 | Ichino et al. |
| 6,586,138 B2 | 7/2003 | Pekala et al. |
| 7,690,514 B2 | 4/2010 | McKeown et al. |
| 7,758,751 B1 | 7/2010 | Liu et al. |
| 8,056,732 B2 | 11/2011 | McKeown et al. |

(56) References Cited

U.S. PATENT DOCUMENTS

| | | |
|---|---|---|
| 9,481,939 B2 | 11/2016 | Masel et al. |
| 9,580,824 B2 | 2/2017 | Masel et al. |
| 9,815,032 B2 | 11/2017 | Hill et al. |
| 10,710,065 B2 | 7/2020 | Helms et al. |
| 10,862,093 B2 | 12/2020 | Hatta et al. |
| 11,318,455 B2 | 5/2022 | Helms et al. |
| 11,394,082 B2 | 7/2022 | Frischmann et al. |
| 11,545,724 B2 | 1/2023 | Frischmann et al. |
| 2004/0044100 A1 | 3/2004 | Schlenoff et al. |
| 2005/0147891 A1 | 7/2005 | Mikhaylik |
| 2006/0134526 A1 | 6/2006 | Han et al. |
| 2006/0246273 A1 | 11/2006 | McKeown et al. |
| 2007/0264577 A1 | 11/2007 | Katayama et al. |
| 2009/0050199 A1 | 2/2009 | Bartholemew et al. |
| 2009/0136844 A1 | 5/2009 | Watanabe et al. |
| 2009/0155678 A1 | 6/2009 | Less et al. |
| 2010/0003570 A1 | 1/2010 | Finsterwalder et al. |
| 2010/0261065 A1 | 10/2010 | Babinec et al. |
| 2010/0304112 A1 | 12/2010 | Mckeown et al. |
| 2012/0264589 A1 | 10/2012 | Du et al. |
| 2013/0029232 A1 | 1/2013 | Zheng et al. |
| 2014/0212748 A1 | 7/2014 | Zhang et al. |
| 2014/0255636 A1 | 9/2014 | Odeh et al. |
| 2014/0287323 A1 | 9/2014 | Lu et al. |
| 2015/0325828 A1 | 11/2015 | Herle et al. |
| 2016/0118636 A1 | 4/2016 | Jin et al. |
| 2016/0263532 A1 | 9/2016 | Odeh et al. |
| 2016/0285064 A1 | 9/2016 | Hatta et al. |
| 2016/0367948 A1 | 12/2016 | Song et al. |
| 2017/0077503 A1 | 3/2017 | Erickson et al. |
| 2017/0117536 A1 | 4/2017 | Choi et al. |
| 2017/0179532 A1 | 6/2017 | Archer et al. |
| 2017/0346104 A1 | 11/2017 | Helms et al. |
| 2017/0369652 A1 | 12/2017 | Hefner et al. |
| 2018/0065105 A1 | 3/2018 | Song et al. |
| 2018/0085744 A1* | 3/2018 | Helms ..................... B01D 71/82 |
| 2018/0277313 A1 | 9/2018 | Tabuchi et al. |
| 2019/0109310 A1 | 4/2019 | Masel et al. |
| 2019/0245242 A1 | 8/2019 | Tan et al. |
| 2019/0326578 A1 | 10/2019 | Frischmann et al. |
| 2019/0348657 A1 | 11/2019 | Frischmann et al. |
| 2020/0006796 A1 | 1/2020 | Su et al. |
| 2020/0212492 A1 | 7/2020 | Collins et al. |
| 2020/0306745 A1 | 10/2020 | Helms et al. |
| 2020/0328475 A1 | 10/2020 | Hakari et al. |
| 2021/0013536 A1 | 1/2021 | Golden et al. |
| 2023/0131565 A1 | 4/2023 | Frischmann et al. |
| 2023/0216082 A1 | 7/2023 | Ullman et al. |

FOREIGN PATENT DOCUMENTS

| | | | |
|---|---|---|---|
| JP | S62252067 | | 11/1987 |
| KR | 10-2014-0147742 | | 12/2014 |
| WO | 2005/012397 A2 | | 2/2005 |
| WO | 2005113121 | | 12/2005 |
| WO | 2009026467 A1 | | 2/2009 |
| WO | 2012129411 | | 9/2012 |
| WO | 2013005050 | | 1/2013 |
| WO | 2015013478 | | 1/2015 |
| WO | 2015134783 | | 9/2015 |
| WO | WO2016161367 | * | 10/2016 |
| WO | 2017075577 | | 5/2017 |
| WO | 2017117373 | | 7/2017 |
| WO | 2018064365 | | 4/2018 |
| WO | 2018106957 | | 6/2018 |
| WO | 2019/006045 A1 | | 1/2019 |
| WO | 2020006436 | | 1/2020 |
| WO | 2020264386 | | 1/2020 |
| WO | 2021242825 | | 2/2021 |
| WO | 2022235931 A1 | | 11/2022 |
| WO | 2024015957 A1 | | 1/2024 |
| WO | 2024015971 A2 | | 1/2024 |

OTHER PUBLICATIONS

International Search Report in PCT/US2019/056886, mailed Oct. 25, 2019.

Bengston, et al. Membranes of Polymers of Intrinsic Microporosity (PIM-1) Modified by Poly(ethylene glycol). Membranes 2017, 7, 28.

Budd, et al. (2008) Gaspermeation parameters and other physiochemical properties of a polymer of intrinsic microporosity: Polybenzodioxane PIM-1. J. Membr. Sci. 325, 851-860.

Doris, et al. (2016) Understanding and controlling the chemical evolution and polysulfide-blocking ability of lithium-sulfur battery membranes cast from polymers of intrinsic microporosity. J. Mat. Chem. A 4, 16946-16952.

Emmler, et al. (2010) Free Volume Investigation of Polymers of Intrinsic Microporosity (PIMs): PIM-1 and PIM1 Copolymers Incorporating Ethanoanthracene Units. Macromolecules 43, 6075-6084.

Gross, et al. (2018) Rechargeable Zinc-Aqueous Polysulfide Battery with a Mediator-Ion Solid Electrolyte. ACS Appl. Mater. Interfaces 10, 10612-10617.

Li, et al. (2015) Polysulfide-Blocking Microporous Polymer Membrane Tailored for Hybrid Li-Sulfur Flow Batteries. Nano Lett. 15, 5724-5729.

Li, et al. (2018) Engineered Transport in Microporous Materials and Membranes for Clean Energy Technologies. Adv. Mater. 30, 1704953.

Mckeown, et al. (2006) Polymers of intrinsic microporosity (PIMs): organic materials for membrane separations, heterogeneous catalysis and hydrogen storage. Chem. Soc. Rev. 35, 675-683.

Mckeown, et al. (2010) Exploitation of Intrinsic Microporosity in Polymer-Based Materials. Macromolecules 43, 5163-5176.

Mckeown, et al. (2012) Polymers of Intrinsic Microporosity. ISRN Materials Science. vol. 2012, Article ID 513986, 16 pages.

Patel et al., Noninvasive functionalization of polymers of intrinsic microporosity for enhanced CO2 capture. Chem. Commun., 2012, 48, 9989-9991.

Rose e tal. (2017) Polymer ultrapermeability from the inefficient packing of 2D chains. Nature Materials 16, 932-937.

Ward, et al. (2017) Materials Genomics Screens for Adaptive Ion Transport Behavior by Redox-Switchable Microporous Polymer Membranes in Lithium-Sulfur Batteries. ACS Cent. Sci. 3, 399-406.

Winsberg et al., (2017) Aqueous 2,2,6,6-Tetramethylpiperidine-N-oxyl Catholytes for a High-Capacity and High Current Density Oxygen-Insensitive Hybrid-Flow Battery. ACS Energy Lett. 2, 411-416.

Yin et al., (2018) First Clear-Cut Experimental Evidence of a Glass Transition in a Polymer with Intrinsic Microporosity:PIM-1. J. Phys. Chem. Lett. 9, 2003-2008.

Yuan et al. (2018) Toward a Low-Cost Alkaline Zinc-Iron Flow Battery with a Polybenzimidazole Custom Membrane for Stationary Energy Storage. iScience 3, 40-49.

Yuan et al. (2018) Ion conducting membranes for aqueous flow battery systems. Chem Commun. 54, 7570-7588.

Zhang et al., (2015) Synthesis of perfectly alternating copolymers for polymers of intrinsic microporosity. Polym. Chem. 6, 5003-5008.

Zhang et al., Charged porous polymers using a solid CO cross-coupling reaction. Chemistry—A European Journal. Jul. 15, 2015;21 (37).

Aetukuri et al., "Flexible Ion-Conducting Composite Membranes for Lithium Batteries," Advanced Energy Materials, 5(14), p. 1500265 (2015).

Ahn et al., "Gas transport behavior of mixed-matrix membranes composed of silica nanoparticles in a polymer of intrinsic microporosity (PIM-1)," Journal of Membrane Science, 346(2), pp. 280-287 (2010).

Bisoi et al., "Gas separation properties of Troeger's base-bridged polyamides", e-Polymers 2017, 17(4), 283-293.

Carta, et al., "The synthesis of microporous polymers using Troger's base formation", Polymer Chemistry 2014, 5, 5267-5272.

Carta, et al., Novel spirobisindanes for use as precursors to polymers of intrinsic microporosity, Organic Letters, Mar. 15, 2008, pp. 2641-2643, vol. 10, No. 13.

Du, Naiying, et al. "Azide-Based Cross-Linking of Polymers of Intrinsic Microporosity (PI Ms) for Condensable Gas Separation."

(56) References Cited

OTHER PUBLICATIONS

Macromolecular Rapid Communications, vol. 32, No. 8, 2011, pp. 631-636., doi: 10.1002/marc.201000775 (Year: 2011).

Hart, K. E., & Colina, C. M. (2014). Ionomers of Intrinsic Microporosity: In Silica Development of Ionic-Functionalized Gas-Separation Membranes. Langmuir, 30(40), 12039-12048. doi: dx.doi .org/10.1021/la5027202 (Year: 2014).

Li et al., "Air-breathing aqueous sulfur flow battery for ultralowcost long-duration electrical storage", Joule, 1(2), 306-327, Oct. 11, 2017, 2017 Published by Elsevier Inc., (2017).

Li, et al., "A Polysulfide-Blocking Microporous Polymer Membrane Tailored for Hybrid Li-Sulfur Flow Batteries," ACS Nano Letters 2015, Supporting Information, 11 pages.

Li, et al., Polysulfide-blocking microporous polymer membrane tailored for hybrid Li-Sulfur flow batteries, Nano Letters, Aug. 3, 2015, pp. 5724-5729, vol. 15, No. 9.

Madrid, et al., "Metastable Ionic Diodes Derived from an Amine-Based Polymer of Intrinsic Microporosity," Angew. Chem. Int. Ed. 2014, 53, pp. 10751-10754.

McKeown et al., "Polymers of Intrinsic Microporosity (PIMS): Bridging the void between Microporous and Polymeric Materials", Chem. Eur. J. 2005, 11(9), 2610-2620.

Wei et al., "An aqueous redox flow battery based on neutral alkali metal ferri/ferrocyanide and polysulfide electrolytes", Journal of The Electrochemical Society 2015, 163(1), A5150-A5153.

Extended European Search Report mailed Jun. 30, 2020 for European Patent Application No. 17878273.6 (9 pages).

Extended European Search Report mailed Mar. 27, 2020 for European Patent Application No. 17857439.8 (9 pages).

International Search Report and Written Opinion for International Patent Application No. PCT/US2016/025712, mailed Oct. 6, 2016, 10 pages.

International Search Report and Written Opinion for International Patent Application No. PCT/US2017/054069, mailed Dec. 15, 2017 (10 pages).

International Search Report and Written Opinion for International Patent Application No. PCT/US2017/065174, mailed Mar. 7, 2018, 7 pages.

International Search Report and Written Opinion for International Patent Application No. PCT/US2020/039867, mailed Nov. 15, 2019, 17 pages.

International Search Report and Written Opinion for International Patent Application No. PCT/US2020/039942, mailed Oct. 22, 2020, 15 pages.

International Search Report and Written Opinion for International Patent Application No. PCT/US2021/034203, mailed Aug. 25, 2021, 9 pages.

Extended European Search Report, EP Application No. 19850375.7, dated Jan. 27, 2022, 5 pages.

Baran, et al., "Design Rules for Membranes from Polymers of Intrinsic Microporosity for Crossover-free Aqueous Electrochemical Devices," 2019, Joule 3, pp. 2968-2985.

Bengston, et al., "Membranes of Polymers of Intrinsic Microporosity (PIM-1) Modified by Poly(ethylene glycol)," 2017, Membranes 2017, 7, 28.

Budd, et al., "Gas permeation parameters and other physiochemical properties of a polymer of intrinsic microporosity: Polybenzodioxane PIM-1," 2008, Journal of Membrane Science 325, pp. 851-860.

Doris, et al., "Understanding and controlling the chemical evolution and polysulfide-blocking ability of lithium-sulfur battery membranes cast from polymers of intrinsic microporosity," 2016, J. Mat. Chem. A4, 16946-16952.

Emmler, et al., "Free Volume Investigation of Polymers of Intrinsic Microporosity (PIMs): PIM-1 and PIM1 Copolymers Incorporating Ethanoanthracene Units," 2010. Macromolecules 43, 6075-6084.

Gross, et al., "Rechargeable Zinc-Agueous Polysulfide Battery with a Mediator-Ion Solid Electrolyte," 2018, ACS Appl. Mater. Interfaces 10, 10612-10617.

Li, et al., "Polysulfide-Blocking Microporous Polymer Membrane Tailored for Hybrid Li-Sulfur Flow Batteries," 2015, Nano Letters 15, 5724-5729.

Li, et al. (2018) Engineered Transport in Microporous Material sand Membranes for Clean Energy Technologies, 2018, Adv. Mater. 30, 1704953.

Mckeown, et al., "Polymers of intrinsic microporosity (PIMs): organic materials for membrane separations, heterogeneous catalysis and hydrogen storage," 2006 Chem. Soc. Rev. 35, 675-683.

Mckeown, et al., "Exploitation of Intrinsic Microporosity in Polymer-Based Materials," 2010, Macromolecules 43, 5163-5176.

McKeown, "Polymers of Intrinsic Microporosity," 2012, International Scholarly Research Network, vol. 2012, Article ID 513986, 16 pages.

Rose et al., "Polymer ultrapermeability from the inefficient packing of 2D chains," 2017, Nature Materials 16, 932-937.

Winsberg et al., "Agueous 2,2,6,6-Tetramethylpiperidine-N-oxyl Catholytes for a High-Capacity and High Current Density Oxygen-Insensitive Hybrid-Flow Battery," 2017, ACS Energy Letters, 2, 411-416.

Ward, et al., "Materials Genomics Screens for Adaptive Ion Transport Behavior by Redox-Switchable Microporous Polymer Membranes in Lithium-Sulfur Batteries," 2017, ACS Cent. Sci. 3, 399-406.

Yin et al., "First Clear-Cut Experimental Evidence of a Glass Transition in a Polymer with Intrinsic Microporosity:PIM-1," 2018, J. Phys. Chem. Lett. 9, 2003-2008.

Yuan et al., "Ion conducting membranes for aqueous flow battery systems," 2018, Chem. Commun. 54,7570-7588.

Yuan et al., "Toward a Low-Cost Alkaline Zinc-Iron Flow Battery with a Polybenzimidazole Custom Membrane for Stationary Energy Storage," 2018, iScience 3, 40-49.

Zhang et al., "Charged Porous Polymers using a Solid C—O Cross-Coupling Reaction," 2015, Chemistry: A European Journal, vol. 21, Issue 37, 5 pages.

Zhang et al., "Synthesis of perfectly alternating copolymers for polymers of intrinsic microporosity," 2015, Polym. Chem.6, 5003-5008.

International Search Report and Written Opinion for International Patent Application No. PCT/US2019/046886, mailed Oct. 25, 2019, 7 pages.

International Search Report and Written Opinion for International Patent Application No. PCT/US2022/027867, mailed on Oct. 6, 2022, 24 pages.

International Search Report and Written Opinion for International Patent Application No. PCT/US2023/70200, mailed on Dec. 13, 2023, 9 pages.

International Search Report and Written Opinion for International Patent Application No. PCT/US2023/70227, mailed on Jan. 24, 2024, 10 pages.

Khan et al. (2013) "Cross-Linking of Polymer of Intrinsic Microporosity (PIM-1) via nitrene reaction and its effect on gas transport property", European Polymer Journal, 49:4157-4166.

Lonchakova et al. (2019) "Efficient Gel-polymer Electrolyte for Sodium-ion Batteries Based on Poly(Acrylonitrile-co-methyl Acrylate)", Electrochimica Acta, 334:135512 (10 pages).

* cited by examiner

DIVERSITY-ORIENTED POLYMERS OF INTRINSIC MICROPOROSITY AND USES THEREOF

CROSS-REFERENCES TO RELATED APPLICATIONS

The present application claims priority to U.S. Provisional Pat. Appl. No. 62/719,498, filed on Aug. 17, 2018, which application is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in the invention.

BACKGROUND OF THE INVENTION

Polymer membranes can be manufactured from microporous polymers, whose glass transition temperatures are typically above their decomposition temperatures, provided they are substantially soluble in casting solvents. Such membranes, which feature pore sizes predominantly in the range of 0.5-2 nm, are useful for gas separations, pervaporation, electrowinning, fuel cells, batteries, (photo)electrochemical cells, etc. (Li et al. *Adv. Mater.* 30, 1704953 (2018).)

BRIEF SUMMARY OF THE INVENTION

Provided herein are microporous polymer according to the formula $-[A-AB-B]_n$-described below. In certain embodiments, the microporous polymers contain amine-functionalized monomer segments, amidoxime-functionalized monomer segments, or a combination thereof.

Also provided herein are monomers that can be used for preparing the compounds. In some embodiments, the monomers are compounds according to Formula (I), (II), (III), (IV), (V), (VI), (VII), or (VIII):

(I)
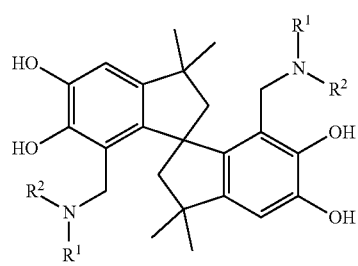

(II)
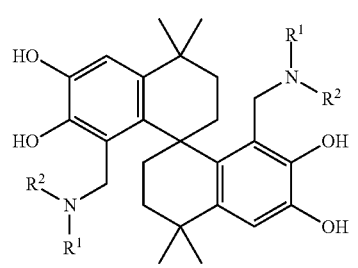

-continued (III)
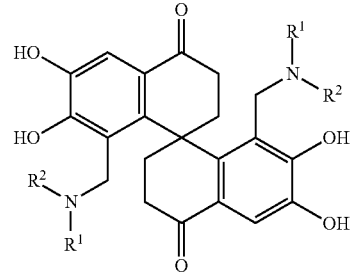

(IV)
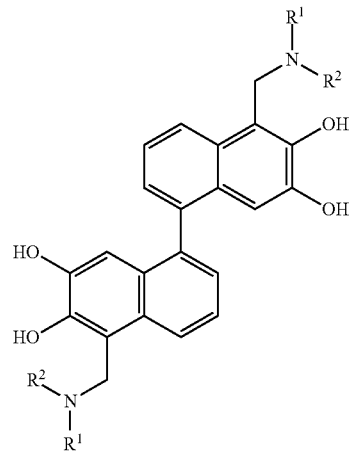

(V)
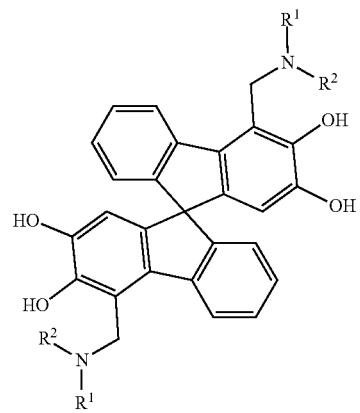

(VI)
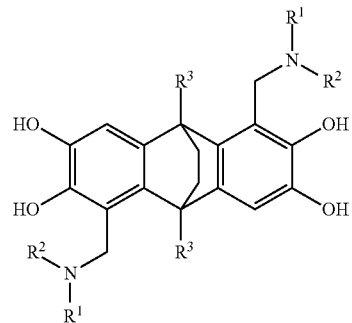

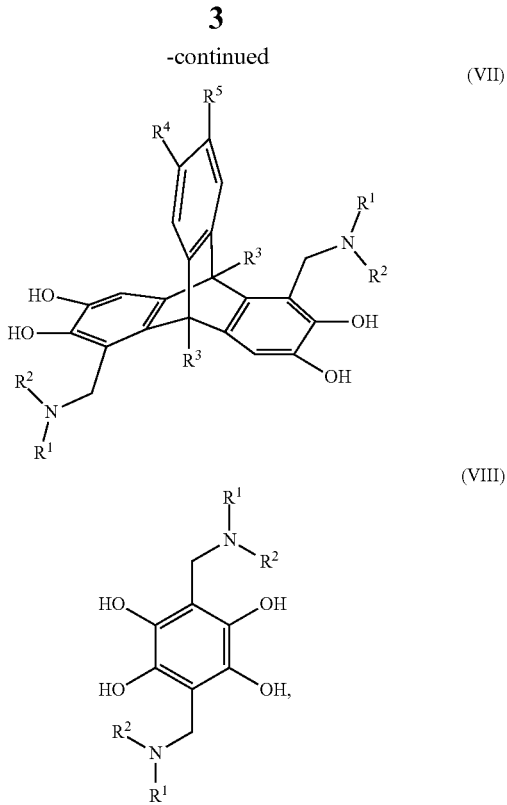

(VII)

(VIII)

and salts thereof, wherein $R^1$-$R^5$ are defined as described below.

Also provided herein are membranes and electrochemical cells containing the microporous polymers of the disclosure.

DETAILED DESCRIPTION OF THE INVENTION

Figure 1:
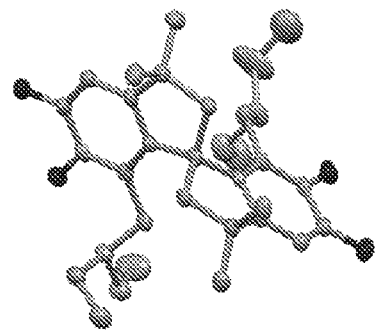
FIG. 1 shows the X-ray crystallography structure of amine-functionalized monomer 3.

The present invention relates to the synthesis and composition of microporous polymers, which feature site specific amino methylated side chains in combination with 1,4-dicyanoarenes and derivatives thereof along the polymer chain. These combinations allow for the tailoring microporous polymer architectures to affect their transport properties for diverse applications, such as gas separations, pervaporation, electrowinning, fuel cells, batteries, (photo)electrochemical cells, etc. The introduction of kinks into what are otherwise highly rigid backbones (e.g., ladder-type polymer backbones) frustrates chain packing in the solid state giving rise to high fractional free volume. The studies detailed herein demonstrate that these modifications are amenable to variety of substrates with functional groups that can be utilized in conjunction with different transport processes.

Aqueous electrochemical devices requiring highly conductive, ion-selective cation exchange membranes see impressive gains when configured with membranes containing the polymers of the present disclosure, which utilize exceptionally rigid microporous architectures and high-pH stable, ionizable amidoxime pore functionality to enforce transport selectivity. Within this architectural framework, membrane processing and performance can be controlled at the molecular level by varying structure of the monomer's contortion site, whether in 2D or 3D. With this control, a specific membrane architecture was identified from which a variety of Zn-based electrochemical cells, including aqueous Zn-TEMPO-sulfate and Zn—$K_4Fe(CN)_6$ cells, were remarkably stable. The studies described herein led to the identification of a threshold value for transport selectivity met by such membranes in order for crossover-free operation to materialize. This transport selectivity can be leveraged to provide extended cycle-life and higher round-trip energy efficiency.

Details of one or more embodiments of the subject matter described in this specification are set forth in the accompanying drawings and the description below. Other features, aspects, and advantages will become apparent from the description, the drawings, and the claims. Note that the relative dimensions of the figures may not be drawn to scale.

I. Definitions

As used herein, the term "polymer" refers to a molecule composed of repeating structural units, referred to herein as monomers or repeat units, connected by covalent chemical bonds. Polymers are generally characterized by a high molecular weight, such as a molecular weight greater than 100 atomic mass units (amu), greater than 500 amu, greater than 1000 amu, greater than 10000 amu or greater than 100000 amu. In some embodiments, a polymer may be characterized by a molecular weight provided in g/mol or kg/mol, such as a molecular weight of about 200 kg/mol or about 80 kg/mol. The term polymer includes homopolymers, or polymers consisting essentially of a single repeating monomer subunit. The term polymer also includes copolymers, which are formed when two or more different types of monomers are linked in the same polymer. Copolymers may comprise two or more monomer subunits, and may include random, block, alternating, segmented, grafted, tapered and other copolymers. Useful polymers include organic polymers that may be in amorphous, semi-amorphous, crystalline or partially crystalline states. Crosslinked polymers having monomer units that are linked to other polymer molecules or other parts of the same polymer molecule are useful for some applications.

As used herein, the term "repeat unit" refers to a part of a polymer that represents a repetitive structure of the polymer chain, the repetition of which would make up the complete polymer chain with the exception of end groups corresponding to terminal ends of the polymer chain. A repeat unit may also be referred to herein as a monomer. Repeat units may be identified in a polymer structure by brackets or parentheses and include a subscript n, which represents the degree of polymerization. In some embodiments, values for subscript n include integers selected from, for example, 10 to 1000, 50 to 900, 100 to 800, or 200 to 500. In some embodiments, subscript n is an integer more than 1000. It will be appreciated that a value for subscript n in a polymer may not be explicitly provided, consistent with use by skilled artisans in the field of polymer chemistry.

As used herein, the term "microporosity" refers to a characteristic of a material describing the inclusion of voids, channels, openings, recessed regions, etc., also referred to herein as micropores, in the body of material. In some embodiments, the micropores have a cross sectional dimension of about 2 nm or less. Micropores may have, for example, a cross sectional dimension of about 1.7 nm or less, 1.5 nm or less, 1.2 nm or less, 1 nm or less, or 0.8 nm or less. Optionally, micropores may have cross sectional dimensions selected from the range of 0.5 nm to 2 nm, selected from the range of 0.5 nm to 1.2 nm, or selected from the range of 1.2 nm to 1.7 nm. The inclusion of micropores in a material may allow for other materials, such as gases, liquids, ions, etc., to pass through the micropores.

As used herein, the term "intrinsic microporosity" refers to a continuous network of interconnected voids in a material formed as a direct consequence of the shape and rigidity of the components of the material. Intrinsic microporosity is achieved in some polymers by the polymers possessing individual structural units that are rigid and that may be oriented relative to one another in such a way that the structural units align to form an opening or pore. Additionally or alternatively, a polymer possessing intrinsic microporosity may have a structure that exhibits frustrated packing. Frustrated packing of a polymer may occur when a polymer molecule contacts itself or other like polymer molecules and the rigidity of the molecule(s) causes the molecule(s) to lie in a configuration where spaces between the molecule(s) are created. Such spaces may correspond to micropores in a film or membrane made of the polymer molecules, for example.

As used herein, the term "polymer of intrinsic microporosity" refers to a polymer that exhibits microporosity due to the shape and rigidity of the molecular structure of the repeat units within the polymer, where the repeat units may align relative to one another such that spaces or openings are generated along the polymer chain. Additionally or alternatively, the repeat units may align in an aggregate of the polymer in a way that frustrates packing of the polymer molecules in the aggregate such that spaces or openings are generated between different polymer molecules and/or between segments of the same polymer molecule. These spaces within the aggregated polymer may, at least in part, provide the microporosity to such a polymer. Due to the inclusion of the micropores, some polymers of intrinsic microporosity may exhibit high surface areas, such as a surface area selected from the range of 300 $m^2$ $g^{-1}$ to 1500 $m^2$ $g^{-1}$. Example polymers of intrinsic microporosity include, but are not limited to, those described in US 2017/0346104, US 2018/0085744, U.S. Pat. Nos. 7,690,514, 8,056,732, WO 2005/012397, and WO 2005/113121, each of which is incorporated herein by reference, as well as those described by McKeown (*ISRN Materials Science*, Volume 2012, Article ID 513986), which is incorporated herein by reference.

As used herein, the term "crosslink" refers to a process by which covalent bonds are formed between separate polymer molecules or between separate monomer sites on the same polymer molecule. A "crosslink" may also refer to a covalent bond formed between separate polymer molecules or between separate monomer sites on the same polymer molecule. A crosslink may also refer to a chemical species of one or more atoms that forms covalent bonds with separate polymer molecules or between separate monomer sites on the same polymer molecule.

As used herein, the term "crosslinking agent" refers to a composition used to facilitate forming crosslinks between separate polymer molecules or between separate monomer sites on the same polymer molecule. Some crosslinking agents may, for example, be a catalyst that is not covalently incorporated into the polymer molecule but merely increases a crosslinking rate and/or lowers an energy requirement for a crosslinking reaction. Some crosslinking agents may be directly incorporated, at least in part, within a covalent link between polymer molecules or between separate monomer sites on the same polymer molecule. Example crosslinking agents include, but are not limited to, 2,6-bis(4-azido-benzyl-idene)cyclohexanone, 2,6-bis(4-azidobenzylidene)-4-methylcyclohexanone, 2,6-bis(4-azidobenzylidene)-4-ethylcyclohexanone, and 4-azidophenylsulfone. In some embodiments, oxygen may serve as a crosslinking agent.

As used herein, the term "electrochemical cell" refers to a device that produces electrical energy through chemical reactions. Example electrochemical cells include batteries and fuel cells. Batteries may include solid-state batteries, semi-solid batteries, wet cell batteries, dry cell batteries, flow batteries, solar flow batteries, primary batteries, secondary batteries, etc. A battery may refer to an assembly of a plurality of individual electrochemical cells, such as arranged in a series configuration. Example electrochemical cells include an anode, a cathode, a separator between the anode and the cathode, and an electrolyte. Electrochemical cells may further include a current collector in electrical contact with an electrode and/or an electrolyte and may be used, in part, to provide a conductive path between the electrode and a load.

As used herein, the term "anode" refers to an electrode in an electrochemical cell where oxidation occurs during discharge of the electrochemical cell. In some embodiments, an anode is identified in an electrochemical cell as the negative electrode, where electrons are emitted during discharge for use by a load. In some embodiments, an anode oxidizes material and releases positive ions to an electrolyte during discharge.

As used herein, the term "cathode" refers to an electrode in an electrochemical cell where reduction occurs during discharge of the electrochemical cell. In some embodiments, a cathode is identified in an electrochemical cell as the positive electrode, where electrons are received during discharge after use by a load. In some embodiments, a cathode reduces positive ions received from an electrolyte during discharge.

As used herein, the term "separator" refers to an ion conductive barrier used to separate an anode and a cathode in an electrochemical cell. In some embodiments, a separator is a porous or semi-permeable membrane that restricts the passage of certain materials across the membrane. In some embodiments, a separator provides a physical spacing between the anode and the cathode in an electrochemical cell. In some embodiments, a separator is not electrically conductive and provides a gap in electrical conductivity between the anode and the cathode in an electrochemical cell.

As used herein, the term "electrolyte" refers to an ionically conductive substance or composition and may include solvents, ionic liquids, metal salts, ions such as metal ions or inorganic ions, polymers, ceramics, and other components. An electrolyte may be a solid, in some embodiments. An electrolyte may be a liquid, such as a solvent containing dissolved ionic species. An electrolyte may be used, in some embodiments, for transporting ions between an anode and a cathode in an electrochemical cell.

As used herein, the term "ionic solution" refers to a solvent including dissolved ionic species. An electrolyte is an example of an ionic solution. Useful solvents for ionic solutions include aqueous solvents containing water. Useful solvents for ionic solutions include non-aqueous solvents, such as organic solvents.

As used herein, the term "anode electrolyte" refers to an electrolyte in an electrochemical cell in contact with an anode. An anode electrolyte may also be referred to herein as an "anolyte." An anode electrolyte may further be in contact with a separator in an electrochemical cell.

As used herein, the term "cathode electrolyte" refers to an electrolyte in an electrochemical cell in contact with a cathode. A cathode electrolyte may also be referred to herein as a "catholyte." A cathode electrolyte may further be in contact with a separator in an electrochemical cell.

As used herein, the term "membrane" refers to a web of material that extends in lateral dimensions, which may be orthogonal to a thickness dimension of the membrane. In some embodiments, the term "membrane" may be used interchangeably herein with the term "film" or "interlayer." Optionally, a membrane separates two regions in space by the physical materials that make up the membrane. A membrane may be used as a support or template for other materials in order to provide structure and/or stability to the other material, for example. The other material may be attached to one side of the membrane, and or may encapsulate all or portions of the membrane.

As used herein, the term "support membrane" refers to a structural film that may provide mechanical stability to another material coated onto or otherwise attached to the film. In some embodiments, a support membrane may be porous or otherwise allow materials, such as ions, gases, or liquids, to pass through the support membrane, though any coated or otherwise supported material may restrict, at least in part, the passage of the ions, gases, or liquids.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. For example, "substituted alkyl" groups can be substituted with one or more groups selected from halo, hydroxy, amino, alkylamino, amido, acyl, nitro, cyano, and alkoxy.

As used herein, the term "alkenyl" refers to an alkyl group, as defined herein, having one or more carbon-carbon double bonds.

As used herein, the term "alkynyl" refers to an alkyl group, as defined herein, having one or more carbon-carbon triple bonds.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane. [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. For example, "substituted cycloalkyl" groups can be substituted with one or more groups selected from halo, hydroxy, amino, alkylamino, amido, acyl, nitro, cyano, and alkoxy.

As used herein, the term "heteroalkyl," by itself or as part of another substituent, refers to an alkyl group of any suitable length and having heteroatoms (e.g., 1-3 heteroatoms) such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio, or amino group. Alternatively, the heteroatom portion can be the connecting atom, or be inserted between two carbon atoms.

As used herein, the term "chalcogenide" refers to an atom selected from oxygen, sulfur, selenium, tellurium, and polonium. In certain embodiments, monomers and polymers of the present disclosure contain chalcogenides selected from oxygen and sulfur.

As used herein, the term "pnictide" refers to an atom selected from nitrogen, phosphorus, arsenic, antimony, and bismuth. In certain embodiments, monomers and polymers of the present disclosure contain pnictides selected from nitrogen and phosphorus.

As used herein, the terms "halo" and "halogen," by themselves or as part of another substituent, refer to a fluorine, chlorine, bromine, or iodine atom.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. For example, "substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as C$_{5-6}$, C$_{3-8}$, C$_{4-8}$, C$_{5-8}$, C$_{6-8}$, C$_{3-9}$, C$_{3-10}$, C$_{3-11}$, or C$_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be C$_{5-8}$ heteroaryl, wherein 1 to 4 carbon ring atoms are replaced with heteroatoms; or C$_{5-8}$ heteroaryl, wherein 1 to 3 carbon ring atoms are replaced with heteroatoms; or C$_{5-6}$ heteroaryl, wherein 1 to 4 carbon ring atoms are replaced with heteroatoms; or C$_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. For example, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, C$_{3-6}$, C$_{4-6}$, C$_{5-6}$, C$_{3-8}$, C$_{4-8}$, C$_{5-8}$, C$_{6-8}$, C$_{3-9}$, C$_{3-10}$, C$_{3-11}$, or C$_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. For example, "substituted heterocyclyl" groups can be substituted with one or more groups selected from halo, hydroxy, amino, oxo, alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "amino" refers to a moiety —$NR_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —$SO_2R$, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or alkyl.

As used herein, the term "acyl" refers to a moiety —C(O)R, wherein R is alkyl.

As used herein, the term "nitro" refers to the moiety —$NO_2$.

As used herein, the term "oxo" refers to an oxygen atom that is double-bonded to a compound (i.e., O=).

The term "salt," in reference to a monomer or polymer as described herein, refers to an acid salt or base salt of the monomer or polymer. A monomer or polymer may have one or more salt moieties. Illustrative examples of salts are mineral acid salts (e.g. salts formed with hydrochloric acid, hydrobromic acid, phosphoric acid, or the like), organic acid salts (e.g., salts formed with acetic acid, propionic acid, glutamic acid, citric acid and the like), quaternary ammonium salts (e.g., salts formed with methyl iodide, ethyl iodide, or the like). Salts of basic monomers and/or polymers, e.g., those having amine groups —$NR^1R^2$, can be formed with acids such as of mineral acids, organic carboxylic acids, and organic sulfonic acids, e.g., hydrochloric acid, methanesulfonic acid, maleic acid, and the like. Salts of acidic monomers and/or polymers can be formed with bases including cationic salts such as alkali and alkaline earth metal salts, such as sodium, lithium, potassium, calcium, magnesium salts, as well as ammonium salts, such as ammonium, trimethyl-ammonium, diethylammonium, and tris-(hydroxymethyl)-methyl-ammonium salts. The neutral form of a monomer or polymer can be regenerated by contacting the salt with a base or acid and optionally isolating the parent compound. Counterions (e.g., anions in a polycationic polymer) may be exchanged as described herein.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a value is close to a targeted value, where close can mean, for example, the value is within 80% of the targeted value, within 85% of the targeted value, within 90% of the targeted value, within 95% of the targeted value, or within 99% of the targeted value.

II. Monomer Compounds

Provided herein are compounds according to Formula (I), (II), (III), (IV), (V), (VI), (VII), and (VIII):

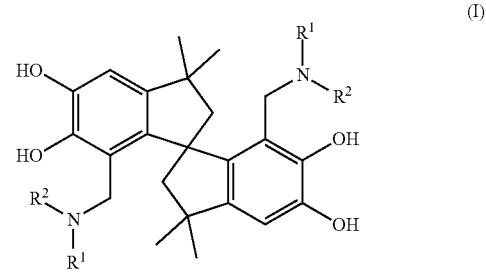

(I)

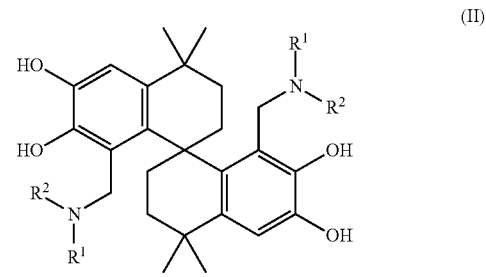

(II)

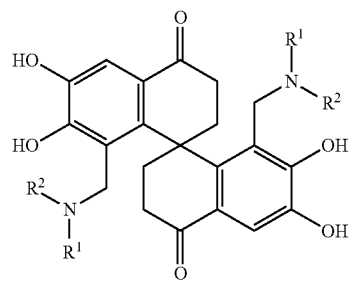
(III)

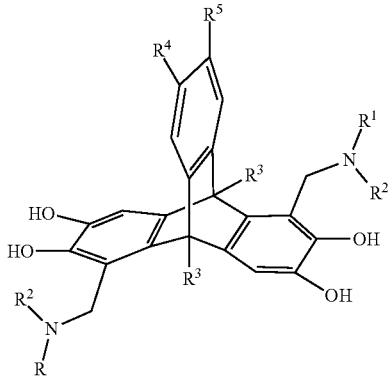
(VII)

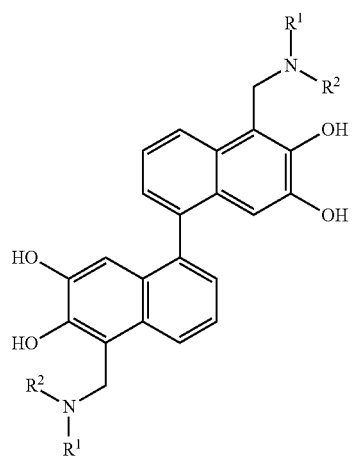
(IV)

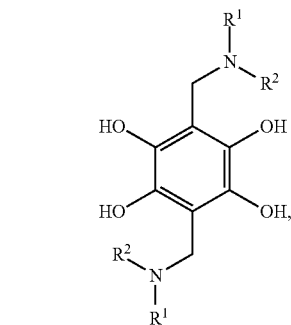
(VIII)

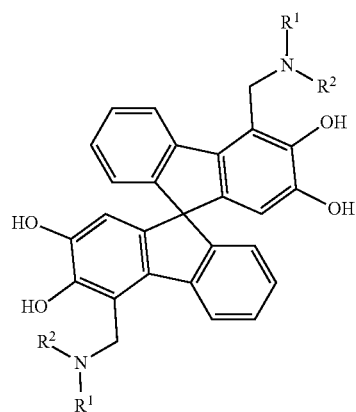
(V)

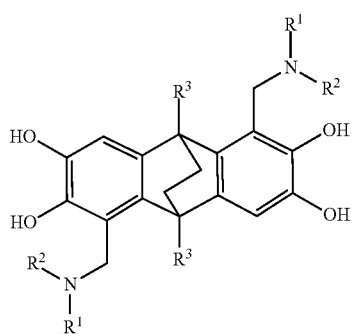
(VI)

and salts thereof, wherein:
each $R^1$ and $R^2$ is independently selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl-$(C_{1-20})$alkyl, $(C_{3-8})$cycloalkyl$(C_{1-20})$alkyl, hetero$(C_{1-20})$alkyl, 3- to 8-membered heterocyclyl, 3- to 8-membered heterocyclyl-$(C_{1-20})$alkyl, 5- to 8-membered heteroaryl, 5- to 8-membered heteroaryl-$(C_{1-20})$alkyl, wherein each $R^1$ and $R^2$ is optionally and independently substituted with one or more $Z^1$,
wherein each alkyl, alkenyl, and alkynyl in $R^1$ and $R^2$ optionally and independently comprises one or more heteroatoms independently selected from silicon, a chalcogenide, and a pnictide, and
wherein one or more atoms in $R^1$ and $R^2$ are optionally and independently present in oxidized form as C=O, C=S, N=O, N=S, S=O or $S(O)_2$;
alternatively, each $R^1$ is optionally and independently taken together with $R^2$, and the nitrogen atom to which both are attached, to form 3- to 8-membered heterocyclyl or 5- to 8-membered heteroaryl, each of which is optionally substituted with one or more $Z^2$;
each $Z^1$ and $Z^2$ is independently selected from the group consisting of halogen, —OH, —$NO_2$, —CN, $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl, 3- to 8-membered heterocyclyl, 5- to 8-membered heteroaryl, $(C_{3-8})$cycloalkyl-$(C_{1-20})$alkyl, 3- to 8-membered heterocyclyl-$(C_{1-20})$alkyl, 5- to 8-membered heteroaryl-$(C_{1-20})$alkyl, halo$(C_{1-20})$alkyl, halo$(C_{1-20})$alkyloxy, —$OR^6$, —$SR^6$, —$S(O)R^6$, —$S(O)_2R^6$, —$SO_2NR^6R^7$, —$NR^6C(O)R^7$, —$NR^6S(O)_2R^7$, —$NR^6C(O)NR^7R^8$, —$NR^6R^7$, —$CO_2R^6$, —$C(O)NR^6R^7$, and —$C(O)R^6$;
each $R^3$, $R^4$, $R^5$, $R^6$, $R^7$, and $R^8$ is independently selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, $(C_{3-8})$cycloalkyl$(C_{1-20})$alkyl, hetero$(C_{1-20})$alkyl, 3- to 8-membered heterocyclyl, 3- to 8-membered heterocyclyl-$(C_{1-20})$alkyl, 5- to 8-membered heteroaryl, 5- to 8-membered heteroaryl-$(C_{1-20})$alkyl; or alternatively, $R^4$ and $R^5$ are taken together to form $(C_{4-8})$cycloalkyl, $(C_{6-12})$aryl, 4- to 8-membered heterocyclyl, or 5- to 8-membered heteroaryl; or alternatively, $R^6$ and $R^7$ are taken together to form 4- to 8-membered heterocyclyl or 5- to 8-membered heteroaryl; or alternatively, $R^7$ and $R^8$ are taken together to form 4- to 8-membered heterocyclyl or 5- to 8-membered heteroaryl.

Compounds according to Formula (I), (II), (III), (IV), (V), (VI), (VII), and (VIII) can be used as monomers for the synthesis of polymers of intrinsic microporosity (PIMs) as described herein.

In some embodiments, each alkyl, alkenyl, and alkynyl in $R^1$ and $R^2$ optionally and independently comprises one or more chalcogenides (preferably O, S, or Se) or a pnictides. In some embodiments, each chalcogenide is selected from O, S, and Se. In some embodiments, each pnictide is selected from N and P.

In some embodiments, $R^1$ and $R^2$ are directly bonded together to form a, 3, 4, or 5 membered heterocyclyl or heteroaryl. In some embodiments, $R^1$ and $R^2$ are bonded together with a linker $X^1$ to form a 6, 7, or 8 membered heterocyclyl or heteroaryl. In some embodiments, $X^1$ is independently selected from the group consisting of C, Si, chalcogenide (preferably O, S, or Se), or a pnictide (preferably N, or P).

In some embodiments, $R^4$ and $R^5$ can also be bonded together to form a 4, 5, 6, 7, or 8 membered cycloaryl, heterocyclylaryl, or heteroaryl. In some embodiments, $R^4$ and $R^5$ can also be bonded together with a linker $X^2$ to form a 6, 7, or 8 membered cycloalkyl, cycloaryl, or heterocyclyl. In some embodiments, $R^6$ and $R^7$ can also be bonded together to form a 4, 5, 6, 7, or 8 membered heterocyclyl or heteroaryl. In some embodiments, $R^6$ and $R^7$ can also be bonded together with a linker $X^5$ to form a 6, 7, or 8 membered heterocyclyl or heteroaryl. In some embodiments, $R^7$ and $R^8$ can also be bonded together to form a 4, 5, 6, 7, or 8 membered heterocyclyl or heteroaryl. In some embodiments, $R^7$ and $R^8$ can also be bonded together with a linker $X^6$ to form a 6, 7, or 8 membered heterocyclyl or heteroaryl. In some embodiments, $X^2$, $X^3$, $X^4$, $X^5$, and/or $X^6$ are independently selected from the group consisting of C, Si, chalcogenide (preferably O, S, or Se), or a pnictide (preferably N, or P).

In some embodiments, the monomer is a compound according to Formula (I), Formula (II), Formula (III), or Formula (IV), containing any of the $R^1$ and $R^2$ moieties set forth above. Amine moieties —NR$^1$R$^2$ may be introduced according to the methods provided herein, employing a formaldehyde source and an appropriate amine. Numerous suitable amines are commercially available or can be prepared according to known methods, including those described in *Fiesers' Reagents for Organic Synthesis* Volumes 1-28 (John Wiley & Sons, 2016), by March (*Advanced Organic Chemistry* 6$^{th}$ Ed. John Wiley & Sons, 2007), and by Larock (*Comprehensive Organic Transformations* 3$^{rd}$ Ed. John Wiley & Sons, 2018). In some embodiments, the monomer is a compound according to Formula (I), Formula (II), Formula (III), or Formula (IV), wherein each $R^1$ and $R^2$ is independently selected from the group consisting of $(C_{1-8})$alkyl, $(C_{2-8})$alkenyl, $(C_{2-8})$alkynyl, $(C_{6-12})$aryl, and $(C_{3-8})$cycloalkyl, each of which is optionally substituted with one or more $Z^1$. $R^1$ and $R^2$ may independently be, for example, substituted or unsubstituted methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, or branched octyl. In some such embodiments, the monomer is a compound according to Formula (I).

In some embodiments, the monomer is a compound according to Formula (I), Formula (II), Formula (III), or Formula (IV), wherein $R^1$ and $R^2$ are taken together with the nitrogen atom to which they are attached to form 3- to 8-membered heterocyclyl or 5- to 8-membered heteroaryl, each of which is optionally substituted with one or more $Z^2$. In some such embodiments, $R^1$, $R^2$, and the nitrogen atom are taken together to form substituted or unsubstituted 5- to 8-membered heteroaryl, e.g., substituted or unsubstituted pyrrolyl, pyridinyl, imidazolyl, pyrazolyl, triazolyl, thiazolyl, tetrazolyl, pyrazinyl, triazinyl, indolyl, isoindolyl, or quinolinyl. In some such embodiments, the monomer is a compound according to Formula (I).

In some embodiments, $R^1$, $R^2$, and the nitrogen atom are taken together to form substituted or unsubstituted 3- to 8-membered heterocyclyl, e.g., substituted or unsubstituted aziridinyl, diaziridinyl, azetidinyl, oxetanyl, diazetidinyl, pyrrolidinyl, imidazolidinyl, pyrazolidinyl, oxazolidinyl, isoxazolidinyl, thiazolidinyl, piperidinyl, piperazinyl, or morpholinyl. A heterocyclic group such as imidazolidinyl, pyrazolidinyl, piperidinyl, or piperazinyl may be substituted with one or more $Z^2$ groups independently selected from —OH, hetero$(C_{1-20})$alkyl (e.g., (2-methoxy)ethyl), or —CO$_2$R$^6$, wherein R$^6$ is $(C_{1-6})$alkyl (e.g., —CO$_2$R$^6$ may be tert-butoxycarbonyl). In some such embodiments, the monomer is a compound according to Formula (I).

In some embodiments, the monomer is a compound according to Formula (VI) or Formula (VII), containing any of the $R^1$, $R^2$, $R^3$, $R^4$ and $R^5$ moieties set forth above. In some embodiments, the monomer is a compound according to Formula (VI) or Formula (VII), wherein each $R^1$ and $R^2$ is independently selected from the group consisting of $(C_{1-8})$alkyl, $(C_{2-8})$alkenyl, $(C_{2-8})$alkynyl, $(C_{6-12})$aryl, and $(C_{3-8})$cycloalkyl, each of which is optionally substituted with one or more $Z^1$. $R^1$ and $R^2$ may independently be, for example, substituted or unsubstituted methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, or branched octyl. In some such embodiments, each $R^3$ in compounds of Formula (VI) and (VII) is independently $(C_{1-8})$alkyl. In some such embodiments, $R^4$ and $R^5$ in compounds of Formula (VII) are also independently $(C_{1-8})$alkyl. In some embodiments, the monomer is a compound according to Formula (VI), and $R^1$, $R^2$, and $R^3$ are each independently $(C_{1-8})$alkyl.

In some embodiments, the monomer is a compound according to Formula (VI) or Formula (VII), wherein $R^1$ and $R^2$ are taken together with the nitrogen atom to which they are attached to form 3- to 8-membered heterocyclyl or 5- to 8-membered heteroaryl, each of which is optionally substituted with one or more $Z^2$. In some such embodiments, $R^1$, $R^2$, and the nitrogen atom are taken together to form substituted or unsubstituted 5- to 8-membered heteroaryl, e.g., substituted or unsubstituted pyrrolyl, pyridinyl, imidazolyl, pyrazolyl, triazolyl, thiazolyl, tetrazolyl, pyrazinyl, triazinyl, indolyl, isoindolyl, or quinolinyl. In some such embodiments, each $R^3$ in compounds of Formula (VI) and (VII) is independently $(C_{1-8})$alkyl. In some such embodiments, $R^4$ and $R^5$ in compounds of Formula (VII) are also independently $(C_{1-8})$alkyl. In some embodiments, the monomer is a compound according to Formula (VI), $R^1$ and $R^2$ are taken together with the nitrogen atom to which they are attached to form 3- to 8-membered heterocyclyl, which is optionally substituted with one or more $Z^2$, and each $R^3$ is $(C_{1-8})$alkyl.

In some embodiments, $R^1$, $R^2$, and the nitrogen atom in compounds of Formula (VI) or Formula (VII) are taken together to form substituted or unsubstituted 3- to 8-membered heterocyclyl, e.g., substituted or unsubstituted aziridinyl, diaziridinyl, azetidinyl, oxetanyl, diazetidinyl, pyrrolidinyl, imidazolidinyl, pyrazolidinyl, oxazolidinyl, isoxazolidinyl, thiazolidinyl, piperidinyl, piperazinyl, or morpholinyl. A heterocyclic group such as imidazolidinyl, pyrazolidinyl, piperidinyl, or piperazinyl may be substituted with one or more $Z^2$ groups independently selected from —OH, hetero$(C_{1-20})$alkyl (e.g., (2-methoxy)ethyl), or —$CO_2R^6$, wherein $R^6$ is $(C_{1-6})$alkyl (e.g., —$CO_2R^6$ may be tert-butoxycarbonyl). In some such embodiments, each $R^3$ in compounds of Formula (VI) and (VII) is independently $(C_{1-8})$alkyl. In some such embodiments, $R^1$ and $R^5$ in compounds of Formula (VII) are also independently $(C_{1-8})$alkyl. In some embodiments, the monomer is a compound according to Formula (VI), $R^1$ and $R^2$ are taken together with the nitrogen atom to which they are attached to form 3- to 8-membered heterocyclyl, which is optionally substituted with one or more $Z^2$, and each $R^3$ is $(C_{1-8})$alkyl.

Also provided herein are methods for preparing compounds according to Formula (I)-(VIII) as described above. The methods include:

forming a mixture comprising (i) an amine precursor having the formula $R^1$—NH—$R^2$, (ii) formaldehyde or a formaldehyde-generating compound, and (iii) a compound selected from (Ia), (IIa), (IIIa), (IVa), (Va), (VIa), (VIIa), or (VIIIa):

(Ia)

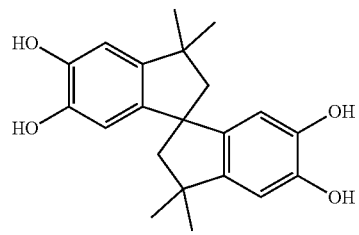

(IIa)

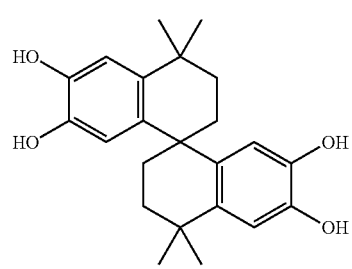

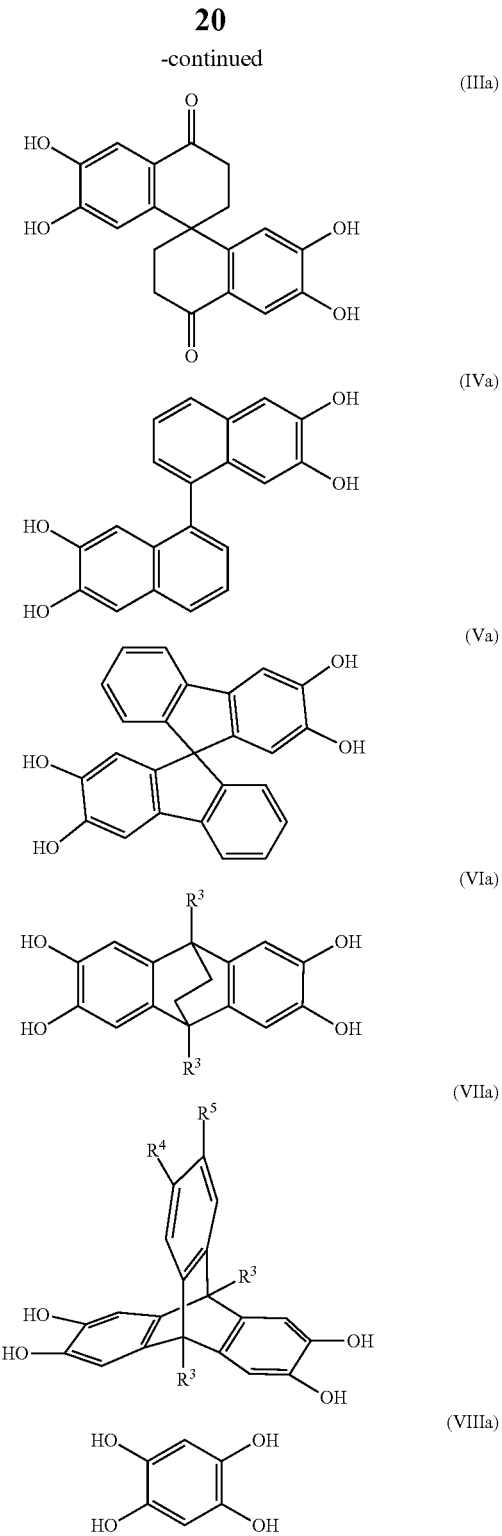

and maintaining the mixture under conditions sufficient to form the compound of Formula (I), (II), (III), (IV), (V), (VI), (VII), or (VIII).

Starting materials according to Formula (Ia), (IIa), (IIIa), (IVa), (Va), (VIa), (VIIa), or (VIIIa) may be obtained from commercial sources or synthesized according to the methods described herein or according to other known methods. See, e.g., *Chemical Reviews* 2018, 118(12), 5871-5911; *Advanced Materials* 2018, 30, 1704953; *Science China:*

Chemistry 2017, 60(8), 1023-1032; *Progress in Polymer Science* 2015, 43, 1-32; *Encyclopedia of Membrane Science and Technology* 2013, 2, 781-797; *Polymer* 2013, 54(18), 4729-4761; *Macromolecules* 2010, 43(12), 5163-5176; *Polymer Chemistry* 2010, 1(1), 63-68; *Chemical Society Reviews* 2006, 35(8), 675-683; *Chemistry—A European Journal* 2005, 11(9), 2610-2620; and references cited therein. Amine precursors used in the methods may have any combination of $R^1$ and $R^2$ set forth above. Formaldehyde, as well as formaldehyde-generating compounds such as paraformaldehyde or 1,3,5-trioxane, may be employed. Typically, the amine precursor and the formaldehyde/formaldehyde-generating compound will be used in excess with respect to the starting material. For example, 2-250 molar equivalents of the amine precursor and the formaldehyde/formaldehyde-generating compound with respect to the starting material may be used. In some embodiments, 25-75 molar equivalents of an amine precursor (e.g., pyrrolidine, a substituted or substituted piperazine, or morpholine) and a formaldehyde-generating compound (e.g., paraformaldehyde) with respect to the starting material (e.g., a compound of Formula (Ia) or a compound of Formula (VIa)) are used to form the monomer product. Reactions are typically conducted at temperatures ranging from around −10° C. to about 150° C. for a period of time sufficient to form the monomer product (e.g., from about 1 hour to about 18 hours), depending on factors such as the particular starting material or amine precursor used in the reaction. In some embodiments, the reaction is conducted at ambient temperature (e.g., about 20° C., or about 25° C.). Elevated temperatures may be achieved through conventional heating or through microwave-assisted heating. Reaction mixtures may contain a solvent or mixture of solvents including, but not limited to, further comprises a solvent or mixture of solvents. The solvent may be, but it not limited to, methanol, ethanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, or a mixture thereof.

III. Microporous Polymers

Also provided herein are microporous polymers, e.g., polymers according to the formula:

-[A-AB-B]$_n$— and salts thereof, wherein:
n is an integer ranging from 10 to 10,000;
each monomer segment A-A is independently a monomer segment according to Formula (A), (B), (C), (D), (E), (F), (G) or (H):

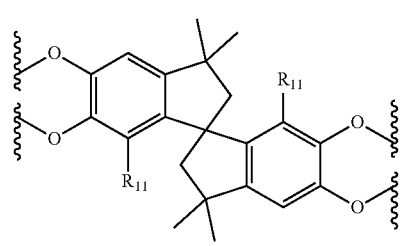

(A)

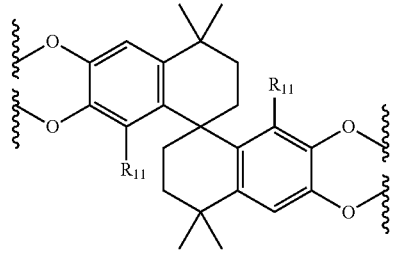

(B)

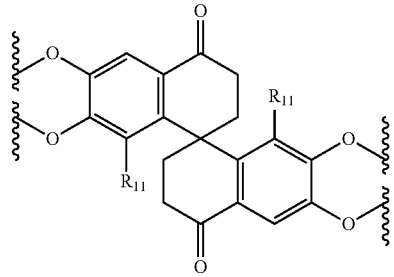

(C)

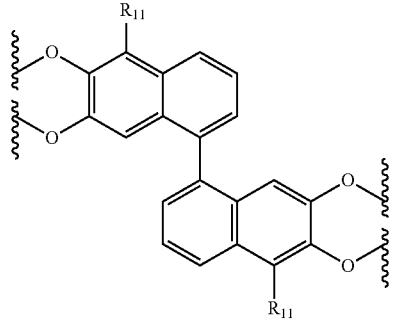

(D)

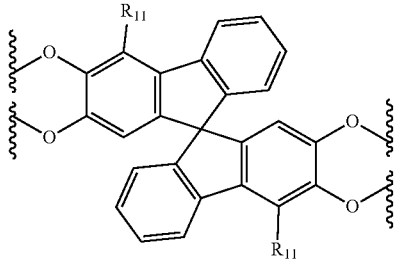

(E)

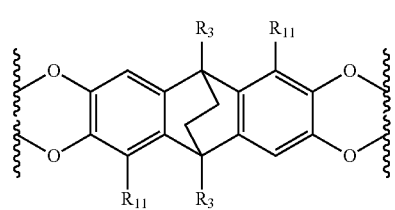

(F)

-continued (G)
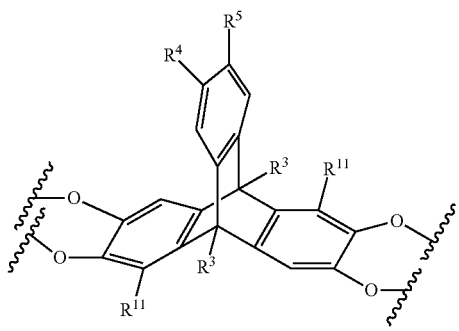

(H)
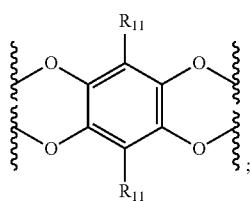

each monomer segment B-B is independently a monomer segment according to Formula (a), (b), (c), (d), (e), or (f):

(a)
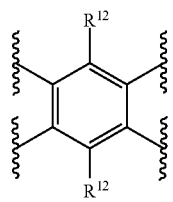

(b)
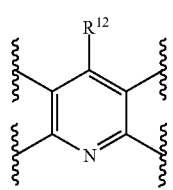

(c)
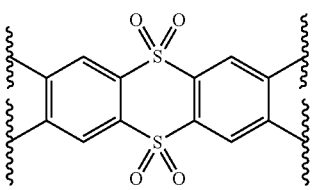

(d)
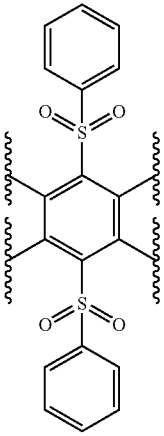

(e), (f)
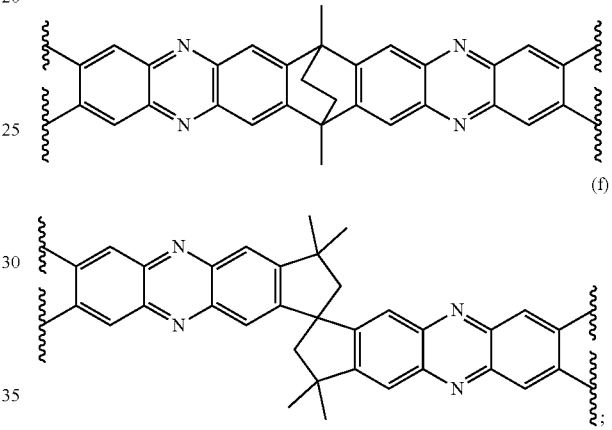

each $R^{11}$ is independently selected from the group consisting of H and —$CH_2NR^1R^2$;

each $R^{12}$ is independently selected from the group consisting of —CN and —$C(NOR^{13})N(R^{14})_2$;

at least one $R^{11}$ in at least one monomer segment A-A is —$CH_2NR^1R^2$, or at least one $R^{12}$ in at least one monomer segment B-B is —$C(NOR^{13})N(R^{14})_2$;

each $R^1$ and $R^2$ is independently selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, $(C_{3-8})$cycloalkyl$(C_{1-20})$alkyl, hetero$(C_{1-20})$alkyl, 3- to 8-membered heterocyclyl, 3- to 8-membered heterocyclyl-$(C_{1-20})$alkyl, 5- to 8-membered heteroaryl, heteroaryl$(C_{1-20})$alkyl, wherein each $R^1$ and $R^2$ is optionally and independently substituted with one or more $Z^1$, wherein each alkyl, alkenyl, and alkynyl in $R^1$ and $R^2$ optionally and independently comprises one or more heteroatoms independently selected from silicon, a chalcogenide, and a pnictide, and wherein one or more atoms in $R^1$ and $R^2$ are optionally and independently present in oxidized form as C=O, C=S, N=O, N=S, S=O or $S(O)_2$; or alternatively, each $R^1$ is optionally and independently taken together with $R^2$, and the nitrogen atom to which both are attached, to form 3- to 8-membered heterocyclyl or 5- to 8-membered heteroaryl, each of which is optionally substituted with one or more $Z^2$;

each $Z^1$ and $Z^2$ is independently selected from the group consisting of halogen, —OH, —$NO_2$, —CN, $(C_{1-20})$ alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl, 3- to 8-membered heterocyclyl, 5- to 8-membered heteroaryl, $(C_{3-8})$cycloalkyl$(C_{1-20})$alkyl, 3- to 8-membered heterocyclyl-$(C_{1-20})$alkyl, 5- to 8-membered heteroaryl-$(C_{1-20})$alkyl, halo$(C_{1-20})$alkyl, halo$(C_{1-20})$alkyloxy, —OR$^6$, —SR$^6$, —S(O)R$^6$, —S(O)$_2$R$^6$, —SO$_2$NR$^6$R$^7$, —NR$^6$C(O)R$^7$, —NR$^6$S(O)$_2$R$^7$, —NR$^6$C(O)NR$^7$R$^8$, —NR$^6$R$^7$, —CO$_2$R$^6$, —C(O)NR$^6$R$^7$, and —C(O)R$^7$;

each R$^3$, R$^4$, R$^5$, R$^6$, R$^7$, and R$^8$ is independently selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, $(C_{3-8})$cycloalkyl$(C_{1-20})$alkyl, hetero$(C_{1-20})$alkyl, 3- to 8-membered heterocyclyl, 3- to 8-membered heterocyclyl-$(C_{1-20})$alkyl, 5- to 8-membered heteroaryl, 5- to 8-membered heteroaryl-$(C_{1-20})$alkyl; or alternatively, R$^4$ and R$^5$ are taken together to form $(C_{4-8})$cycloalkyl, $(C_{6-12})$aryl, 4- to 8-membered heterocyclyl, or 5- to 8-membered heteroaryl; or alternatively, R$^6$ and R$^7$ are taken together to form 4- to 8-membered heterocyclyl or 5- to 8-membered heteroaryl; or alternatively, R$^7$ and R$^8$ are taken together to form 4- to 8-membered heterocyclyl or 5- to 8-membered heteroaryl;

each R$^{13}$ is selected from the group consisting of H, $(C_{1-20})$alkyl, and $(C_{3-8})$cycloalkyl, wherein alkyl and cycloalkyl are optionally and independently substituted with one or more Z$^3$, provided that R$^{13}$ is $(C_{1-20})$alkyl or $(C_{3-8})$cycloalkyl when all R$^{11}$ groups in monomer segments according to formula (A) are H;

each R$^{14}$ is independently selected from the group consisting of H, $(C_{1-20})$alkyl, and $(C_{3-8})$cycloalkyl; and each Z$^3$ is independently selected from the group consisting of halogen, —NO$_2$, —CN, —OH, —SO$_3$H, —NH$_2$, $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl, 3- to 8-membered heterocyclyl, 5- to 8-membered heteroaryl, $(C_{3-8})$cycloalkyl-$(C_{1-20})$alkyl, 3- to 8-membered heterocyclyl-$(C_{1-20})$alkyl, 5- to 8-membered heteroaryl-$(C_{1-20})$alkyl, halo$(C_{1-20})$alkyl, halo$(C_{1-20})$alkyloxy, —OR$^6$, —SR$^6$, —S(O)R$^6$, —S(O)$_2$R$^6$, —SO$_2$NR$^6$R$^7$, —NR$^6$C(O)R$^7$, —NR$^6$S(O)$_2$R$^7$, —NR$^6$C(O)NR$^7$R$^8$, —NR$^6$R$^7$, —CO$_2$R$^6$, —C(O)NR$^6$R$^7$, and —C(O)R$^6$.

In general, no specification of the chain ends is assumed for polymers of the formula -[A-AB-B]$_n$—. That is, either chain end can contain a monomer segment A-A or a monomer segment B-B, independent of the other chain end. At the chain ends, however, moieties represented as

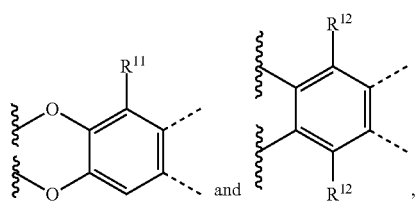

in any of the monomer segments depicted herein will be present as catechols:

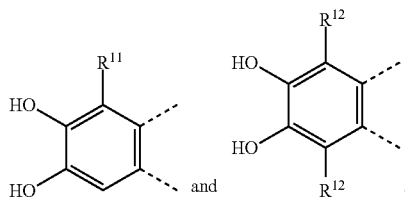

In the structures above, the dashed bonds represent the connection to the remainder of the polymer chain, and R$^{11}$ and R$^{12}$ can include any of the moieties and combinations thereof as set forth herein.

In some embodiments, each monomer segment A-A is independently a monomer segment according to Formula (A-i), (B-i), (C-i), (D-i), (E-i), (F-i), (G-i) or (H-i):

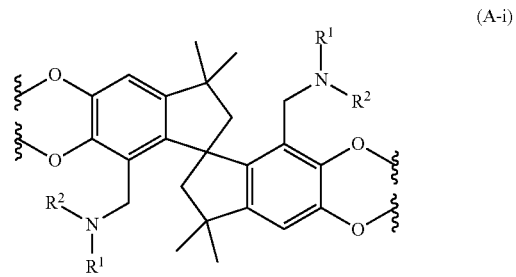

(A-i)

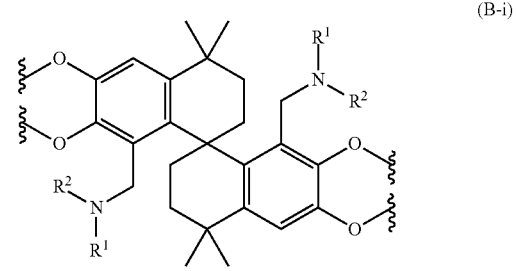

(B-i)

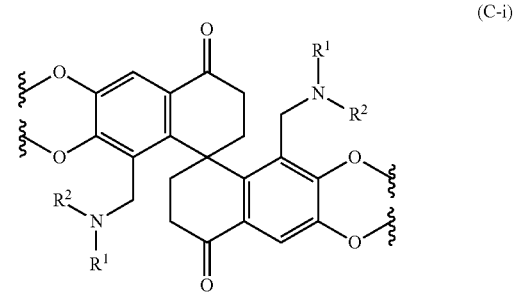

(C-i)

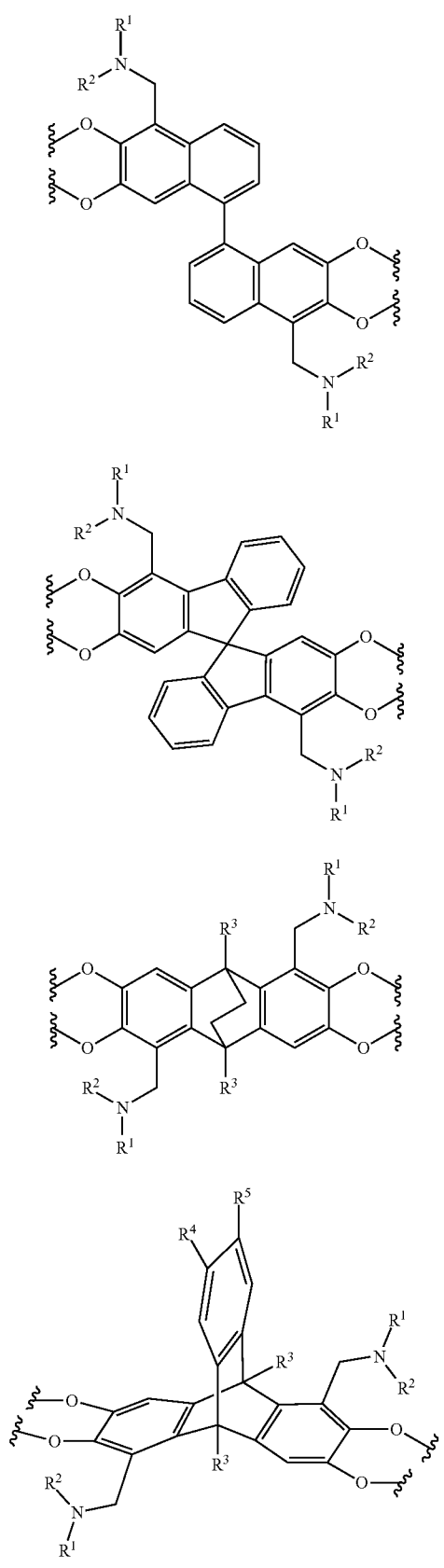
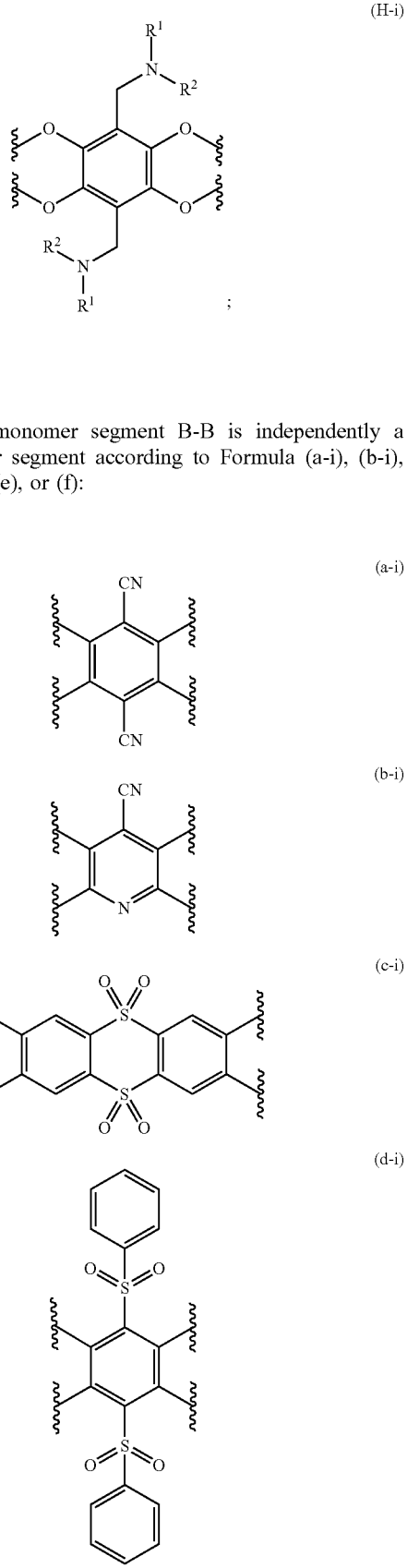
and each monomer segment B-B is independently a monomer segment according to Formula (a-i), (b-i), (c), (d), (e), or (f):

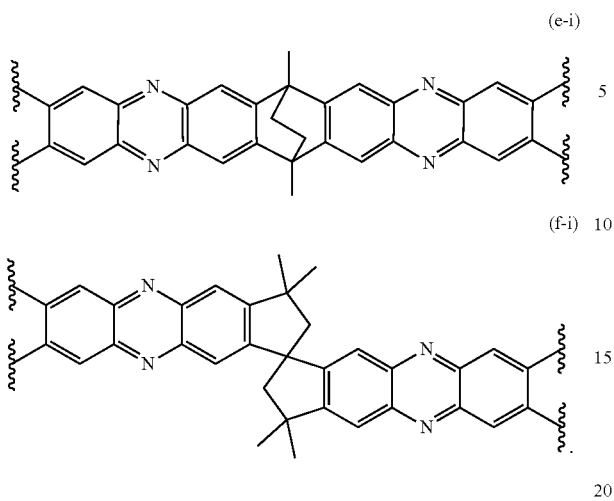
(e-i)
(f-i)
In some embodiments, each monomer segment A-A segment independently a monomer segment according to Formula (A-i), (B-i), (C-i), (D-i), (E-i), (F-i), (G-i), (H), (B-ii), (C-ii), (C-ii), (E-ii), (F-ii), (G-ii), or (H-ii):
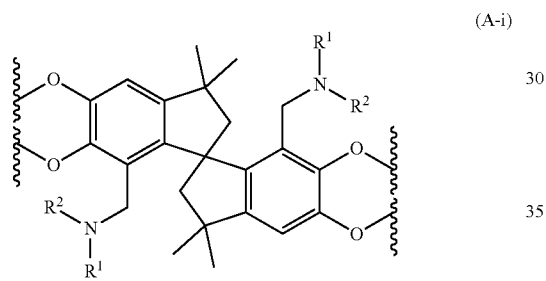
(A-i)
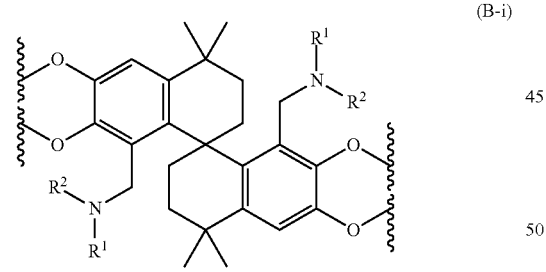
(B-i)
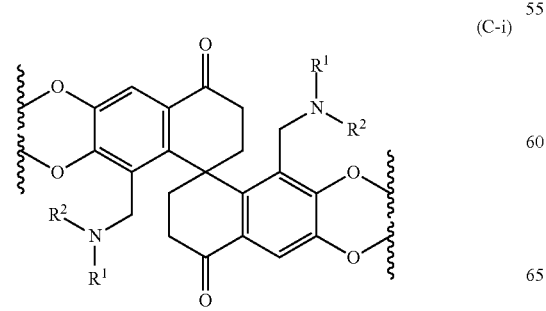
(C-i)
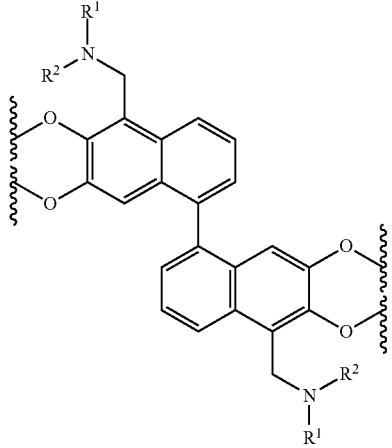
(D-i)
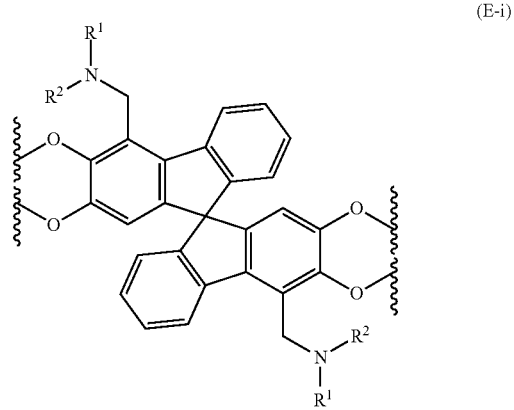
(E-i)
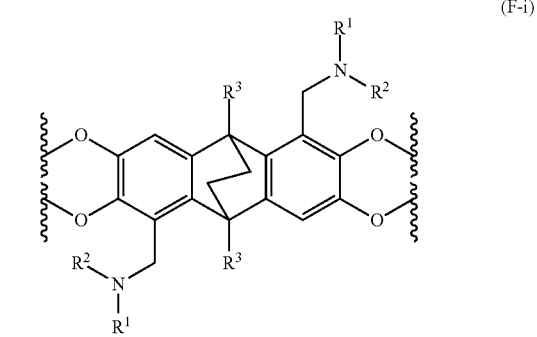
(F-i)
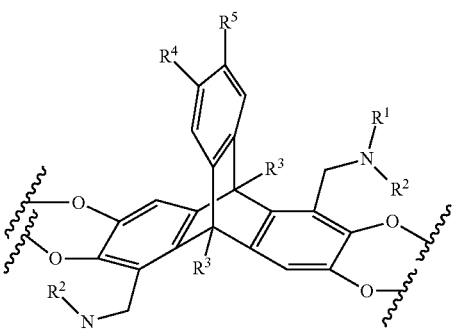
(G-i)

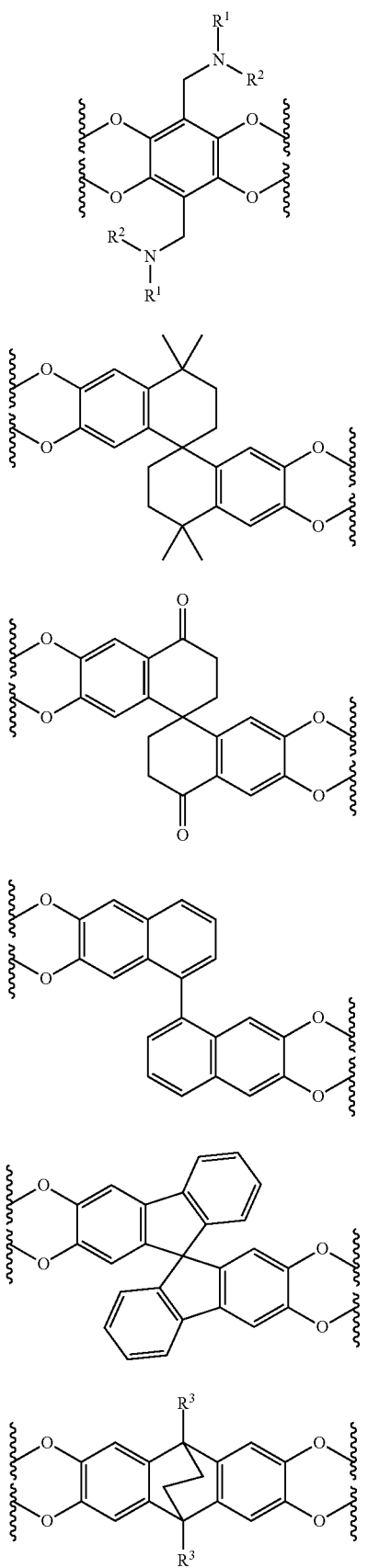
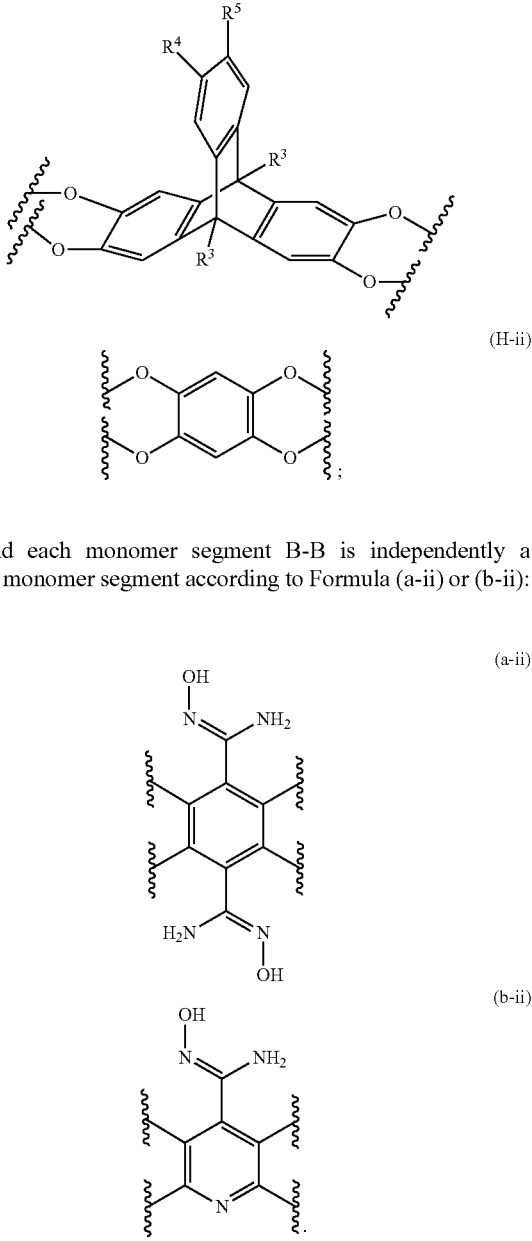
and each monomer segment B-B is independently a monomer segment according to Formula (a-ii) or (b-ii):
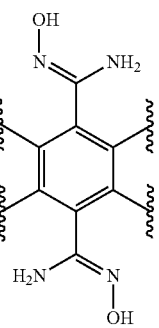
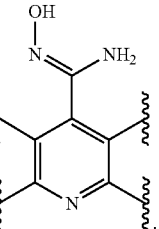
In some embodiments, each monomer segment A-A is independently a monomer segment according to Formula (A-i), (B-i), (C-i), (D-i), (E-i), (F-i), (G-i), (H-i), (B-ii), (C-ii), (D-ii), (E-ii) (F-i), (G-ii) ((H-i), or (A-ii):
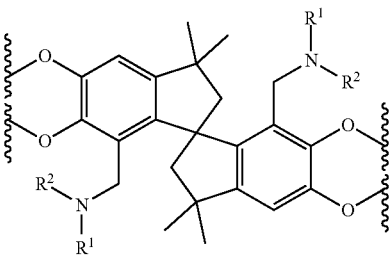

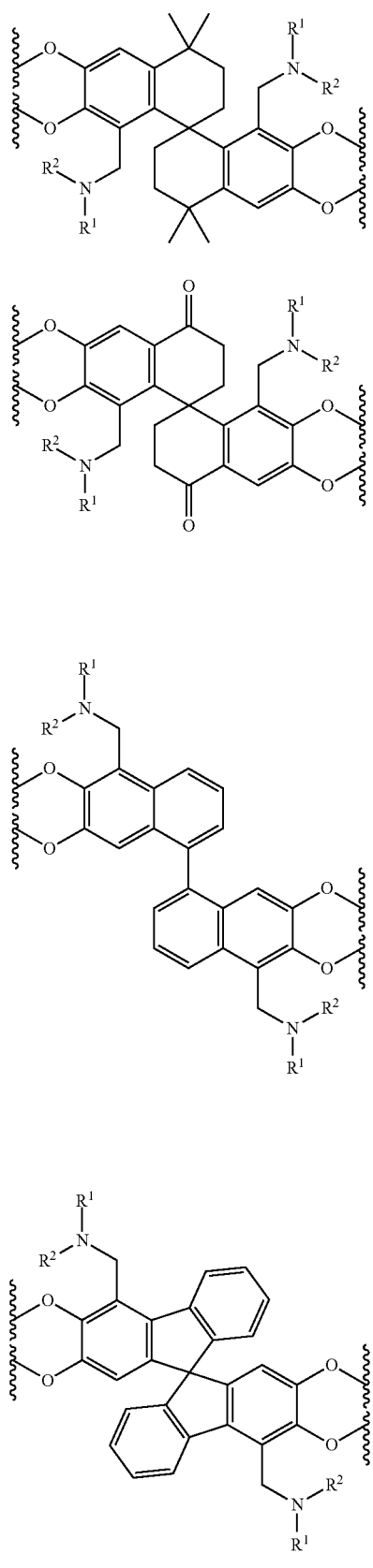
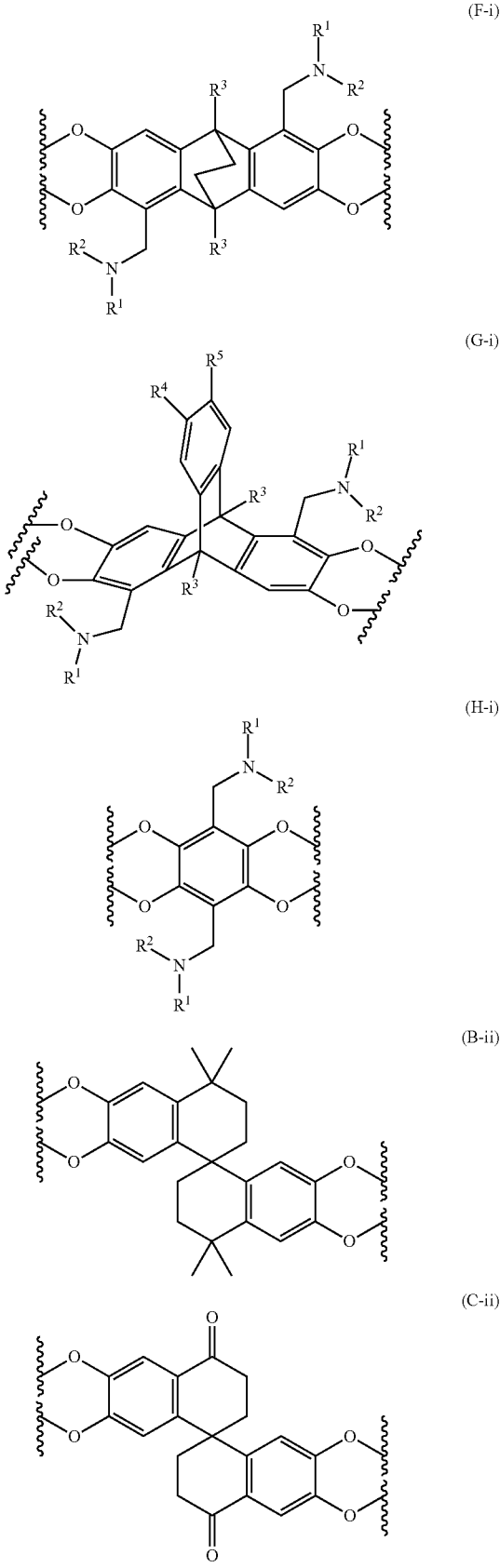

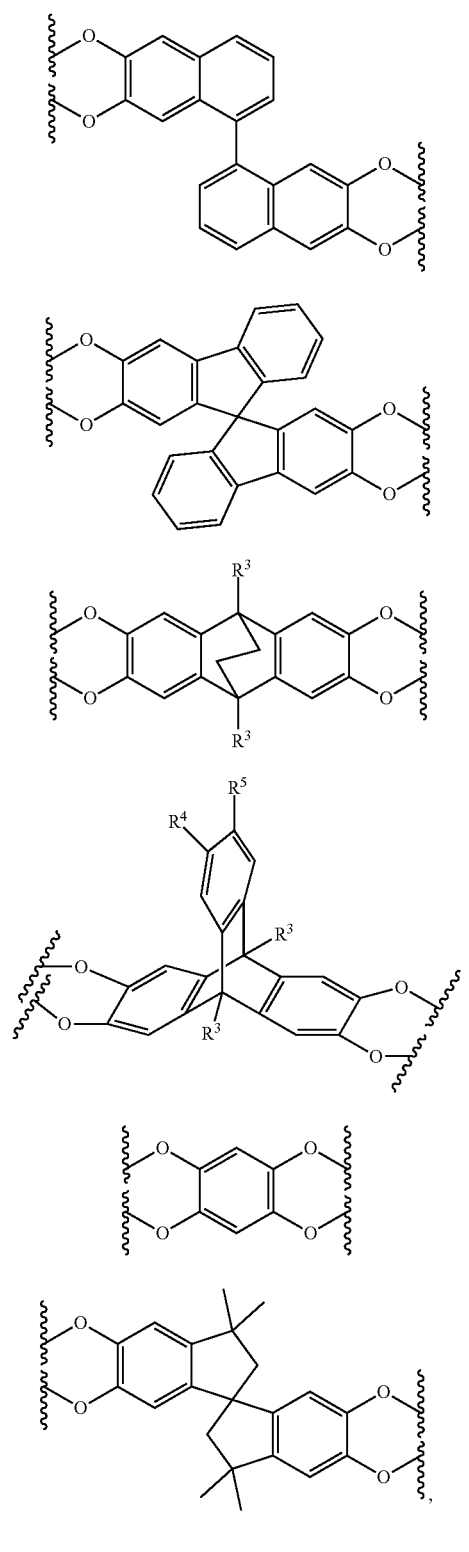
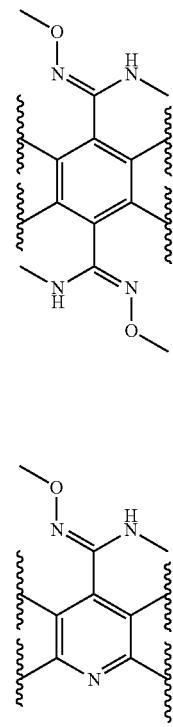
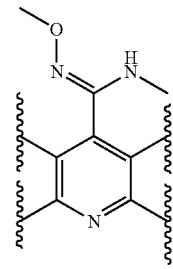
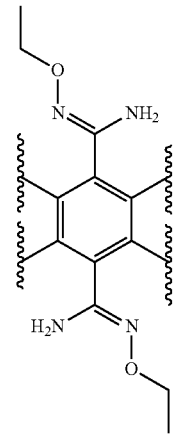
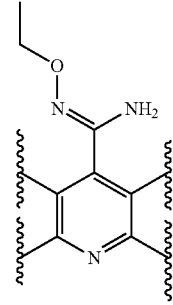
and each monomer segment B-B is independently a monomer segment according to Formula (a-iii), (b-iii), (a-iv), (b-iv), (a-v), (b-v), (a-vi), (b-vi), (a-vii), (b-vii), (a-viii), or (b-viii):

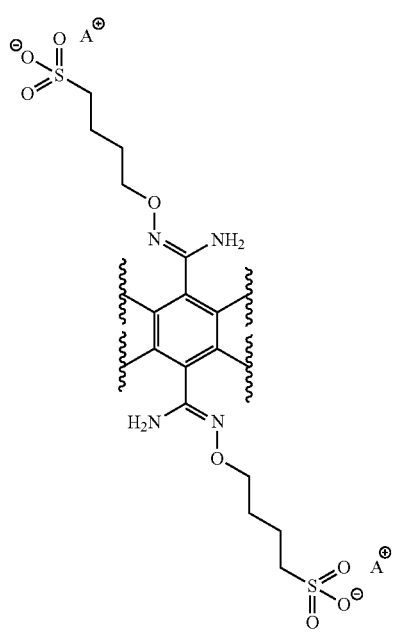
(a-v)
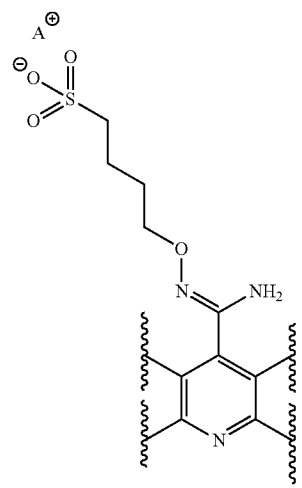
(b-v)
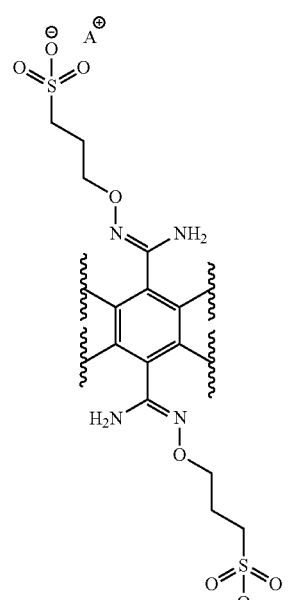
(a-vi)
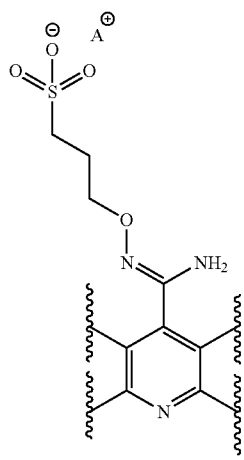
(b-vi)
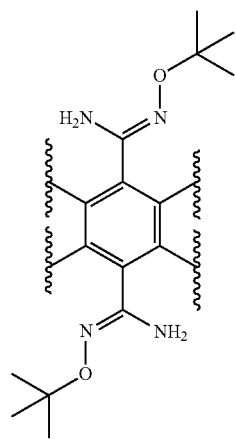
(a-vii)

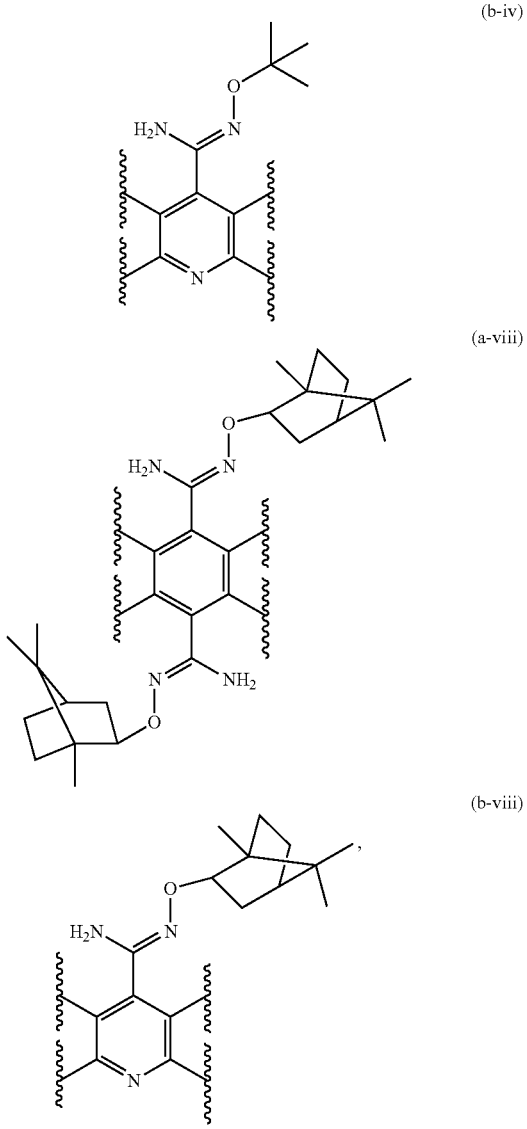

wherein A⁺ is an inorganic cation or an organic cation.

In some embodiments, the inorganic cation is an alkali cation, such as a lithium cation (Li⁺), a sodium cation (Na⁺), or a potassium cation (K⁺). In some embodiments, the organic cation is a tetraalkylammonium cation (NR$_4^+$) or a tetraalkylphosphonium cation (PR$_4^+$), wherein each R group is an alkyl group as described herein.

In some embodiments, each monomer segment B-B is independently a monomer segment according to Formula (a-iii), (b-iii), (a-iv), (b-iv), (a-v), (b-v), (a-vi), or (b-vi).

In some embodiments, each monomer segment B-B is independently a monomer segment according to Formula (a-vii), (b-vii), (a-viii), or (b-viii).

Polymers according to the present disclosure may contain monomer segments according to Formula (A)-(H) and/or Formula (A-i)-(H-i) having any combination of R¹, R², R³, R⁴, and R⁵ groups set forth above for monomer compounds according to Formula (I)-(VIII).

In some embodiments, at least one R¹² in one or more monomer segments according to Formula (a) or Formula (b) is —CN. Such polymers include, but are not limited to, those having one or more monomer segments according to Formula (a-i) or Formula (b-i), or a combination thereof.

In some embodiments, the polymer contains monomer segments wherein at least one R¹² is —C(NOR¹³)N(R¹⁴)₂, and wherein R¹³ and R¹⁴ is H. Such polymers include, but are not limited to, those having one or more monomer segments according to Formula (a-ii) or Formula (b-ii), or a combination thereof. In general, when a polymer of the present disclosure contains monomer segments A-A according to Formula A-ii alone, the polymer will contain at least one monomer segments B-B wherein some embodiments, wherein at least one R¹² is —C(NOR¹³)N(R¹⁴)₂, and at least one R¹³ or R¹⁴ is (C₁₋₂₀)alkyl or (C₃₋₈)cycloalkyl. In some such embodiments, the polymer consists of monomer segments A-A according to Formula A-ii and monomer segments according to Formula (a) or Formula (b), wherein R¹² is —C(NOR¹³)N(R¹⁴)₂, and each R¹³ is (C₁₋₂₀)alkyl or (C₃₋₈)cycloalkyl, each of which is optionally and independently substituted with one or more Z³.

In some embodiments, each R¹² in one or more monomer segments according to Formula (a) or Formula (b) is —C(NOR¹³)N(R¹⁴)₂. For example, each R¹³ may independently be (C₁₋₈)alkyl, (C₂₋₈)alkenyl, (C₂₋₈)alkynyl, (C₆₋₁₂)aryl, or (C₃₋₈)cycloalkyl, each of which may be optionally substituted with one or more Z³. In some embodiments, R¹³ is substituted or unsubstituted methyl, ethyl, n-propyl, isopropyl, n-butyl, isobutyl, sec-butyl, tert-butyl, n-pentyl, branched pentyl, n-hexyl, branched hexyl, n-heptyl, branched heptyl, n-octyl, or branched octyl. In some embodiments, R¹³ is substituted or unsubstituted cyclopropyl, cyclobutyl, cyclopentyl, cyclohexyl, cycloheptyl, bicycloheptyl (e.g., bicyclo[2.2.1]heptyl), cyclooctyl, or bicyclooctyl (e.g., bicyclo[2.2.2]octyl). An alkyl group (e.g., n-propyl, n-butyl, or n-pentyl) or a cycloalkyl group (e.g., bicyclo[2.2.1]heptyl) may be optionally substituted with one or more Z³ groups independently selected from halogen, —NO₂, —CN, —OH, —SO₃H, —NH₂, and (C₁₋₈)alkyl. In some embodiments, the Z³-substituted R¹³ moiety is a sulfonate-substituted alkyl group such as 4-sulfonatobutyl, 3-sulfonatopropyl, or the like. In some embodiments, the Z-substituted R¹³ moiety is a bicyclic or polycyclic carbocycle such as 1,7,7-trimethylbicyclo[2.2.1]heptyl, 1,3-dimethyladamantyl, or the like. R¹⁴ in any of these instances may be, for example, hydrogen or (C₁₋₈)alkyl.

In some embodiments, polymers of intrinsic microporosity may be characterized by a surface area. In some embodiments, polymers of intrinsic microporosity may be characterized by gas adsorption/desorption amount and rates, such as for N₂ adsorption/desorption, which may allow for determination of their surface area, for example. Adsorption isotherms may be determined to allow for determination of a Brunauer, Emmett, and Teller (BET) surface area. BET surface areas may allow for comparison of microporosity characters, for example, between different polymers of intrinsic microporosity. For example, a first polymer of intrinsic microporosity that exhibits a smaller BET surface area than a second polymer of intrinsic microporosity may be characterized as having less microporosity than the second polymer of intrinsic microporosity. Useful unmodified and modified polymers of intrinsic microporosity include, but are not limited to, those exhibiting a surface area of at least 300 m²/g, such as a surface area selected from the range of 200 m²/g to 1000 m²/g, or from the range of 250 m²/g to 800 m²/g.

Microporosity and pore sizes of polymers of intrinsic microporosity may be characterized by determining the effective rate of diffusion of one or more gases across a film of the polymer having a known thickness. Microporosity and pore size characteristics of polymers of intrinsic microporosity may also be probed using positron annihilation lifetime spectroscopy.

In some embodiments, polymers of intrinsic microporosity may be characterized by their solubility in organic solvents, such as tetrahydrofuran or chloroform. In some embodiments, polymers of intrinsic microporosity may exhibit high solubility in organic solvents, while other polymers may exhibit low or no solubility in organic solvents.

In some embodiments, polymers of intrinsic microporosity may be characterized by their molecular weights. Optionally, size exclusion chromatography may be useful for determining molecular weights of polymers of intrinsic microporosity. Optionally, gel permeation chromatography may be useful for determining molecular weights of polymers of intrinsic microporosity. Molecular weight determination may, in turn, allow for determination of a degree of polymerization of a polymer of intrinsic microporosity. Example polymers of intrinsic microporosity include, but are not limited to, those exhibiting molecular weights of at least 50 kg/mol, at least 100 kg/mol, at least 200 kg/mol, or at least 300 kg/mol. In some embodiments, polymers of intrinsic microporosity exhibit molecular weights selected from the range of about 50 kg/mol to about 250 kg/mol, or from the range of about 80 kg/mol to about 200 kg/mol. Example polymers of intrinsic microporosity include, but are not limited to, those exhibiting degrees of polymerization selected from the range of 100 to 1000, from the range of 200 to 900, from the range of 300 to 800, from the range of 400 to 700, or from the range of 500 to 600.

Chemical structure characterization of polymers of intrinsic microporosity may be accomplished using a variety of techniques. Such characterizations may also allow for determination of modifications and degrees of modifications to polymers of intrinsic microporosity. For example, $^1$H and $^{13}$C nuclear magnetic resonance (NMR) spectroscopy may be useful. In some embodiments, infrared spectroscopy may also be useful. Additionally or alternatively, ionization mass spectrometry, such as electrospray ionization mass spectrometry, may also be useful for identifying structural moieties within a polymer of intrinsic microporosity.

Other characterization techniques known to the skilled artisan may be useful for characterizing unmodified polymers of intrinsic microporosity and modified polymers of intrinsic microporosity. For example, in some embodiments, polymers of intrinsic microporosity may be characterized by their ultraviolet and/or visible absorption spectra. As another example, a modified polymer of intrinsic microporosity may be characterized by an extent, density, or degree of crosslinking, such as by use of known standard techniques that evaluate how much a crosslinked polymer swells in a particular solvent at a particular temperature. Example standards include ASTM D2765 and ASTM F2214.

In some embodiments, the microporous polymers have any one or more of the following properties: a surface area of ranging from about 5 m$^2$ g$^{-1}$ to about 1000 m$^2$ g$^{-1}$; pore sizes ranging from about 0.4 nm to about 5 nm; and a porosity ranging from about 5% to about 40%. Percent porosity φ may be defined as φ=$V_V/V_T$×100%, wherein $V_V$ is the void volume and $V_T$ is the total volume. The void volume of a particular material can be determined based on pore size characterization as described herein.

Microporous polymers according to the present disclosure may have varying proportions of spirocyclic biscatechol monomer segments (e.g., A-A monomer segments according to Formula (A), Formula (B), Formula (C), and/or Formula (E)) and bridged bicyclic monomer segments (e.g., A-A monomer segments according to Formula (F) and/or Formula (G)). In some embodiments, for example, a polymer may contain spirocyclic biscatechol monomer segments A-A (A-A-1), bridged bicyclic monomer segments A-A (A-A-2), and monomer segments B-B, wherein the molar ratio [A-A-1]:[A-A-2]:[1B-B] is in the range of [1-10]:[0-10]:[1-10]. In some embodiments, the molar ratio [A-A-1]:[A-A-2]:[B-B] is in the range of [0-10]:[1-10]:[1-10]. In some embodiments, the molar ratio [A-A-1]:[A-A-2]:[B-B] is in the range of [1-5]:[0-5]:[1-3]. In some embodiments, the molar ratio [A-A-1]:[A-A-2]:[B-B] is in the range of [0-5]:[1-5]:[1-3]. In some embodiments, the molar ratio [A-A-1]:[A-A-2]:[B-B] is in the range of [1-3]:[0-1]:[2]. In any of these embodiments, the ratio {[A-A-1]+[A-A-2]}:[B-B] may be approximately 1:1. In any of these embodiments, the microporous polymer may have the structure:

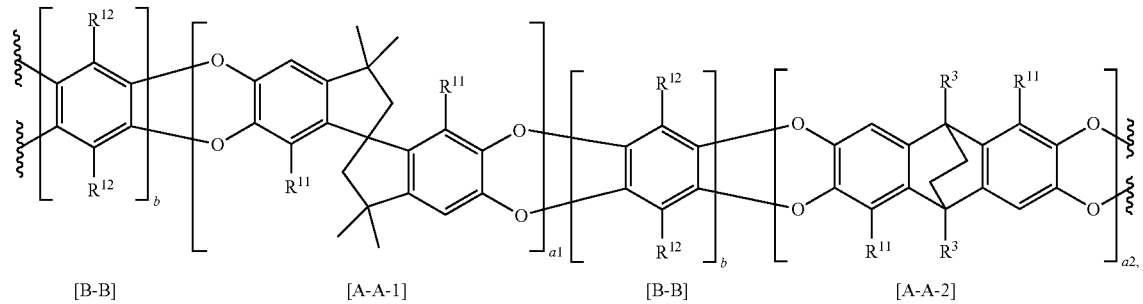

wherein the sum of subscripts a1, a2, and b ranges from 10-10,000. In some embodiments, the sum of subscripts a1, a2, and b ranges from 10-10,000, and the sum {a1+a2} is equal to the sum {b+b}. Such polymers may contain any combination of the R$^{11}$, R$^{12}$, R$^3$, groups set forth herein.

Also provided herein are methods for preparing microporous polymers as described herein. The methods include:

forming a polymerization mixture comprising (1) a plurality of A-A monomers, wherein each A-A monomer is independently a compound according to Formula (I), (II), (III), (IV). (V), (VI), (VII), or (VIII) of claim 23 or Formula (Ia), (IIa), (IIIa), (IVa), (Va), (Via), (VIIa), or (VIIIa) of claim 24,

(2) a plurality of B-B monomers, wherein each B-B monomer is independently a compound according to Formula (i), (ii), (iii), (iv), (v), (vi), (vii), or (viii):

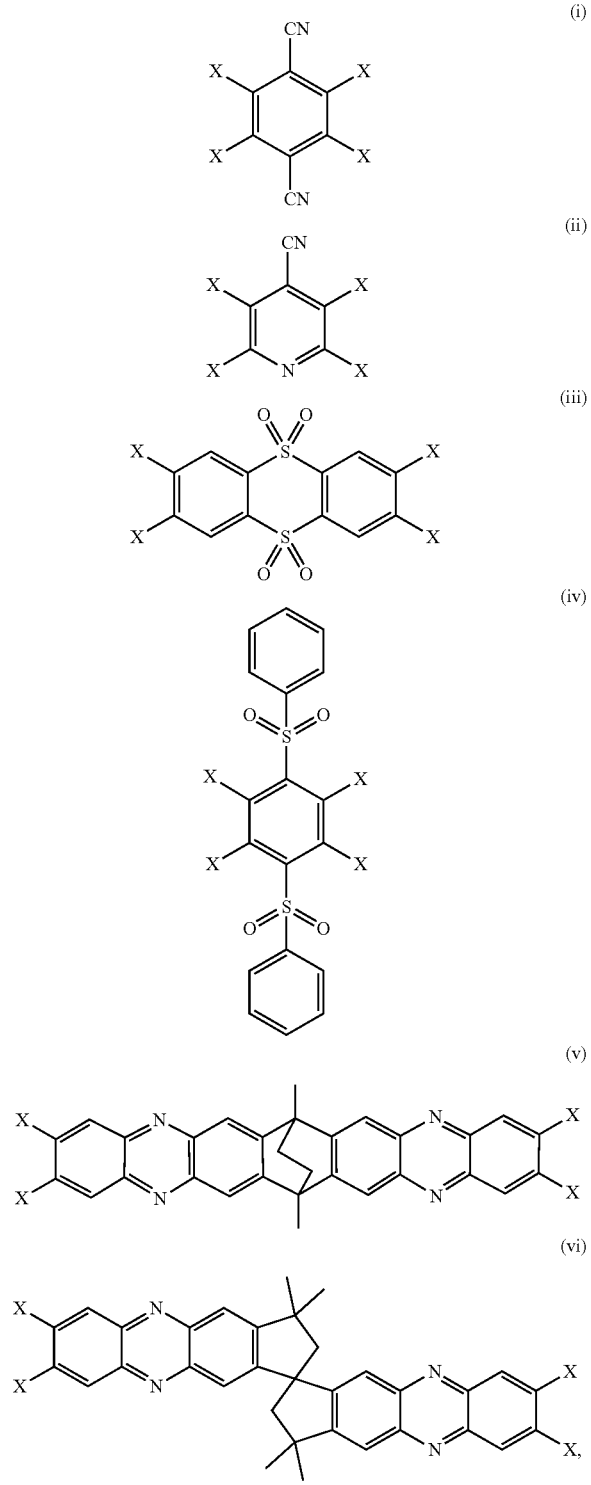

wherein X is a halide, and
(3) a base, and
heating the polymerization mixture, thereby forming the microporous polymer.

Any suitable organic base or an inorganic base may be utilized. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. In some embodiments, the polymerization mixture further comprises solid grinding media, liquid grinding media, or a combination thereof. In some embodiments, the methods further include shaking or rotating the polymerization mixture, e.g., in a shaking or rotating container, also called a ball mill.

In some embodiments, at least one monomer segment B-B in the microporous polymer is a monomer segment according to Formula (a-i) or Formula (b-i), and the method further comprises combining the microporous polymer with hydroxyl amine under conditions sufficient to form a modified microporous copolymer having at least one monomer segment B-B according to Formula (a-ii) or Formula (b-ii). In some embodiments, the methods further include heating the microporous polymer and the hydroxylamine.

In some embodiments, the methods further include combining the modified microporous copolymer with a base and an alkylating agent under conditions sufficient to form an alkylated microporous polymer having at least one monomer segment B-B according to Formula (a-iii), (b-iii), (a-iv), (b-iv), (a-v), (b-v), (a-vi), or (b-vi). Any suitable organic base or an inorganic base, including those described above and combinations thereof, may be used for the alkylation reaction. The alkylating agent may be, for example, may be, for example, a compound having the formula $R^{13}$-$R^{LG}$, wherein $R^{LG}$ is a leaving group such as a sulfonate or halide. $R^{LG}$ may be, for example, bromide, chloride, mesylate (methanesulfonate), triflate (trifluoromethanesulfonate), besylate (benzenesulfonate), tosylate (p-toluenesulfonate), and brosylate (4-bromobenzenesulfonate). In some embodiments, the alkylating agent is selected from the group consisting of dimethyl sulfate, diethyl sulfate, propane sultone, and butane sultone. In some embodiments, the methods further include heating the modified microporous copolymer, the base, and the alkylating agent.

In some embodiments, the alkylated microporous copolymer comprises at least one monomer segment B-B according to Formula (a-v), (b-v), (a-vi), or (b-vi); and the method further comprises combining the alkylated microporous polymer with a salt $A^+X^-$ under conditions sufficient to form a cation-exchanged microporous polymer, wherein the cation $A^+$ is a metal cation or an organic cation, and the anion $X^-$ is an organic anion or an inorganic anion. In some embodiments, $A^+$ is a tetraalkylammonium ion or a tetraalkylphosphonium ion. In some embodiments, $B^-$ is a halide (e.g., chloride, bromide, or iodide), a pseudohalogen (e.g., cyanide, isocyanide, or the like), or a bis(sulfonyl)imide (e.g., bis(trifluoromethyl-sulfonyl)imide) or the like.

In some embodiments, the methods further include combining the modified microporous copolymer with an acid and carbocation-generating compound to form an alkylated microporous polymer having at least one B-B segment according to Formula (a-vii), (b-vii), (a-iii), or (b-iii). In some embodiments, the acid is hydrochloric acid, formic acid, acetic acid, or trifluoroacetic acid. In some embodiments, the carbocation-generating compound is di-tert-butyl carbonate or camphene. In some embodiments, the methods further include heating the modified microporous copolymer, the acid, and the carbocation-generating compound.

IV. Microporous Polymer Membranes

Also provided herein are polymer membranes that contain one or more microporous polymers as described above.

Typically, thickness of the membranes will range from about 0.1 micrometers (μm) to about 5000 μm. Membrane thickness may range, for example, from about 0.1 μm to about 1000 μm, or from about 25 μm to about 500 μm, or from about 50 μm to about 150 μm. In some embodiments, at least one repeat unit of the membrane is crosslinked with a non-adjacent repeat unit by a crosslinker. Examples of crosslinkers include, but are not limited to, 2,6-bis(4-azidobenzylidene)cyclohexanone, oxygen, 2,6-bis(4-azidobenzylidene)-4-methylcyclohexanone, 2,6-bis(4-azidobenzylidene)-4-ethylcyclohexanone, 4-azidophenylsulfone, and combinations thereof.

In some embodiments, the membrane is in contact with a support material. The support material may contain one or more components such as a poly(arylether), a poly(arylether) copolymer, a poly(arylether sulfone) copolymer, polyethylene, a polyethylene copolymer, polypropylene, a polypropylene copolymer, polyacrylonitrle, a polyacrylonitrile copolymer, poly(vinylidene fluoride), poly(tetrafluoroethylene), poly(vinyl chloride), a poly(vinylchloride) copolymer, poly(hexafluoropropylene), a poly(hexafluoropropylene) copolymer, a polyaramide, a polyaramide copolymer, a porous metal, a porous alloyed metal, or a porous metal oxide.

Membranes may be prepared by suitable method. In some embodiments, the method of preparing the membrane includes casting at least one microporous polymer as described above from a solution or a dispersion of the polymer in a solvent or mixture of solvents, which are then substantially removed by evaporation to produce the membrane. In some embodiments, the method includes mixing the polymers in solvent with crosslinking agent before the solvent is evaporated and then exposing to ultraviolet radiation and/or heating to form a crosslinked membrane. In some embodiments, the method further includes the evaporation of solvent from the microporous polymer on a support to yield a supported membrane, which may be crosslinked or uncrosslinked.

V. Electrochemical Cells

Also provided herein are electrochemical cells cell comprising:
an anode;
an anode electrolyte in contact with anode;
a separator in contact with the anode electrolyte, wherein said separator comprises a membrane as described above, containing any of the microporous polymers described above or a combination thereof;
a cathode;
a cathode electrolyte in contact with separator; and
a cathode electrolyte in contact with cathode.

Examples of electrochemical cells in which microporous polymers according to the present disclosure include, but are not limited to, those described in US 2017/0222226 and US 2018/0085744. Microporous polymers according to the presence disclosure can be applied in conjunction with aqueous cell chemistries currently under investigation for redox-flow batteries, hybrid redox-flow batteries, redox-targeting batteries, and solar flow batteries, including metal coordination complexes, organometallics, polyoxometalates, redox-active organic molecules, and redoxmers.

The separator containing the microporous polymers described above allows the working ion(s) of the electrochemical cell to be passed through it. The separator allows for the shuttling of ions between the anode and the cathode, while preventing the transfer of electrons. The separator may optionally contain one or more support materials such as glass fiber separators.

The anode and the cathode can contain any suitable material. The anode, for example, may include or consist of zinc or lithium. The cathode, for example, may contain an active material such as sodium (2,2,6,6-tetramethylpiperidin-1-yl)oxyl-4-sulfate, a metal or metal oxide (e.g., a layered transition metal oxide such as $LiNi_xMn_yCo_zO_2$, referred to as NMC), and/or an electrolyte. The electrochemical cell may be a $Zn-O_2$ cell, $Zn-MnO_2$ cell, or a Zn-MOF cell.

The electrodes can be a solid or non-solid form. In some embodiments, the cathode or the anode is flowable. That is, in some embodiments, the electrode may be substantially fluid and/or easily deformed prior to first use and/or when substantially fully charged. For example, in some embodiments, the electrode may have a measurable viscosity, and/or the electrode may tend to flow and to conform to the outline of its container, and/or the electrode may have the consistency of a paste. In some cases, the flowable electrode, after being left undisturbed for a day or less, may be observably deformed from its original shape, and in some cases, such observable deformations may occur on the time scale of minutes or seconds.

The electrolytes can include any suitable component. For example, the electrolytes can include a metal salt. Examples of suitable metal salts include, but are not limited to, bis(trifluoromethane)sulfonimide lithium salt (LiTFSI), lithium triflate ($LiCF_3SO_3$), sodium triflate ($NaCF_3SO_3$), lithium perchlorate ($LiClO_4$), sodium perchlorate ($NaClO_4$), lithium hexafluorophosphate ($LiPF_6$), sodium hexafluorophosphate ($NaPF_6$), lithium tetrafluoroborate ($LiBF_4$), and/or sodium tetrafluoroborate ($NaBF_4$). In some embodiments, the molar concentration of the metal salt in the cathode composition is at least about 0.1 M, at least about 0.2 M, at least about 0.5 M (and/or, in certain embodiments, up to about 1 M, or more).

The metal salt can include any suitable metal as the cation, or any suitable anion. For example, the metal can be any alkali metal, alkali earth metal or transition metal. In some embodiments the metal can be an alkali metal. In some embodiments, the metal cation can be lithium or sodium. In some embodiments, the metal cation can be lithium.

The anion of the metal salt can be any suitable anion. In some embodiments, anion of the metal salt can be bis(trifluoromethyl)sulfonimide, trifluoromethylsulfonate, fluorosulfonimide, perchlorate, tetrafluoroborate, hexafluorophosphate, nitrate, fluoride, chloride, bromide, or iodide. In some embodiments, the metal salt can be lithium bis(trifluoromethyl)sulfonimide, lithium nitrate, or combinations thereof.

The electrolytes can include a solvent, an ionic liquid, a cation, an anion, or combinations thereof. Representative solvents include, but are not limited to, tetraethylene glycol dimethyl ether (TEGDME), dimethoxyethane (DME), diglyme, triglyme, dioxolane (DOL), tetrahydrofuran (THF), methyl-tetrahydrofuran (methyl-THF), ethyl methyl sulfone (EMS), propyl methyl sulfone (PMS), and gamma-butyrolactone (GBL). In some embodiments, the electrolytes can include at least one of diglyme, PGMEA, dimethoxyethane, triglyme, tetraglyme, dioxolane, THF, propylene carbonate, dimethylcarbonate, ethylene carbonate, ethyl methyl sulfone (EMS), propyl methyl sulfone (PMS), water, poly(ethylene oxide) and copolymers thereof, dimethylsulfoxide, N-methylpyrrolidinone, or acetonitrile. In some embodiments, the electrolytes includes diglyme.

VI. EXAMPLES

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

Lacking has been the availability of monomers with functional groups presented in well-defined arrangements from which functional microporous polymers are synthesized and manufactured as a selective membrane with well-defined pore size and functionality. Owing to the highly symmetrical structure of typical monomers (e.g. bis-catechols), synthetic methods need to be developed to access monomers with specific number and spatial arrangements of target functional groups. Moreover, PIMs modified with functional groups originating from the electrophilic monomer and along the polymer backbone have not yielded solution-processable materials for preparing membranes, with only one exception noted previously for amidoxime-based PIMs. Needed are functional nucleophilic monomers from which to prepare soluble polymers for casting membranes with tailored properties for use in selective separations and other devices. Furthermore, it is highly desirable to have access to structural variants of functional monomers of the same class so that membranes comprising them can fine-tune their transport selectivity. e.g., on the basis of size or other physio-chemical interactions with analytes in the system. Furthermore, it is highly desirable to tailor the backbone chemistry with functional nucleophilic monomers in stride with the electrophilic monomers, e.g., using highly efficacious chemical reactions targeted to the electrophilic monomers after they have been incorporated into the polymer chain (i.e., post-polymerization reactions). Prior understanding of the chemical reactivity of functional groups originating from the electrophilic monomer (i.e., 1,4-dicyanoarene functionality) has been limited to only a few reactions, and those known are substantially ineffective. Needed are chemical reactions that interconvert backbone chemical functionality to deterministic outcomes (i.e., complete, or substantially complete chemical transformations). Such chemical transformations should yield polymers with substantial solubility in suitable solvents for casting, and in turn, provide membranes for use in a variety of contexts, including gas separations, pervaporation, electrowinning, fuel cells, batteries and other electrochemical cells, photoelectrochemical cells, etc.

Analytical Methods $^1$H and $^{13}$C Nuclear Magnetic Resonance (NMR) Spectroscopy. $^1$H and $^{13}$C NMR spectra were recorded on Bruker Avance II at 500 MHz and 125 MHz, respectively. Chemical shifts are reported in δ (ppm) relative to the residual solvent peak (CDCl$_3$: 7.26 for $^1$H, 77.16 for $^{13}$C; d$_6$-DMSO: 2.50 for $^1$H, 39.51 for $^{11}$C; d$_4$-o-C$_6$D$_4$Cl$_2$, 120° C.: 7.22 and 6.95 for $^1$H). Splitting patterns are designated as s (singlet), br s (broad singlet), d (doublet), t (triplet), q (quartet), and m (multiplet).

Electrospray Ionization Mass Spectrometry (ESI-MS). Spectra for 3-6 were acquired on a Synapt G2 Q-TOF spectrometer. Spectra for 7-10 were acquired on a Bruker MicroTOF spectrometer.

Elemental Analysis (EA). EA was performed as a fee-for-service by the University of California, Berkeley College of Chemistry Microanalytical Facility.

Single-Crystal X-ray Diffraction (XRD). Single crystals for 3-7, 9, and 10 were selected and mounted on Mitegen® loops with Paratone oil and placed in an Oxford Cryosystems Cryostream 700 plus at T=100 K. Data were collected for 3-5 using a Bruker D8 diffractometer with APEXII CCD detector, with Mo K$_\alpha$ (λ=0.71073 Å), while for 6, 7, 9, and 10 using beamline 12.2.1 at the Advanced Light Source with λ=0.7288 Å using a Bruker D8 diffractometer with a Bruker PHOTONII CPAD detector. Data reduction was performed and corrected for Lorentz and polarization effects using SAINT v8.38a and were corrected for absorption effects using SADABS v2016/2. Structure solutions were performed by SHELXT using the direct method and were refined by least-square refinement against F$^2$ by SHELXL.

Size-Exclusion Chromatography (SEC). SEC using THF as the mobile phase was carried out with a Malvern Viscotek TDA 302 system calibrated with a 99 kDa monodisperse polystyrene standard. SEC using DMF (containing 0.2% w/v LiBr) as the mobile phase was carried out using a customized system consisting of a Shimadzu LC-20AD pump, Viscotek VE 3580 refractive index detector, and two mixed bed columns connected in series (Viscotek GMHHR-M). The system was operated at a temperature of 70° C. Calibration on the system was performed with narrow poly(methyl methacrylate) standards (Polymer Laboratories) ranging from 620 g mol$^{-1}$ to 910,500 g mol$^{-1}$.

Gas Absorption and Desorption. N$_2$ adsorption isotherms were collected at 77 K on a Micromeritics Tristar II 3020 gas sorption analyzer. CO$_2$ adsorption isotherms were collected on a Micromeritics ASAP 2020 gas sorption analyzer at 273 K. Nonlocal DFT (NLDFT) pore-size distributions from N$_2$ adsorption isotherms were calculated using SAIEUS software provided by Micromeritics using the 2D Heterogeneous Surface model. NLDFT pore-size distributions from CO$_2$ adsorption isotherms were calculated using the Micromeritics Carbon Slit model with high regularization. Samples were degassed under vacuum at 100-150° C. overnight prior to analysis.

Example 1. Monomer Synthesis

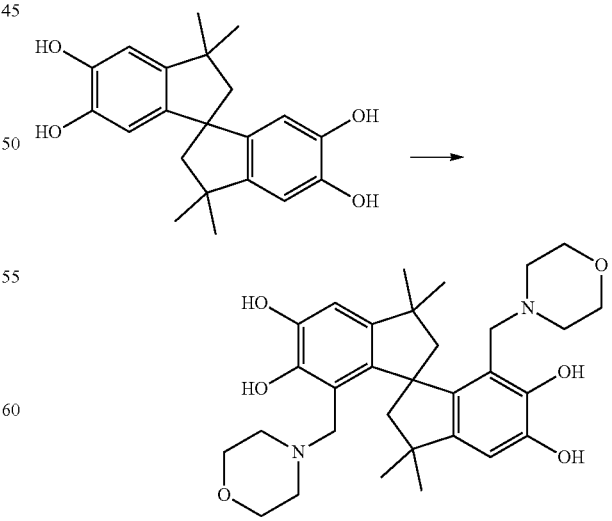

1-1

1-1: To a 500 mL round bottom flask was added ethanol (250 mL), paraformaldehyde (4.45 g, 156 mmol), and morpholine (13 mL, 156 mmol). The reaction was stirred for 10 min at 70° C. which point 3,3,3',3'-tetramethyl-1,1'-spirobisindane-5,5',6,6'-tetraol (10 g, 30 mmol) was added and the reaction was stirred at reflux overnight. 500 mL of hexanes was then added to the mixture and the it was cooled to 4° C. The precipitate was filtered and washed with hexanes and tried to give 6.1 g of 1-1 (36%) as a white solid. $^1$H NMR (CDCl$_3$, 500 MHz): δ (ppm) 6.70 (s, 2H), 3.18 (d, 2H, J=14.6 Hz), 3.08 (d, 2H, J=14.6 Hz), 2.31 (d, 2H, J=13.4 Hz), 2.18 (d, 2H, J=13.4 Hz), 1.65 (br s, 16H), 1.38 (s, 6H), 1.30 (s, 6H); $^{13}$C{$^1$H} NMR (CDCl$_3$, 125 MHz): δ (ppm) 145.91, 145.16, 141.75, 138.26, 116.00, 108.75, 66.51, 57.86, 56.73, 55.90, 52.86, 42.53, 33.21, 30.05: HR-MS (m/z) [M+H]$^+$: Calculated: 539.3116, Found: 539.3117: Elemental Analysis for C$_{31}$H$_{42}$N$_2$O$_6$ Calculated: C 69.12, H 7.86, N 5.20; Found: C 69.14, H 7.97, N 5.11; see FIG. 3 for X-ray crystallography structure.

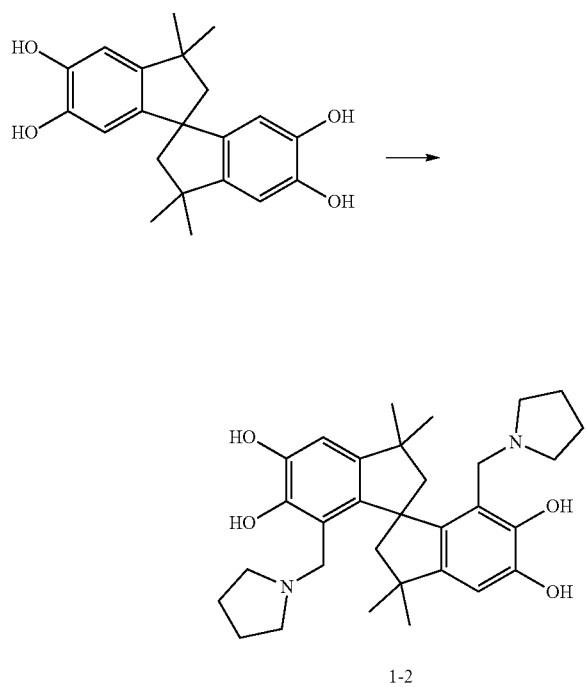

1-2: To a 500 mL round bottom flask was added ethanol (250 mL), paraformaldehyde (4.45 g, 156 mmol), and pyrrolidine (10 mL, 156 mmol). The reaction was stirred for 10 minutes at 70° C. which point 3,3,3',3'-tetramethyl-1,1'-spirobisindane-5,5',6,6'-tetraol 10 g (30.2 mmol) was added and the reaction was stirred at reflux overnight. The reaction was concentrated by rotary evaporator and product was recrystallized from methylene chloride/hexanes to give 11.5 g of 1-2 (70%) as a pale white solid. $^1$H NMR (CDCl$_3$, 500 MHz): δ (ppm) 6.60 (s, 2H), 3.27 (d, 4H, J=5.6 Hz), 2.27 (d, 2H, J=13.4 Hz), 2.20 (d, 2H, J=13.4 Hz), 1.78 (br s, 16H), 1.34 (s, 6H), 1.29 (s, 6H); $^{13}$C{$^1$H} NMR (CDCl$_3$, 125 MHz): δ (ppm) 145.43, 144.28, 141.62, 137.92, 116.30, 106.76, 57.89, 56.71, 53.48, 53.24, 42.73, 32.83, 28.83, 23.45; HR-MS (m/z) [M+H]$^+$: Calculated: 503.2904, Found: 503.2905: Elemental Analysis for C$_{31}$H$_{42}$N$_2$O$_4$ Calculated: C 73.49, H 8.36, N 5.53; Found: C 73.31, H 8.33, N 5.69; see FIG. 2 for X-ray crystallography structure.

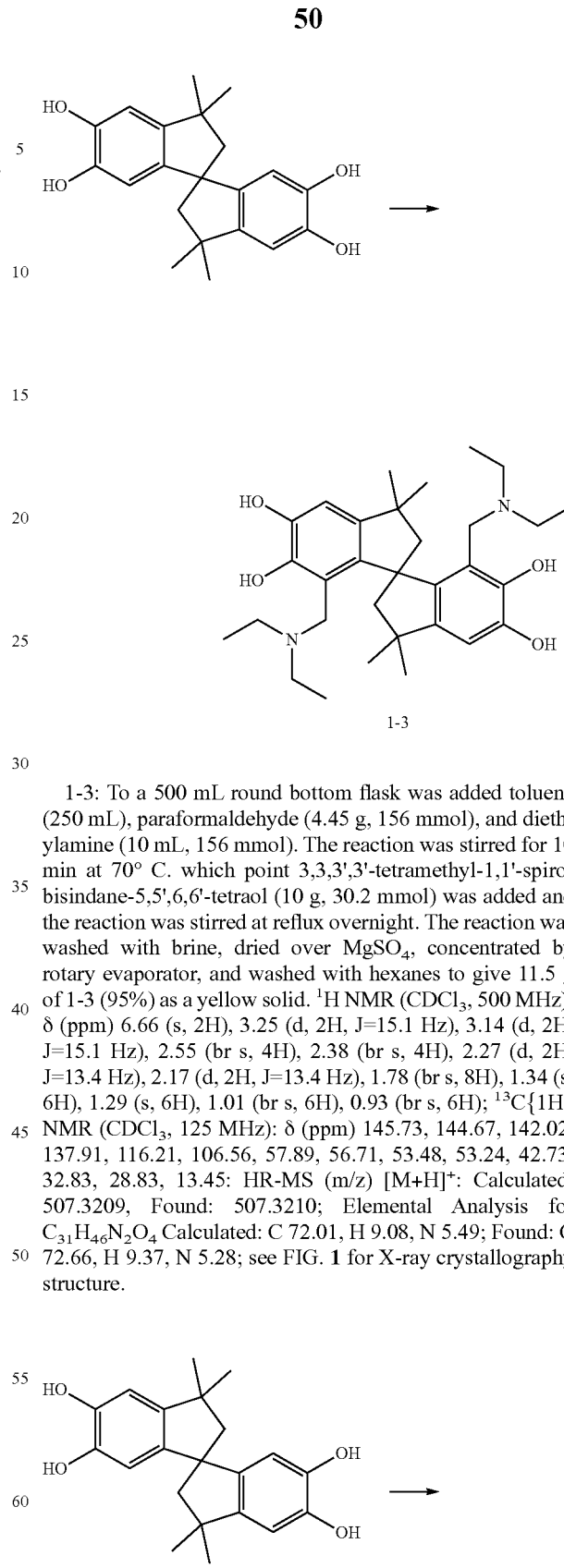

1-3: To a 500 mL round bottom flask was added toluene (250 mL), paraformaldehyde (4.45 g, 156 mmol), and diethylamine (10 mL, 156 mmol). The reaction was stirred for 10 min at 70° C. which point 3,3,3',3'-tetramethyl-1,1'-spirobisindane-5,5',6,6'-tetraol (10 g, 30.2 mmol) was added and the reaction was stirred at reflux overnight. The reaction was washed with brine, dried over MgSO$_4$, concentrated by rotary evaporator, and washed with hexanes to give 11.5 g of 1-3 (95%) as a yellow solid. $^1$H NMR (CDCl$_3$, 500 MHz): δ (ppm) 6.66 (s, 2H), 3.25 (d, 2H, J=15.1 Hz), 3.14 (d, 2H, J=15.1 Hz), 2.55 (br s, 4H), 2.38 (br s, 4H), 2.27 (d, 2H, J=13.4 Hz), 2.17 (d, 2H, J=13.4 Hz), 1.78 (br s, 8H), 1.34 (s, 6H), 1.29 (s, 6H), 1.01 (br s, 6H), 0.93 (br s, 6H); $^{13}$C{$^1$H} NMR (CDCl$_3$, 125 MHz): δ (ppm) 145.73, 144.67, 142.02, 137.91, 116.21, 106.56, 57.89, 56.71, 53.48, 53.24, 42.73, 32.83, 28.83, 13.45: HR-MS (m/z) [M+H]$^+$: Calculated: 507.3209, Found: 507.3210; Elemental Analysis for C$_{31}$H$_{46}$N$_2$O$_4$ Calculated: C 72.01, H 9.08, N 5.49; Found: C 72.66, H 9.37, N 5.28; see FIG. 1 for X-ray crystallography structure.

-continued

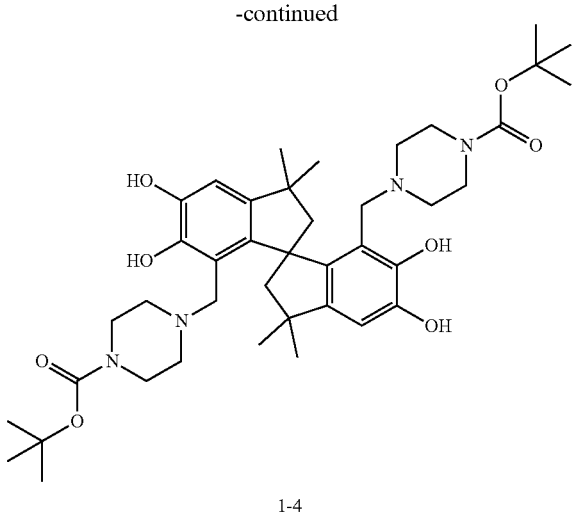

1-4

1-4: To a 500 mL round bottom flask was added toluene (250 mL), paraformaldehyde (4.45 g, 156 mmol) and diethylamine (10 mL, 156 mmol). The reaction was stirred for 10 min at 70° C., at which point 3,3,3',3'-tetramethyl-1,1'-spirobisindane-5,5',6,6'-tetraol (10 g, 30.2 mmol) was added and the reaction was stirred at reflux overnight. The reaction was washed with brine, dried over MgSO$_4$, concentrated by rotary evaporator and sonicated in hexanes to give 14.7 g of 1-4 (98%) as a white solid. $^1$H NMR (CDCl$_3$, 500 MHz): δ (ppm) 6.68 (s, 2H), 3.15 (d, 2H, J=15.0 Hz), 3.11 (d, 2H, J=15.0 Hz), 2.31 (d, 2H, J=13.1 Hz), 2.16 (d, 2H, J=13.1 Hz), 1.46 (s, 18H), 1.36 (s, 6H), 1.29 (s, 6H); $^{13}$C{$^1$H}NMR (CDCl$_3$, 125 MHz): δ (ppm) 146.34, 145.16, 141.75, 138.26, 116.00, 108.75, 66.51, 57.86, 57.65, 54.93, 51.43, 44.63, 32.21, 30.15 28.41; HR-MS (m/z) [M+H]$^+$: Calculated: 537.4482, Found: 737.4484; Elemental Analysis for C$_{41}$H$_{60}$N$_4$O$_8$ Calculated: C 66.82, H 8.21, N 7.60; Found: C 67.11, H 8.11, N 7.22; see FIG. 5 for X-ray crystallography structure.

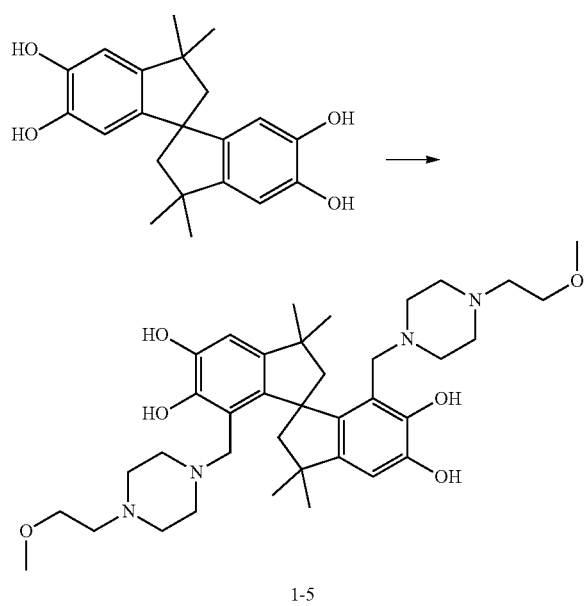

1-5

1-5: To a 500 mL round bottom flask was added toluene (250 mL), paraformaldehyde (4.45 g, 156 mmol), and diethylamine (10 mL, 156 mmol). The reaction was stirred for 10 min at 70° C. which point 3,3,3',3'-tetramethyl-1,1'-spirobisindane-5,5',6,6'-tetraol (10 g, 30.2 mmol) was added and the reaction was stirred at reflux overnight. The reaction was concentrated by rotary evaporator and triturated with hexanes to give 11.5 g of 1-5 (95%) as a yellow solid. $^1$H NMR (CDCl$_3$, 500 MHz): δ (ppm) 6.65 (s, 2H), 3.48 (t, 4H, J=5.5 Hz) 3.37 (d, 4H, J=3.3 Hz), 3.34 (s, 6H), 2.57 (t, 4H, J=3.4 Hz), 2.27 (d, 2H, J=13.4 Hz), 2.20 (d, 2H, J=13.4 Hz), 1.34 (s, 6H), 1.29 (s, 6H)$^{13}$C{$^1$H} NMR (CDCl$_3$, 125 MHz): δ (ppm) 146.11, 145.97, 140.35, 136.76, 116.00, 109.33, 69.94 66.51, 60.23 57.86, 56.73, 55.90, 52.86, 51.10 42.53, 33.21, 30.05; HR-MS (m/z) [M+H]$^+$: Calculated: 653.4273, Found: 653.4271; Elemental Analysis for C$_{37}$H$_{56}$N$_4$O$_6$ Calculated: C 68.07, H 8.65, N 8.58; Found: C 67.83, H 8.79, N 8.59; see FIG. 4 for X-ray crystallography structure.

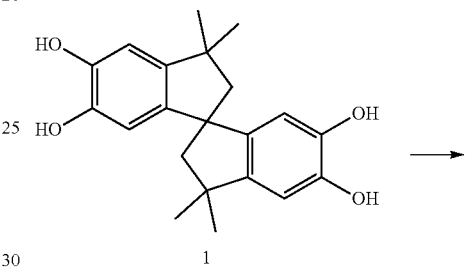

1

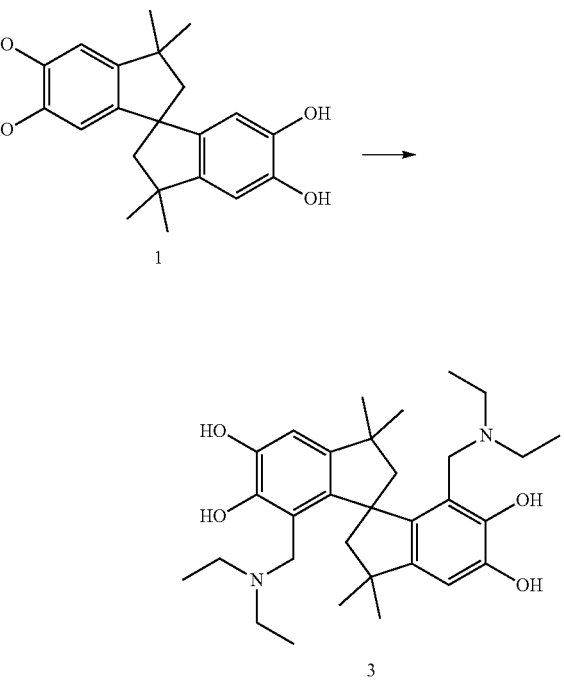

3

Synthesis of 3: To a 500 mL round bottom flask was added toluene (250 mL), paraformaldehyde (4.45 g, 156 mmol), and diethylamine (10 mL, 156 mmol). The reaction was stirred for 10 min at 70° C. which point 3,3,3',3'-tetramethyl-1,1'-spirobisindane-5,5',6,6'-tetraol (10 g, 30.2 mmol) was added and the reaction was stirred at reflux overnight. The reaction was washed with brine, dried over MgSO$_4$, concentrated by rotary evaporator, and washed with hexanes to give 11.5 g of 3 (95%) as a yellow solid. $^1$H NMR (CDCl$_3$, 500 MHz): δ (ppm) 6.66 (s, 2H), 3.25 (d, 2H, J=15.1 Hz), 3.14 (d, 2H, J=15.1 Hz), 2.55 (br s, 4H), 2.38 (br s, 4H), 2.27 (d, 2H, J=13.4 Hz), 2.17 (d, 2H, J=13.4 Hz), 1.34 (s, 6H), 1.29 (s, 6H), 1.01 (br s, 6H), 0.93 (br s, 6H); $^{13}$C (1H) NMR (CDCl$_3$, 125 MHz): δ (ppm) 145.73, 144.67, 142.02, 137.91, 116.21, 106.56, 57.89, 56.71, 53.48, 53.24, 42.73, 32.83, 28.83, 13.45; HR-MS (m/z) [M+H]$^+$: Calculated: 507.3209, Found: 507.3210; Elemental Analysis for C$_{31}$H$_{46}$N$_2$O$_4$ Calculated: C 72.01, H 9.08, N 5.49; Found: C 72.66, H 9.37, N 5.28. The single-crystal x-ray structure of 3 is shown in FIG. 1.

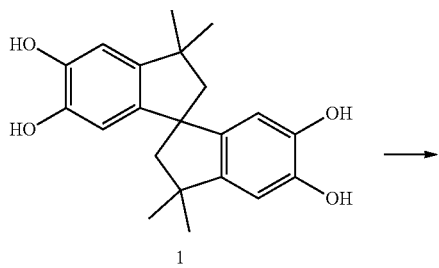

1

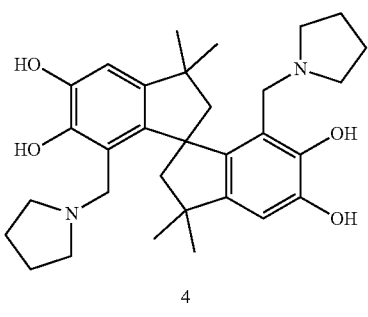

4

Figure 2:
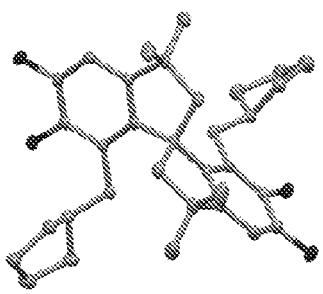
FIG. 2 shows the X-ray crystallography structure of amine-functionalized monomer 4.

Synthesis of 4: To a 500 mL round bottom flask was added ethanol (250 mL), paraformaldehyde (4.45 g, 156 mmol), and pyrrolidine (10 mL, 156 mmol). The reaction was stirred for 10 min at 70° C. which point 3,3,3',3'-tetramethyl-1,1'-spirobisindane-5,5',6,6'-tetraol 10 g (30.2 mmol) was added and the reaction was stirred at reflux overnight. The reaction was concentrated by rotary evaporator and product was recrystallized from methylene chloride/hexanes to give 11.5 g of 4 (70%) as a pale white solid. $^1$H NMR (CDCl$_3$, 500 MHz): δ (ppm) 6.60 (s, 2H), 3.27 (d, 4H, J=5.6 Hz), 2.27 (d, 2H, J=13.4 Hz), 2.20 (d, 2H, J=13.4 Hz). 1.78 (br s, 16H), 1.34 (s, 6H), 1.29 (s, 6H); $^{13}$C{$^1$H} NMR (CDCl$_3$, 125 MHz): δ (ppm) 145.43, 144.28, 141.62, 137.92, 116.30, 106.76, 57.89, 56.71, 53.48, 53.24, 42.73, 32.83, 28.83, 23.45; HR-MS (m/z) [M+H]$^+$: Calculated: 503.2904, Found: 503.2905; Elemental Analysis for C$_{31}$H$_{42}$N$_2$O$_4$ Calculated: C 73.49, H 8.36, N 5.53; Found: C 73.31. H 8.33, N 5.69. The single-crystal x-ray structure of 4 is shown in FIG. 2.

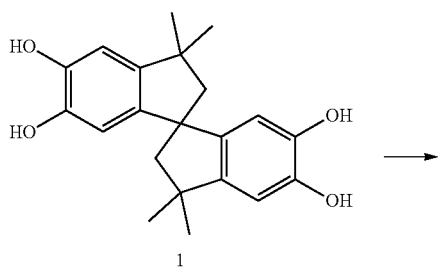

1

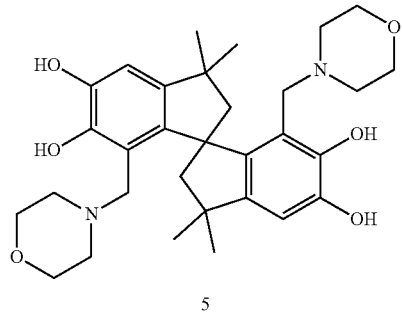

5

Figure 3:
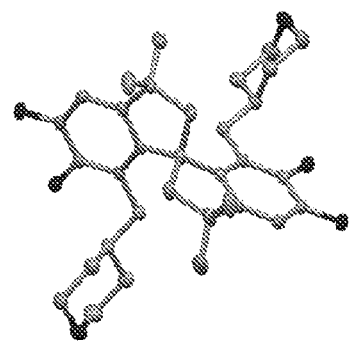
FIG. 3 shows the X-ray crystallography structure of amine-functionalized monomer 5.

Synthesis of 5: To a 500 mL round bottom flask was added ethanol (250 mL), paraformaldehyde (4.45 g, 156 mmol), and morpholine (13 mL, 156 mmol). The reaction was stirred for 10 min at 70° C. which point 3,3,3',3'-tetramethyl-1,1'-spirobisindane-5,5',6,6'-tetraol (10 g, 30 mmol) was added and the reaction was stirred at reflux overnight. 500 mL of hexanes was then added to the mixture and the it was cooled to 4° C. The precipitate was filtered and washed with hexanes and tried to give 6.1 g of 5 (36%) as a white solid. $^1$H NMR (CDCl$_3$, 500 MHz): δ (ppm) 6.70 (s, 2H), 3.18 (d, 2H, J=14.6 Hz), 3.08 (d, 2H, J=14.6 Hz), 2.31 (d, 2H, J=13.4 Hz), 2.18 (d, 2H, J=13.4 Hz), 1.65 (br s, 16H), 1.38 (s, 6H), 1.30 (s, 6H); $^{13}$C{$^1$H} NMR (CDCl$_3$, 125 MHz): δ (ppm) 145.91, 145.16, 141.75, 138.26, 116.00, 108.75, 66.51, 57.86, 56.73, 55.90, 52.86, 42.53, 33.21, 30.05; HR-MS (m/z) [M+H]$^+$: Calculated: 539.3116, Found: 539.3117; Elemental Analysis for C$_{31}$H$_{42}$N$_2$O$_6$ Calculated: C 69.12, H 7.86, N 5.20; Found: C 69.14, H 7.97, N 5.11. The single-crystal x-ray structure of 5 is shown in FIG. 3.

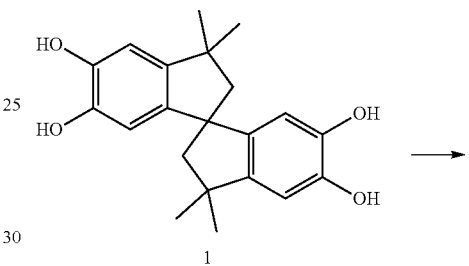

1

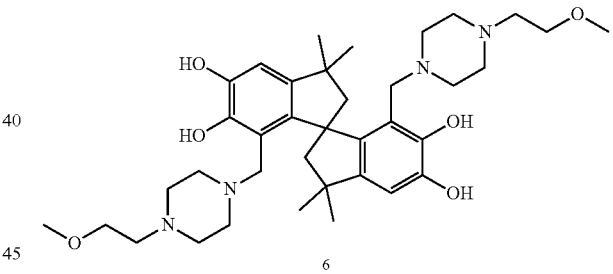

6

Figure 4:
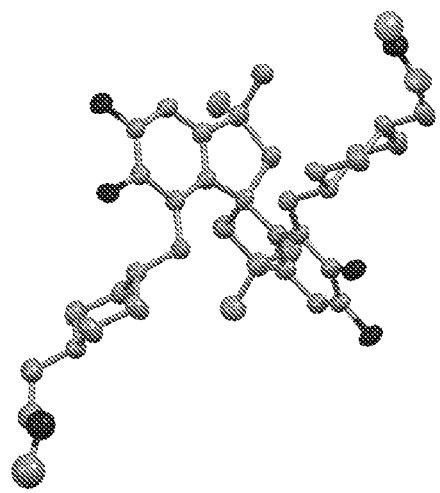
FIG. 4 shows the X-ray crystallography structure of amine-functionalized monomer 6.

Synthesis of 6: To a round bottom flask was added toluene (250 mL), paraformaldehyde (4.45 g, 156 mmol), and 2-methoxyethyl-piperazine (10 mL, 156 mmol). The reaction was stirred for 10 min at 70° C. which point 3,3,3',3'-tetramethyl-1,1'-spirobisindane-5,5',6,6'-tetraol (10 g, 30.2 mmol) was added and the reaction was stirred at reflux overnight. The reaction was concentrated by rotary evaporator and triturated with hexanes to give 11.5 g of 6 (95%) as a yellow solid. $^1$H NMR (CDCl$_3$, 500 MHz): δ (ppm) 6.65 (s, 2H), 3.48 (t, 4H, J=5.5 Hz), 3.34 (s, 6H), 3.19 (d, 2H, J=14.8 Hz), 3.10 (d, 2H, J=14.8 Hz), 2.57 (t, 4H, J=5.5 Hz), 2.25 (d, 2H, J=13.4 Hz), 2.12 (d, 2H, J=13.4 Hz), 1.34 (s, 6H), 1.29 (s, 6H); $^{13}$C{$^1$H} NMR (CDCl$_3$, 125 MHz): δ (ppm) 146.11, 145.97, 140.35, 136.76, 116.00, 109.33, 69.94 66.51, 60.23 57.86, 56.73, 55.90, 52.86, 51.10 42.53, 33.21, 30.05; HR-MS (m/z) [M+H]$^+$: Calculated: 653.4273, Found: 653.4271; Elemental Analysis for C$_{37}$H$_{56}$N$_4$O$_6$ Calculated: C 68.07, H 8.65, N 8.58; Found: C 67.83, H 8.79, N 8.59. The single-crystal x-ray structure of 6 is shown in FIG. 4.

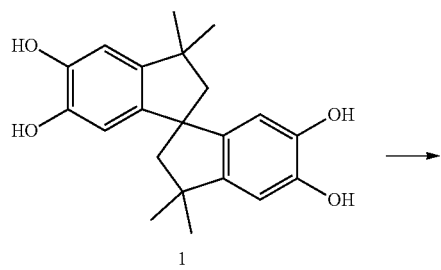

1

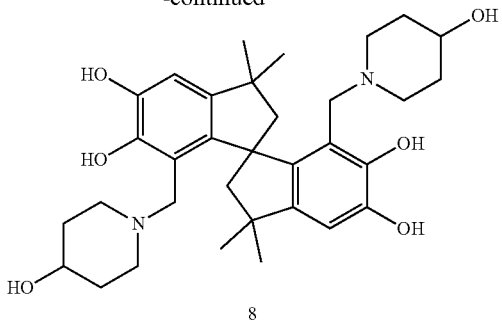

8

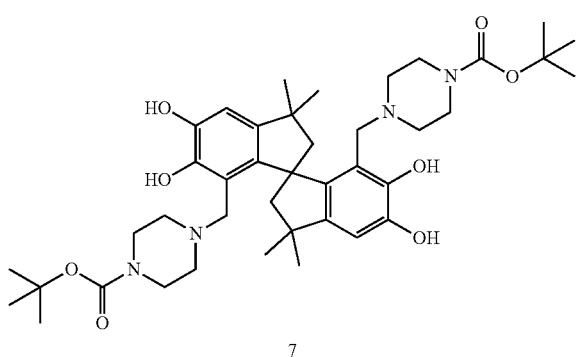

7

Figure 5:
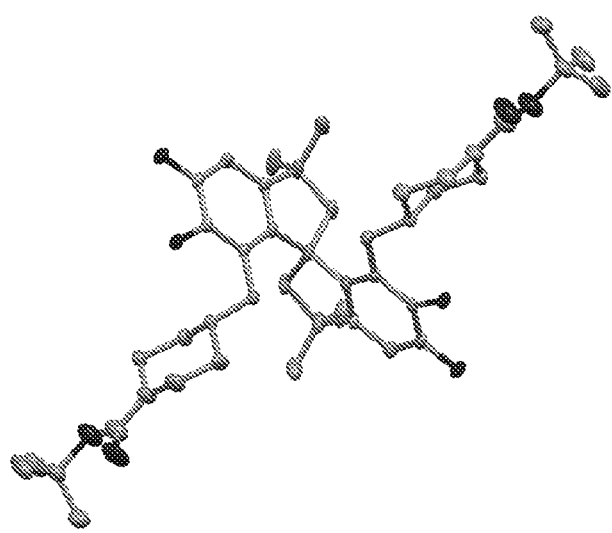
FIG. 5 shows the X-ray crystallography structure of amine-functionalized monomer 7.

Synthesis of 7: To a round bottom flask was added toluene (250 mL), paraformaldehyde (4.45 g, 156 mmol) and Boc-Piperazine (10 mL, 156 mmol). The reaction was stirred for 10 min at 70° C., at which point 3,3,3',3'-tetramethyl-1,1'-spirobisindane-5,5',6,6'-tetraol (10 g, 30.2 mmol) was added and the reaction was stirred at reflux overnight. The reaction was washed with brine, dried over MgSO$_4$, concentrated by rotary evaporator and sonicated in hexanes to give 14.7 g of 7 (98%) as a white solid. $^1$H NMR (CDCl$_3$, 500 MHz): δ (ppm) 6.68 (s, 2H), 3.15 (d, 4H, J=15.0 Hz), 3.11 (d, 4H, J=15.0 Hz), 2.31 (d, 4H, J=13.1 Hz), 2.16 (d, 2H, J=13.1 Hz), 1.46 (s, 18H), 1.36 (s, 6H), 1.29 (s, 6H); $^{13}$C{$^1$H} NMR (CDCl$_3$, 125 MHz): δ (ppm) 146.34, 145.16, 141.75, 138.26, 116.00, 108.75, 66.51, 57.86, 57.65, 54.93, 51.43, 44.63, 32.21, 30.15 28.41; HR-MS (m/z) [M+H]$^+$: Calculated: 737.4484, Found: 737.4307; Elemental Analysis for C$_{41}$H$_{60}$N$_4$O$_8$ Calculated: C 66.82, H 8.21, N 7.60; Found: C 67.11, H 8.11, N 7.22. The single-crystal x-ray structure of 7 is shown in FIG. 5.

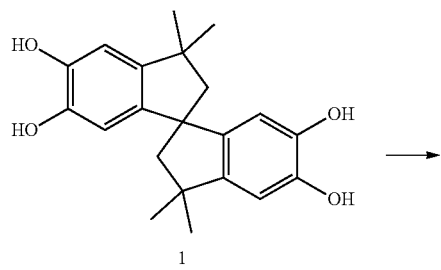

1

Synthesis of 8: To a round bottom flask was added ethanol (250 mL), paraformaldehyde (4.4 mg, 147 mmol) and 4-hydroxypiperidine (15.1 g, 150 mmol). The reaction was stirred for 15 min at 70° C., at which point 3,3,3',3'-tetramethyl-1,1'-spirobisindane-5,5',6,6'-tetraol (10 g, 29.4 mmol) was added and the reaction was stirred at reflux overnight. The reaction was washed with brine, dried over MgSO$_4$, concentrated by rotary evaporator and sonicated in hexanes to give 8.3 g of 8 (50%) as a white solid. $^1$H NMR (DMSO-d$_6$, 500 MHz): δ (ppm) 6.46 (br s, 2H), 4.63 (br s, 2H), 4.38 (t, 2H, J=5.4 Hz), 3.44 (t, 2H, J=5.4 Hz), 2.15 (d, 2H, 13.1 Hz), 2.07 (d, 2H, 13.1 Hz), 1.67 (br s, 4H), 1.28 (br s, 6H), 1.18 (br s, 6H). $^{13}$C{$^1$H} NMR (DMSO-d$_6$, 125 MHz): δ (ppm): 146.43, 145.11, 141.25, 137.99, 116.40, 108.56, 57.78, 56.69, 42.46, 33.17, 30.28: HR-MS (m/z) [M+H]$^+$: Calculated: 567.3429, Found: 567.3292; Elemental Analysis for C$_{41}$H$_{60}$N$_4$O$_8$ Calculated: C 66.82, H 8.21, N 7.60; Found: C 67.11, H 8.11, N 7.22.

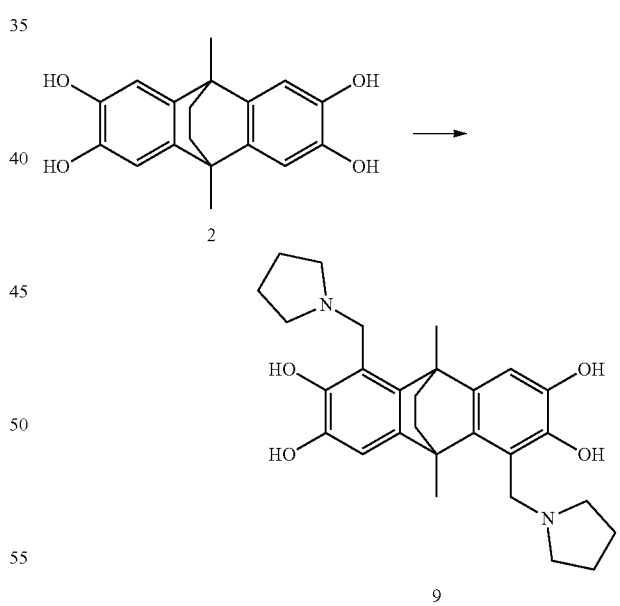

Synthesis of 9: To a sealable reaction vial was added toluene (12.5 mL), paraformaldehyde (500 mg, 16.65 mmol), pyrrolidine (1.40 mL, 16.76 mmol), and 9,10-dimethyl-9,10-dihydro-9,10-ethanoanthracene-2,3,6,7-tetraol (500 mg, 1.68 mmol). After sealing, the vial was heated for 8 h at 120° C. while stirring. The reaction mixture was subsequently concentrated in vacuo, prior to the addition of hexanes (50 mL) to precipitate the product. The product was isolated by filtration and washed with ethanol (50 mL) to give 9 as a pale pink solid (219 mg) in 28% yield after drying. $^1$H NMR (CDCl$_3$, 500 MHz): δ (ppm) 6.85 (s, 2H), 4.31 (d, 2H, J=14.1 Hz), 4.26 (d, 2H, J=14.1 Hz), 2.67 (br s, 8H), 2.03 (s, 6H), 1.85 (br s, 12H), 1.74 (s, 2H), 1.44 (s, 2H); $^{13}$C{$^1$H} NMR (CDCl$_3$, 125 MHz): δ (ppm) 143.98, 141.54, 139.71, 134.57, 117.90, 107.40, 54.77, 53.29, 43.94, 38.27, 27.04, 23.78; HR-MS (m/z) [M+H]$^+$: Calculated: 507.3217, Found: 507.3105.

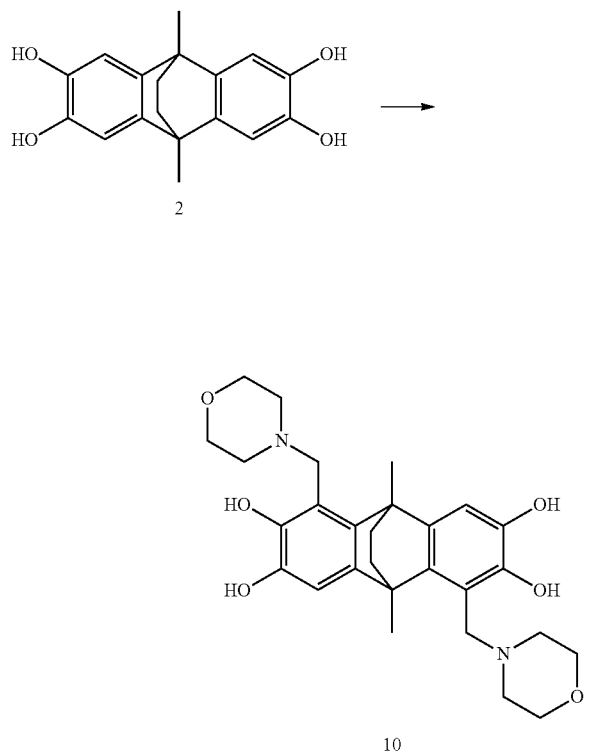

Synthesis of 10: To a sealable reaction vial was added toluene (12.5 ml), paraformaldehyde (500 mg, 16.65 mmol), morpholine (1.45 mL, 16.76 mmol), and 9,10-dimethyl-9,10-dihydro-9,10-ethanoanthracene-2,3,6,7-tetraol (500 mg, 1.68 mmol). After sealing, the vial was heated for 8 h at 120° C. while stirring. The reaction mixture was subsequently concentrated in vacuo, prior to the addition of hexanes (50 mL) to precipitate the product. The product was isolated by filtration and washed with ethanol (50 mL) to give 10 as an off-white solid (521 mg) in 63% yield after drying. $^1$H NMR (CDCl$_3$, 500 MHz): δ (ppm) 6.87 (s, 2H), 4.18 (d, 2H, J=13.8 Hz), 4.12 (d, 2H, J=13.8 Hz), 3.72 (br s, 8H), 2.61 (br s, 8H), 2.05 (s, 6H), 1.74 (s, 2H), 1.46 (s, 2H); $^{13}$C{$^1$H} NMR (CDCl$_3$, 125 MHz): δ (ppm) 143.05, 141.72, 140.44, 135.41, 116.80, 108.07, 66.89, 57.08, 52.72, 43.94, 38.07; HR-MS (m/z) [M+H]$^+$: Calculated: 497.2646, Found: 497.2527.

Example 2. Polymer Synthesis

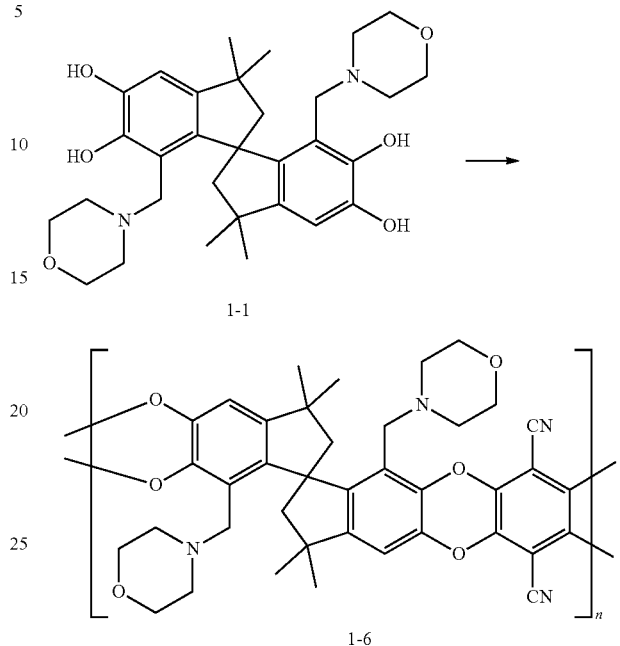

Synthesis of 1-6: 1-1 (3.0 g, 5.6 mmol) and tetrafluoroterephthalonitrile (1.2 g, 5.6 mmol) were dissolved in 20 mL of anhydrous DMF at 65° C. Freshly ground potassium carbonate (3.1 g, 22.4 mmol) was then slowly added and the mixture was stirred for 48 h. The yellow mixture was then poured into 200 mL of water then filtered and washed with 200 mL of water. The yellow solid was then dissolved in 50 mL of THF by heating, precipitated in 500 mL of acetone and then filtered. This process was repeated by dissolving the solid in 50 mL of chloroform and precipitating it in 500 mL of methanol. The polymer was washed with 200 mL of methanol and dried under vacuum at 65° C. to give 3.8 g (81%) of a yellow powder. $^1$H NMR (CDCl$_3$, 500 MHz): δ (ppm) 6.80 (br s, 2H), 3.53 (br s, 4H), 3.16 (br s, 2H), 2.99 (br s, 2H, CH$_2$, J=7.6 Hz), 2.24 (br s, 16H), 1.39 (br s, 6H), 1.31 (br s, 6H); Elemental Analysis for C$_{39}$H$_{40}$N$_4$O$_6$ Calculated: C 70.89, H 6.10, N 8.48; Found: C 69.91 H 5.90, N 8.16; M$_n$=21.6 kg mol$^{-1}$, M$_w$=33.1 kg mol$^{-1}$, PDI=1.53; BET Surface area: 505 m$^2$ g$^{-1}$.

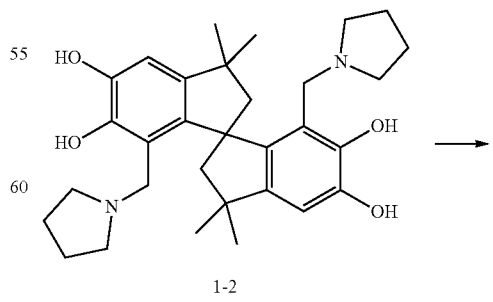

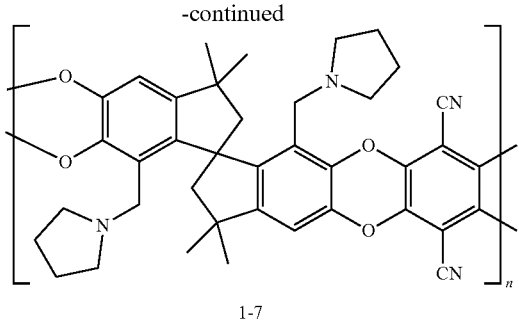

1-7

Synthesis of 1-7: 1-2 (8.8 g, 17.5 mmol) and tetrafluoroterephthalonitrile (3.5 g, 17.4 mmol) were dissolved in 50 mL of anhydrous DMF at 65° C. Freshly ground potassium carbonate (9.7 g, 70 mmol) was then slowly added and the mixture was stirred for 48 h. The yellow mixture was then poured into 800 mL of water then filtered and washed with 200 mL of water. The yellow solid was then dissolved in 200 mL of THF by heating, precipitated in 1000 mL of acetone and then filtered. This process was repeated by dissolving the solid in 200 mL of chloroform and precipitating it in 1000 mL of methanol. The polymer was washed with 200 mL of methanol and dried under vacuum at 65° C. to give 9.6 g (92%) of a yellow powder. $^1$H NMR (CDCl$_3$, 500 MHz): δ (ppm) 6.79 (br s, 2H), 3.19 (br s, 4H), 2.36 (br s, 2H), 2.23 (br s, 2H), 1.33 (br s, 6H), 1.29 (br s, 6H); Elemental Analysis for C$_{39}$H$_{4038}$N$_4$O$_4$ Calculated: C 74.74, H 6.11, N 8.94; Found: C 73.91 H 5.90, N 8.16; M$_n$=126 kg mol$^{-1}$, M$_w$=146 kg mol$^{-1}$, PDI=1.16; BET Surface area 434 m$^2$ g$^{-1}$.

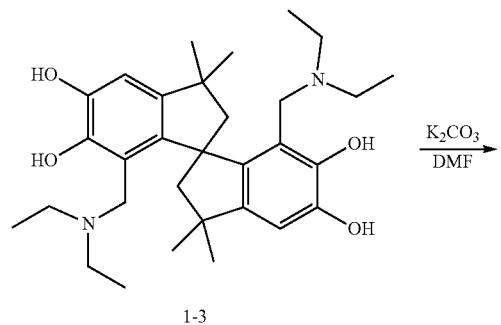

1-3

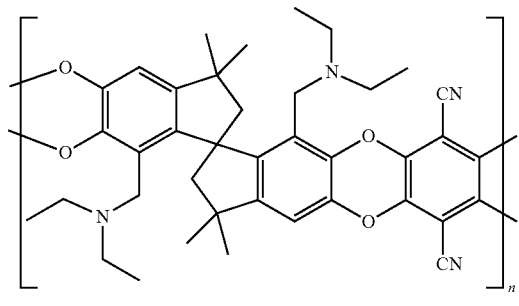

1-8

Synthesis of 1-8: 1-3 (11 g, 22 mmol) and tetrafluoroterephthalonitrile (4.4 g, 22 mmol) were dissolved in 100 mL of anhydrous DMF at 65° C. Freshly ground potassium carbonate (12 g, 87 mmol) was then slowly added and the mixture was stirred for 48 h. The yellow mixture was then poured into 500 mL of water then filtered and washed with 250 mL of water. The yellow solid was then dissolved in 200 mL of chloroform by heating, precipitated in 1000 mL of methanol and then filtered. This process was repeated by dissolving the solid in another 200 mL of chloroform and precipitating it in 1000 mL of methanol. The polymer was washed with 200 mL of methanol and dried under vacuum at 65° C. to give 12 g of 1-8 (85%) as a yellow powder. $^1$H NMR (CDCl$_3$, 500 MHz): δ (ppm) 6.80 (br s, 2H), 3.53 (br s, 4H), 3.16 (br s, 2H), 2.99 (br s, 2H, CH$_2$, J=7.6 Hz), 2.24 (br s, 16H), 1.39 (br s, 6H), 1.31 (br s, 6H); Elemental Analysis for C$_{39}$H$_{40}$N$_4$O$_6$ Calculated: C 70.89, H 6.10, N 8.48; Found: C 69.91 H 5.90, N 8.16; M$_n$=63.7 kg mol$^{-1}$, M$_w$=80.3 kg mol$^{-1}$, PDI=1.53, BET Surface area: 545 m$^2$ g$^{-1}$.

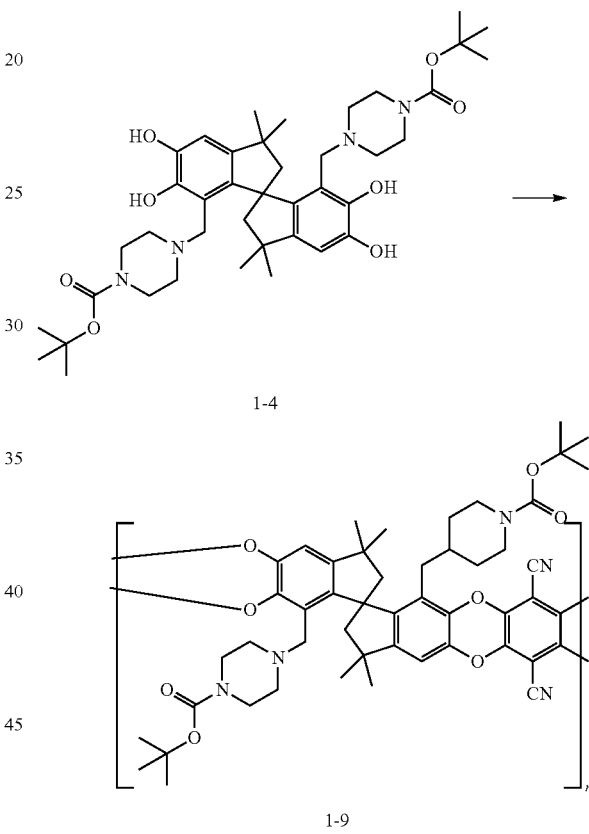

1-4

1-9

Synthesis of 1-9: 1-4 (5.0 g, 6.8 mmol) and tetrafluoroterephthalonitrile (1.4 g, 6.8 mmol) were dissolved in 60 mL of anhydrous DMF at 65° C. Freshly ground potassium carbonate 3.8 g (27 mmol) was then slowly added and the mixture was stirred for 3 h. The yellow mixture was then poured into 200 mL of water then filtered and washed with 200 mL of water. The yellow solid was then dissolved in 100 mL of THF by heating, precipitated in 500 mL of methanol and then filtered. This process was repeated by dissolving the solid in 100 mL of chloroform and precipitating it in 500 mL of methanol. The polymer was washed with 200 mL of methanol and dried under vacuum at 65° C. to give 4.7 g (82%) of a yellow powder. $^1$H NMR (CDCl$_3$, 500 MHz): δ (ppm) 6.80 (br s, 2H), 3.53 (br s, 4H), 3.16 (br s, 2H), 2.99 (br s, 2H, CH$_2$, J=7.6 Hz), 2.24 (br s, 16H), 1.31-1.45 (br m, 30H); Elemental Analysis for C$_{50}$H$_{57}$N$_5$O$_7$ Calculated: C 71.49, H 6.84, N 8.34; Found: C 71.10 H 6.54, N 8.25; $M_n$=46.9 kg mol$^{-1}$, $M_w$=51.5 kg mol$^{-1}$, PDI=1.11; BET Surface area 229 m$^2$ g$^{-1}$.

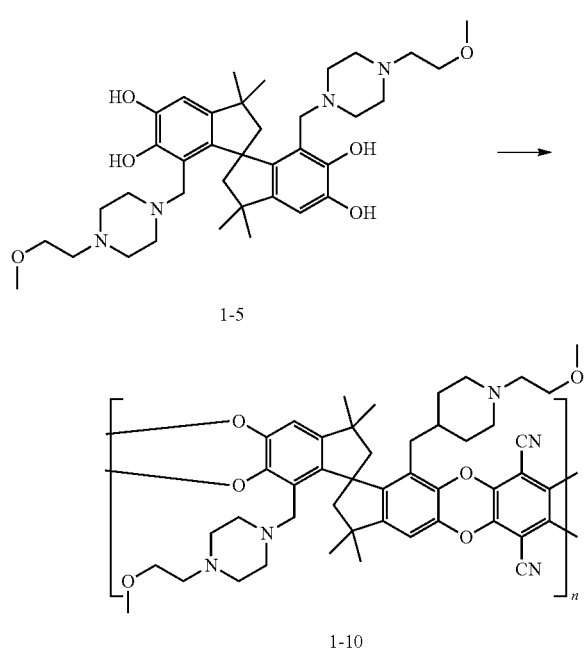

1-5

1-10

Synthesis of 1-10: 1-5 (5.0 g, 7.7 mmol) and tetrafluoroterephthalonitrile (1.5 g, 7.7 mmol) were dissolved in 50 mL of anhydrous DMF at 65° C. Freshly ground potassium carbonate (4.2 g, 31 mmol) was then slowly added and the mixture was stirred for 3 h. The yellow mixture was then poured into 200 mL of water then filtered and washed with 200 mL of water. The yellow solid was then dissolved in 75 mL of chloroform by heating, precipitated in 750 mL of methanol and then filtered. This process was repeated by dissolving the solid in another 75 mL of chloroform and precipitating it in 750 mL of methanol. The polymer was washed with 200 mL of methanol and dried under vacuum at 65° C. to give 3.4 g (54%) of a yellow powder. $^1$H NMR (CDCl$_3$, 500 MHz): δ (ppm) 6.80 (br s, 2H), 3.53 (br s, 4H), 2.57-3.48 (br m, 18H), 1.39 (br s, 6H), 1.31 (br s, 6H); Elemental Analysis for C$_{45}$H$_{52}$N$_6$O$_6$ Calculated: C 69.93, H 6.78, N 10.87; Found: C 69.77 H 6.75, N 10.53; $M_n$=26.1 kg mol, $M_w$=29.9 kg mol$^{-1}$, PDI=1.15; BET Surface area: 63 m$^2$ g$^{-1}$.

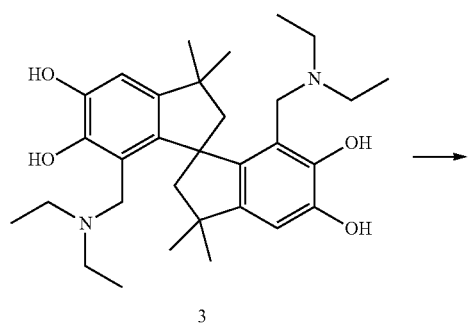

3

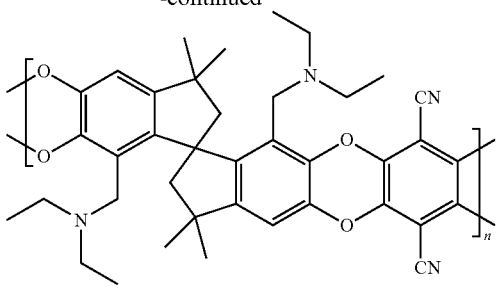

11

Figure 6:
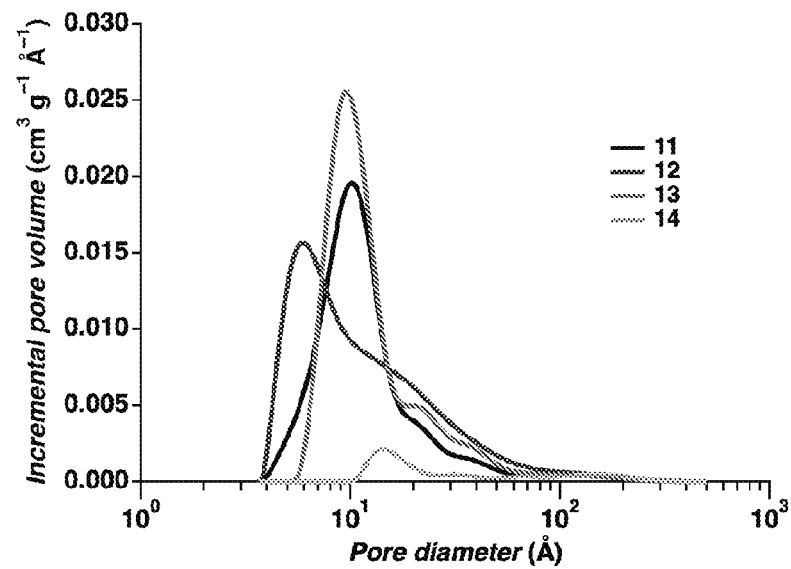
FIG. 6 shows the pore-size distribution of membranes fabricated from polymers 11-14.

Synthesis of 11: 3 (11 g, 22 mmol) and tetrafluoroterephthalonitrile (4.4 g, 22 mmol) were dissolved in anhydrous DMF (100 mL) at 65° C. Freshly ground potassium carbonate (12 g, 87 mmol) was slowly added and the mixture stirred for 48 h. The reaction mixture was then poured into water (500 mL) to precipitate the crude polymer as a yellow solid, which was then filtered and washed with an additional portion of water (250 mL). The crude polymer was dissolved in hot chloroform (200 mL) and subsequently precipitated into methanol (1.0 L), filtered, and washed with an additional portion of methanol (200 mL). This process was repeated. After drying in vacuo at 65° C., 11 was isolated as a yellow solid (12 g) in 85% yield. $^1$H NMR (CDCl$_3$, 500 MHz): δ (ppm) 6.80 (br s, 2H), 3.53 (br s, 4H), 3.16 (br s, 2H), 2.99 (br s, 2H), 2.24 (br s, 8H), 1.39 (br s, 6H), 1.31 (br s, 6H), 0.69 (br s, 12H); Elemental Analysis for C$_{39}$H$_{42}$N$_4$O$_4$ Calculated: C 74.26, H 6.71, N 8.88; Found: C 69.91 H 5.90, N 8.16; SEC (THF): $M_n$=63.7 kg mol$^{-1}$, $M_w$=80.3 kg mol$^{-1}$, PDI=1.53; BET surface area: 446 m$^2$ g$^{-1}$. Pore-size distribution is shown in FIG. 6.

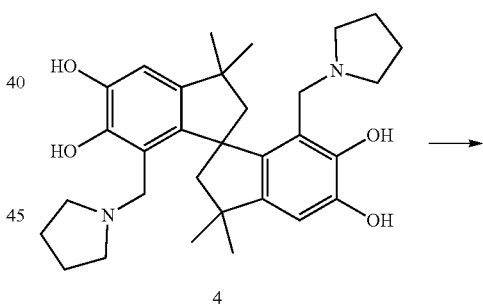

4

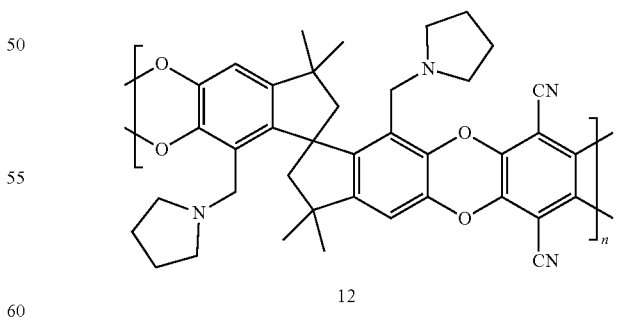

12

Synthesis of 12: 4 (8.8 g, 17.5 mmol) and tetrafluoroterephthalonitrile (3.5 g, 17.4 mmol) were dissolved in anhydrous DMF (50 mL) at 65° C. Freshly ground potassium carbonate (9.7 g, 70 mmol) was slowly added and the mixture stirred for 48 h. The reaction mixture was poured into water (800 mL) to precipitate the crude polymer as a yellow solid, which was then filtered and washed with an additional portion of water (200 mL). The crude polymer was dissolved in hot THF (200 mL) and subsequently precipitated into acetone (1.0 L), filtered, and washed with an additional portion of methanol (200 mL). An additional precipitation of the polymer into methanol (1.0 L) was conducted from a solution 12 in hot chloroform (200 mL). After drying in vacuo at 65° C., 12 was isolated as a yellow solid (9.6 g) in 92% yield. $^1$H NMR (CDCl$_3$, 500 MHz): δ (ppm) 7.01 (s, 2H), 2.33 (br s, 4H), 1.99 (br s, 4H), 1.63 (br s, 16H), 1.42 (br s, 12H); Elemental Analysis for C$_{39}$H$_{38}$N$_4$O$_4$ Calculated: C 74.74, H 6.11, N 8.94; Found: C 73.91 H 5.90, N 8.16; SEC (THF): M$_n$=126 kg mol$^{-1}$, M$_w$=146 kg mol$^{-1}$, PDI=1.16; BET surface area: 434 m$^2$ g$^{-1}$. Pore-size distribution is shown in FIG. 6.

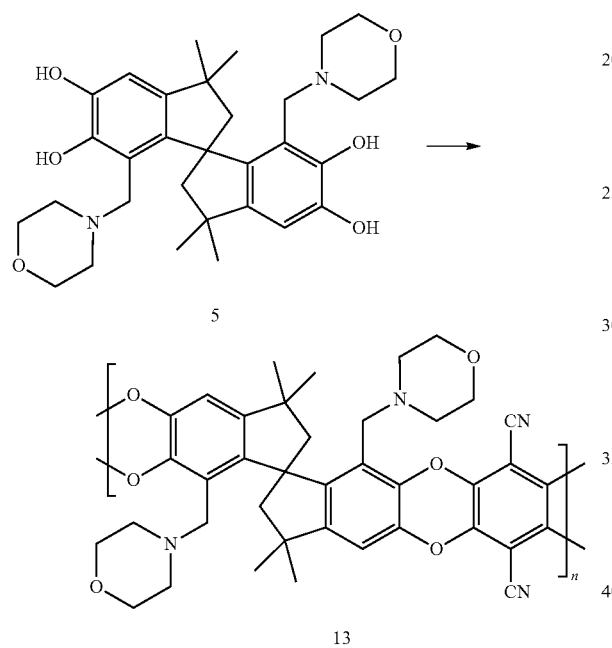

5

13

Synthesis of 13: 5 (3.0 g, 5.6 mmol) and tetrafluoroterephthalonitrile (1.2 g, 5.6 mmol) were dissolved in anhydrous DMF (20 mL) at 65° C. Freshly ground potassium carbonate (3.1 g, 22.4 mmol) was slowly added and the mixture stirred for 48 h. The reaction mixture was poured into water (200 mL) to precipitate the crude polymer as a yellow solid, which was then filtered and washed with an additional portion of water (200 mL). The crude polymer was dissolved in hot THF (50 mL) and subsequently precipitated into acetone (500 mL), filtered, and washed with an additional portion of methanol (200 mL). This process was repeated in hot chloroform (50 mL) and methanol (500 mL). After drying in vacuo at 65° C., 13 was isolated as a yellow solid (3.8 g) in 81% yield. $^1$H NMR (CDCl$_3$, 500 MHz): δ (ppm) 6.80 (br s, 2H), 3.53 (br s, 4H), 3.16 (br s, 2H), 2.99 (br s, 2H), 2.24 (br s, 16H), 1.39 (br s, 6H), 1.31 (br s, 6H); Elemental Analysis for C$_{39}$H$_{38}$N$_4$O$_6$ Calculated: C 71.11, H 5.81. N 8.51; Found: C 69.91 H 5.90, N 8.16; SEC (THF): M$_n$=21.6 kg mol$^{-1}$, M$_w$=33.1 kg mol$^{-1}$, PDI=1.53; BET surface area 505 m$^2$ g$^{-1}$. Pore-size distribution is shown in FIG. 6.

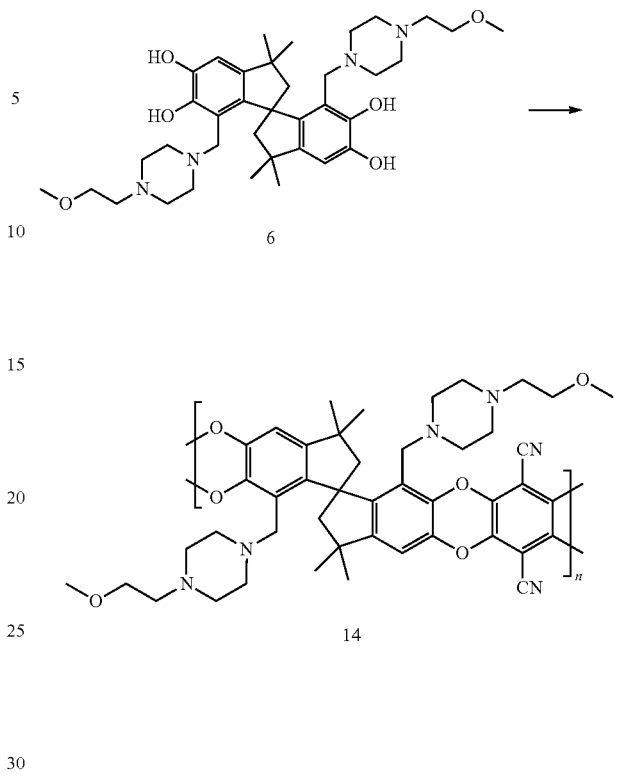

6

14

Synthesis of 14: 6 (5.0 g, 7.7 mmol) and tetrafluoroterephthalonitrile (1.5 g, 7.7 mmol) were dissolved in anhydrous DMF (50 mL) at 65° C. Freshly ground potassium carbonate (4.2 g, 31 mmol) was then slowly added and the mixture stirred for 3 h. The reaction mixture was poured into water (200 mL) to precipitate the crude polymer as a yellow solid, which was then filtered and washed with an additional portion of water (200 mL). The crude polymer was dissolved in hot chloroform (75 mL) and subsequently precipitated into methanol (750 mL), filtered, and washed with an additional portion of methanol (200 mL). This process was repeated. After drying in vacuo at 65° C., 14 was isolated as a yellow solid (3.4 g) in 54% yield. $^1$H NMR (DMSO-d$_6$, 500 MHz): δ (ppm) 7.00 (br s, 2H), 3.36 (br s, 6H), 3.19 (br s, 12H), 2.13-2.57 (br m, 20H), 1.48 (br s, 6H), 1.38 (br s, 6H); Elemental Analysis for C$_{45}$H$_{52}$N$_6$O$_6$ Calculated: C 69.93. H 6.78, N 10.87; Found: C 69.77 H 6.75, N 10.53; SEC (THF): M$_n$=26.1 kg mol$^{-1}$, M$_w$=29.9 kg mol$^{-1}$, PDI=1.15; BET surface area: 63 m$^2$ g$^{-1}$. Pore-size distribution is shown in FIG. 6.

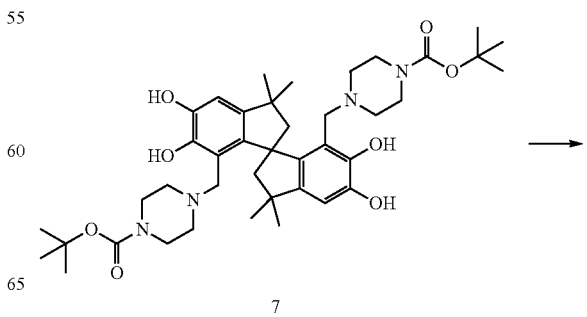

7

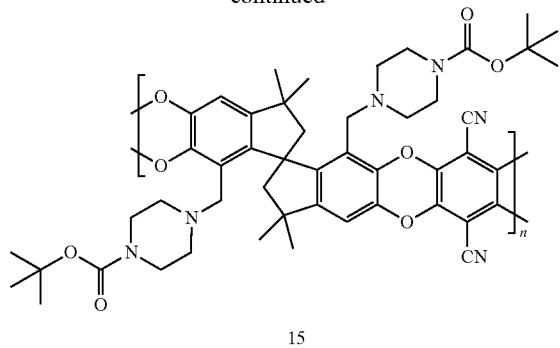

15

Figure 7:
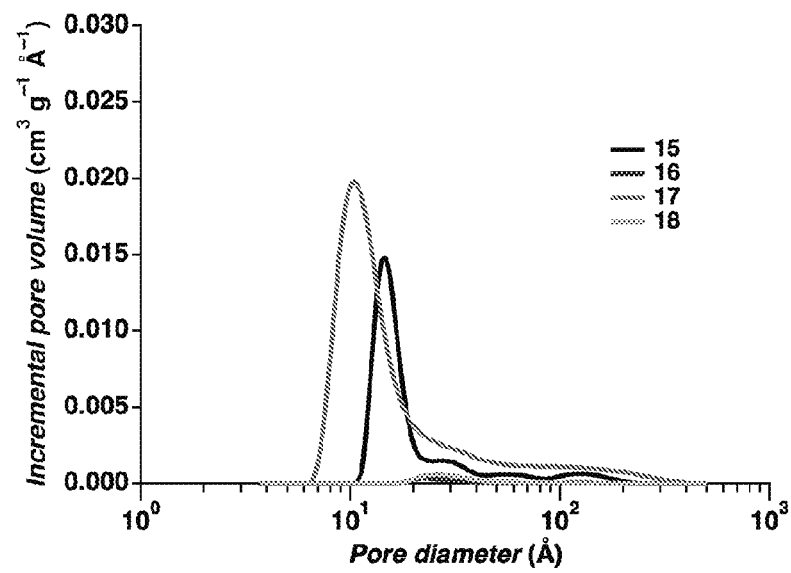
FIG. 7 shows the pore-size distribution of membranes fabricated from polymers 15-18.

Synthesis of 15: 7 (5.0 g, 6.8 mmol) and tetrafluoroterephthalonitrile (1.4 g, 6.8 mmol) were dissolved in anhydrous DMF (60 mL) at 65° C. Freshly ground potassium carbonate (3.8 g, 27 mmol) was then slowly added and the mixture stirred for 3 h. The reaction mixture was poured into water (200 mL) to precipitate the crude polymer as a yellow solid, which was then filtered and washed with an additional portion of water (200 mL). The crude polymer was dissolved in hot THF (100 mL) and subsequently precipitated into methanol (500 mL), filtered, and washed with an additional portion of methanol (200 mL). This process was repeated in hot chloroform (100 mL) and methanol (500 mL). After drying in vacuo at 65° C., 15 was isolated as a yellow solid (4.7 g) in 82% yield. $^1$H NMR (CDCl$_3$, 500 MHz): δ (ppm) 6.80 (br s, 2H), 3.53 (br s, 4H), 3.16 (br s, 2H), 2.99 (br s, 2H), 2.24 (br s, 16H), 1.31-1.45 (br m, 30H); Elemental Analysis for C$_{49}$H$_{56}$N$_6$O$_8$ Calculated: C 68.67, H 6.59, N 9.81; Found: C 71.10 H 6.54. N 8.25; SEC (THF): M$_n$=46.9 kg mol$^{-1}$, M$_w$=51.5 kg mol$^{-1}$, PDI=1.11; BET surface area: 234 m$^2$ g$^{-1}$. Pore-size distribution is shown in FIG. 7.

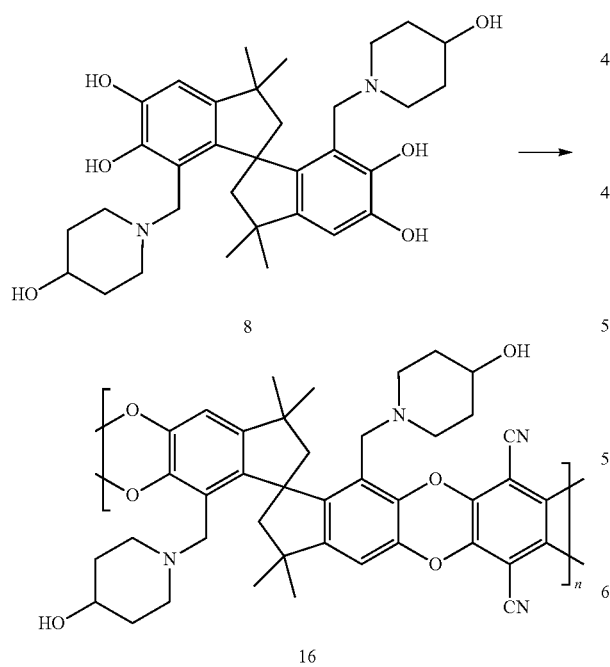

Synthesis of 16: 8 (1.0 g, 1.8 mmol) and tetrafluoroterephthalonitrile (352 mg, 1.8 mmol) were dissolved in anhydrous DMF (10 mL) at 65° C. Freshly ground potassium carbonate 971 mg (7.0 mmol) was then slowly added and the mixture stirred for 48 h. The reaction mixture was poured into water (100 mL) to precipitate the crude polymer as a yellow solid, which was then filtered and washed with an additional portion of water (100 mL). The crude polymer was dissolved in hot chloroform (20 mL) and subsequently precipitated into methanol (200 mL), filtered, and washed with an additional portion of methanol (200 mL). This process was repeated. After drying in vacuo at 65° C., 16 was isolated as a yellow solid (600 mg) in 45% yield. $^1$H NMR (DMSO-d$_6$, 500 MHz): δ (ppm) 7.09 (br s, 2H), 4.53 (br s, 2H), 2.92 (br s, 4H), 2.03-2.45 (br m, 8H), 1.85 (br s, 4H), 1.56 (br s, 10H), 1.39 (br s, 6H), 1.29 (br s, 6H); SEC (DMF): M$_n$=11.9 kg mol$^{-1}$, M$_w$=19.2 kg mol$^{-1}$, PDI=1.61; BET surface area: 11 m$^2$ g$^{-1}$. Pore-size distribution is shown in FIG. 7.

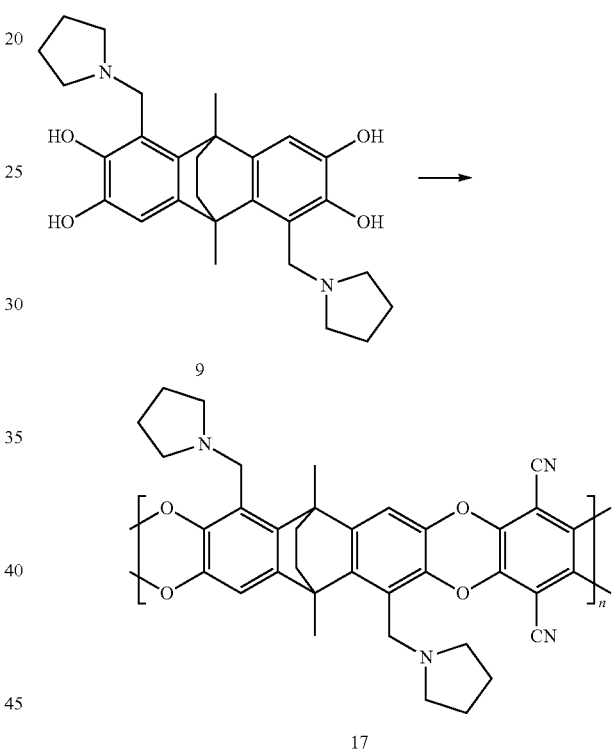

Synthesis of 17: 9 (3.0 g, 5.6 mmol) and tetrafluoroterephthalonitrile (1.2 g, 5.6 mmol) were dissolved in anhydrous DMF (20 mL) at 65° C. Freshly ground potassium carbonate (3.1 g, 22.4 mmol) was then slowly added and the mixture stirred for 48 h. The reaction mixture was poured into water (50 mL) to precipitate the crude polymer as an orange solid, which was then filtered and washed with an additional portion of water (50 mL). The crude polymer was dissolved in hot THF (5 mL) and subsequently precipitated into methanol (50 mL), filtered, and washed with an additional portion of methanol (50 mL). This process was repeated from hot chloroform (5 mL) using methanol (50 mL). After drying in vacuo at 65° C., 17 was isolated as an orange solid (214 mg) in 90% yield. $^1$H NMR (CDCl$_3$, 500 MHz): δ (ppm) 7.00 (br s, 2H), 3.89 (br d, 4H), 2.55 (br s, 8H), 2.32 (br s, 4H), 1.75 (br s, 6H), 1.58 (br s, 8H); Elemental Analysis for C$_{36}$H$_{32}$N$_4$O$_4$ Calculated: C 73.95, H 5.52, N 9.58; BET surface area: 444 m$^2$ g$^{-1}$. Pore-size distribution is shown in FIG. 7.

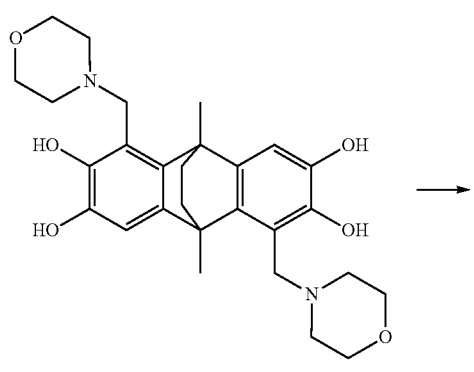

10

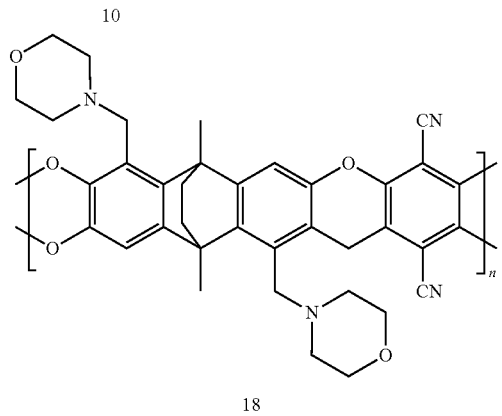

18

Synthesis of 18: 10 (200 mg, 402 μmol) and tetrafluoroterephthalonitrile (82.9 mg, 414 μmol) were dissolved in anhydrous DMF (3.4 mL) at 65° C. Freshly ground potassium carbonate (229 mg, 1.66 mmol) was then slowly added and the mixture was stirred for 96 h. The reaction mixture was poured into water (50 mL) to precipitate the crude polymer as a yellow solid, which was then filtered and washed with an additional portion of water (50 mL). The crude polymer was dissolved in hot THF (5 mL) and subsequently precipitated into methanol (50 mL), filtered, and washed with an additional portion of methanol (50 mL). This process was repeated in hot chloroform (5 mL) and methanol (50 mL). After drying in vacuo at 65° C., 18 was isolated as a yellow solid (211 mg) in 80% yield. $^1$H NMR (CDCl$_3$, 500 MHz): δ (ppm) 7.00 (br s, 2H), 3.66 (br s, 12H), 2.48 (br s, 8H), 2.29 (br s, 6H), 1.84 (br s, 2H), 1.47 (br s, 2H); Elemental Analysis for C$_{36}$H$_{32}$N$_4$O$_6$ Calculated: C 70.12, H 5.23, N 9.09; BET surface area: 19 m$^2$ g$^{-1}$. Pore-size distribution is shown in FIG. 7.

Example 3. Post-Polymerization Modification of Polymers with Hydroxylamine

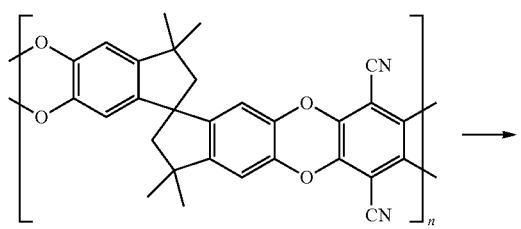

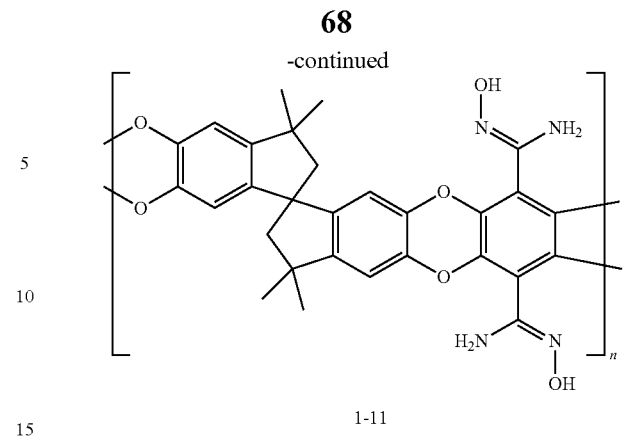

1-11

Synthesis of 1-11: To a 500 mL round bottom flask was added 5.00 g of PIM-1 (21.8 mmol cyano functional groups) in tetrahydrofuran (380 mL). The mixture was heated to at 60° C. to dissolve the polymer. A solution of 50 wt % aqueous hydroxylamine (50 mL, 760 mmol) was then added dropwise. The reaction mixture was stirred overnight, and then cooled and precipitated as a white powder in 1320 mL of methanol. The solid was filtered and then rinsed twice with methanol before drying in vacuo at 50° C. to yield a pale yellow powder (3.93 g, 68.8%). $^1$H NMR (DMSO-d$_6$, 500 MHz): δ (ppm) 9.47 (br t, 2H), 6.82 (br s, 2H), 6.16 (br s, 2H), 5.82 (br s, 4H), 2.17 (br d, 4H), 1.32 (br s, 6H), 1.25 (br s, 6H); Elemental Analysis for C$_{29}$H$_{26}$N$_4$O$_6$ Calculated: C 66.15, H 4.98, N 10.64; Found: C 64.62 H 5.09, N 10.17; $M_n$=42.7 kg mol$^{-1}$, $M_w$=119 kg mol$^{-1}$, PDI=2.78; BET Surface area: 490 m$^2$ g$^{-1}$.

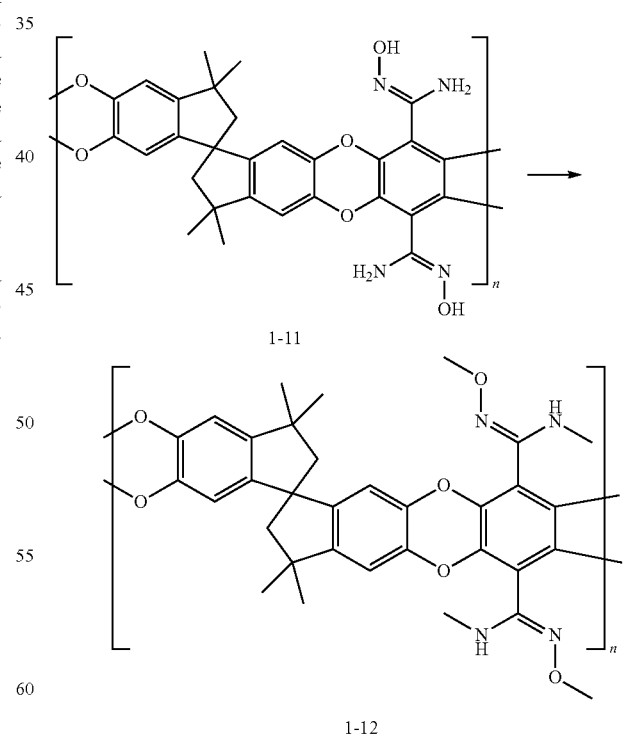

Synthesis of 1-12: To a solution of 1-11 (1.50 g, 5.7 mmol reactive sites) in dimethyl sulfoxide (57 mL) was added a solution lithium hydroxide monohydrate (0.478 g, 11.40 mmol) in MilliQ water (5.75 mL), dropwise over 1 min.

After stirring at least 1 h under nitrogen, the reaction mixture was placed on ice, and dimethyl sulfate (1.437 g, 11.40 mmol) was added in two portions. The reaction was allowed to reach room temperature and stirred for 72 h, before quenching with sodium hydroxide. The product was precipitated in 400 mL MilliQ water, then filtered and rinsed with two 100 mL portions of MilliQ water, followed by an additional precipitation from dimethyl sulfoxide into MilliQ water, and then dried in vacuo at 60° C. to yield 12 (1.28 g, 81%) as a dark yellow solid. $^1$H NMR (DMSO-d$_6$, 500 MHz): δ (ppm) 6.67 (br s, 2H), 6.28 (br s 2H), 3.42-4.08 (br m, 6H), 2.79-3.38 (br m, 6H), 2.20 (br d, 4H), 1.28 (br s, 6H), 1.33 (br s, 6H); Elemental Analysis for C$_{33}$H$_{34}$N$_4$O$_6$ Calculated: C 68.03, H 5.88, N 9.62; Found: C 65.21 H 5.76, N 8.93: M$_n$=17.5 kg mol$^{-1}$, M$_w$=102 kg mol$^{-1}$, PDI=5.85.

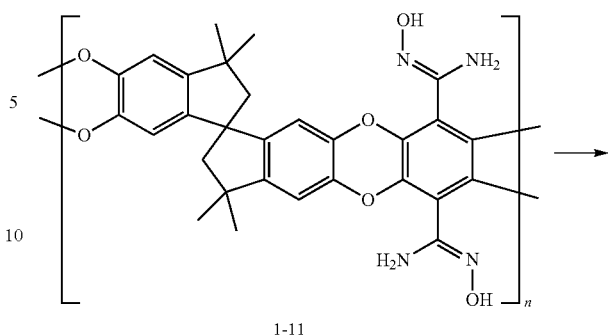

1-11

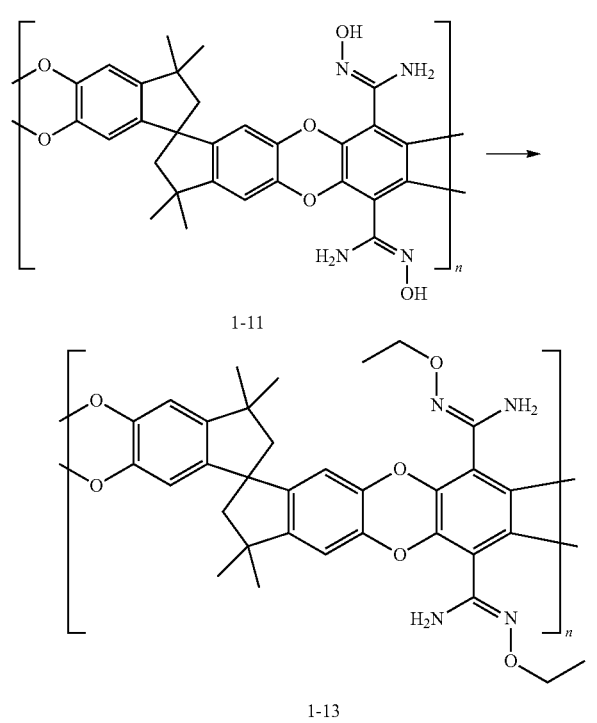

1-11

1-13

Synthesis of 1-13: To a solution of 1-11 in dimethyl sulfoxide (1.50 g, 5.7 mmol reactive sites in 57 mL) was added a solution of lithium hydroxide monohydrate in MilliQ water (0.478 g, 11.40 mmol in 5.75 mL) dropwise over ~1 min. After stirring at least one hour under nitrogen, the reaction mixture was placed on ice, and diethyl sulfate (1.757 g, 11.40 mmol) was added in two portions. The reaction was allowed to reach room temperature and stirred for 72 h, before quenching with sodium hydroxide. The product was precipitated in 400 mL MilliQ water, then filtered and rinsed with two 100 mL portions of MilliQ water, followed by an additional precipitation from DMSO into MilliQ water, and then dried in vacuo at 60° C.; The resulting dark yellow solid was isolated 1.34 g of product (84.8% yield). $^1$H NMR (DMSO-d$_6$, 500 MHz): δ (ppm) 6.82 (br s, 2H), 6.18 (br s, 4H), 3.88 (br t, 4H), 2.17 (br d, 4H), 0.76-1.72 (br m, 18H); Elemental Analysis for C$_{33}$H$_{34}$N$_4$O$_6$ Calculated: C 68.03, H 5.88, N 9.62; Found: C 66.17 H 6.08, N 8.85; M$_n$=45.4 kg mol$^{-1}$, M$_w$=222 kg mol$^{-1}$. PDI=4.87.

1-14

Synthesis of 1-14: To a solution of 1-11 (1.00 g, 3.8 mmol reactive sites) in dimethyl sulfoxide (38 mL) was added a solution of lithium hydroxide monohydrate (0.478 g, 7.60 mmol) in MilliQ water (4.00 mL) dropwise over 1 min. After stirring at least 1 h under nitrogen, 1,3-propanesultone (0.928 g, 7.60 mmol) was added, and the reaction mixture stirred for 24 h. The product was precipitated in 400 mL MilliQ water, with tetraethylammonium bromide (15.97 g, 76.0 mmol), and filtered via Buchner funnel then rinsed with three 100 mL portions of MilliQ water. $^1$H NMR (MeOD, 500 MHz): δ (ppm) 6.82 (br s, 2H), 6.26 (br s, 2H), 4.03 (br t, 4H), 3.30 (q, 16H), 2.87 (br t, 4H), 1.62-2.53 (br m, 12H) 1.55-1.90 (br s overlapping tt, 36H).

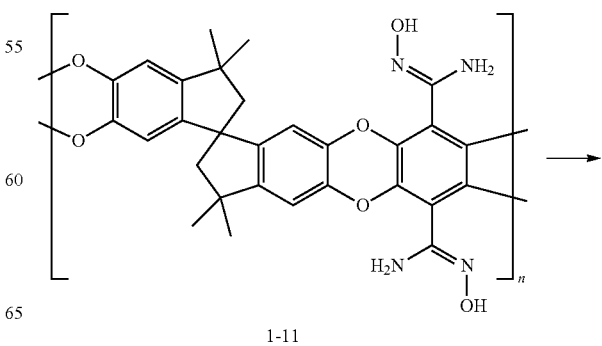

1-11

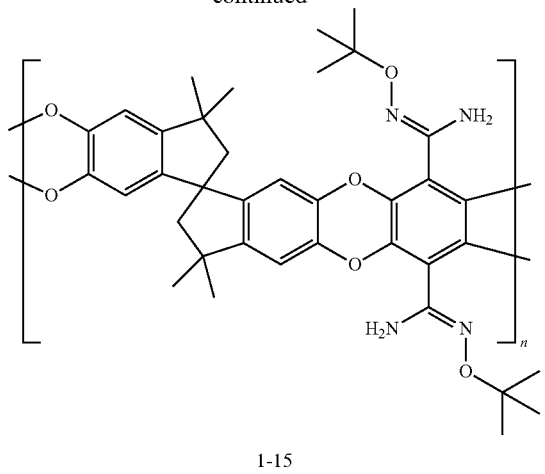

1-15

Synthesis of 1-15: To a solution of 1-11 (1.00 g, 3.8 mmol reactive sites) in dimethyl sulfoxide (38 mL) was added magnesium perchlorate (0.08 g, 0.38 mmol) and di-tert-butyl dicarbonate (2.14 g, 7.60 mmol). The reaction was stirred for 24 h at 40° C., then cooled and precipitated in 400 mL of MilliQ water with a few drops of sodium hydroxide and then filtered. The solid was rinsed with three 50 mL portions of MilliQ water, and then two 50 mL portions of chloroform to remove excess di-tert-butyl dicarbonate, and then dried in vacuo at 60° C. to yield 1-15 as a dark yellow solid (0.90 g, 74% yield). $^1$H NMR (DMSO-$d_6$, 500 MHz): δ (ppm) 6.88 (br s, 4H), 6.25 (br s, 2H), 2.19 (br d, 4H), 0.76-1.72 (br m, 18H), 0.95-1.77 (br m, 30H); Elemental Analysis for $C_{37}H_{42}N_4O_6$ Calculated: C 69.57. H 6.63. N 8.77; Found: C 61.29 H 5.47, N 8.09; BET Surface area: 190 $m^2$ $g^{-1}$.

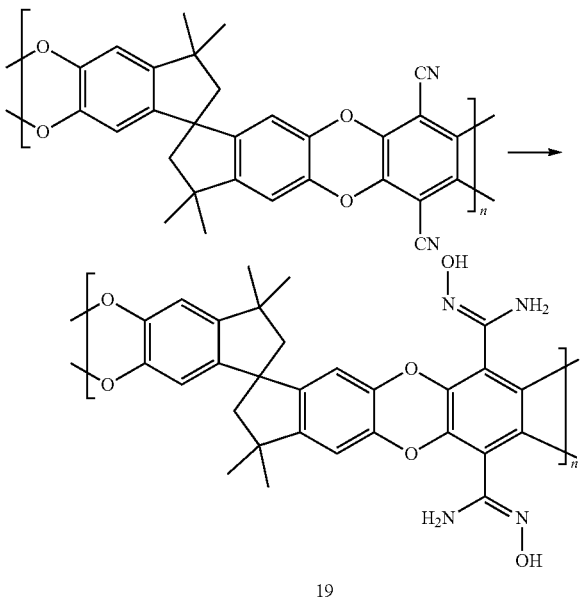

19

Figure 8:
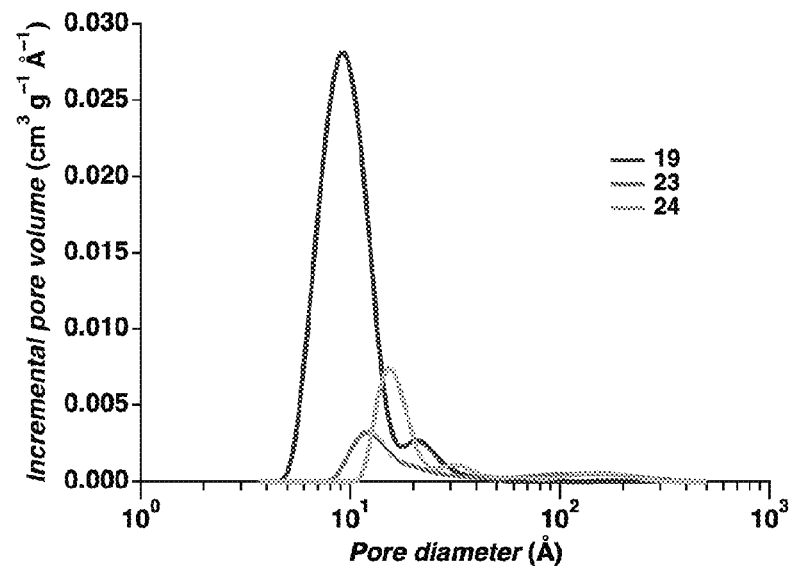
FIG. 8 shows the pore-size distribution of membranes fabricated from polymers 19, 23, and 24.

19: To around bottom flask was added PIM-1 (5.0 g, 9.6 mmol) and tetrahydrofuran (380 mL). The mixture was heated to at 60° C. to dissolve the polymer. A solution of 50 wt % aqueous hydroxylamine (50 mL, 760 mmol) was then added dropwise. The reaction mixture was stirred overnight and then cooled before precipitating the polymer into methanol (1320 mL). The solid was filtered and then rinsed twice with methanol (500 mL) before drying in vacuo at 50° C. to give 19 as a pale yellow powder (3.93 g) in 69% yield. $^1$H NMR (DMSO-$d_6$, 500 MHz): δ (ppm) 9.47 (br t, 2H), 6.82 (br s, 2H), 6.16 (br s, 2H), 5.82 (br s, 4H), 2.17 (br d, 4H), 1.32 (br s, 6H), 1.25 (br s, 6H); Elemental Analysis for $C_{29}H_{26}N_4O_6$ Calculated: C 66.15, H 4.98, N 10.64; Found: C 64.62 H 5.09, N 10.17; SEC (DMF): $M_n$=42.7 kg mol$^{-1}$, $M_w$=119 kg mol$^{-1}$, PDI=2.78; BET surface area: 454 $m^2$ $g^{-1}$. Pore-size distribution is shown in FIG. 8.

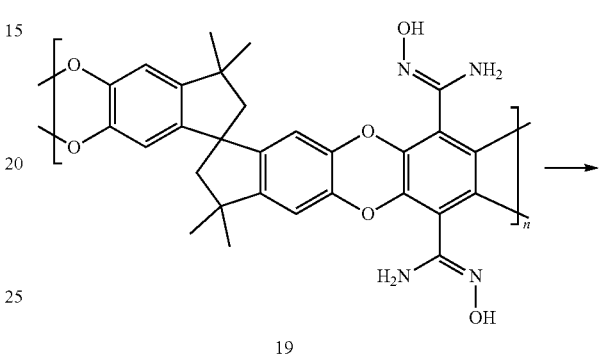

19

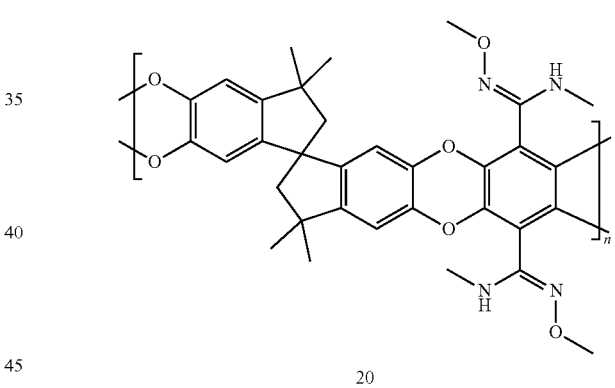

20

Figure 9:
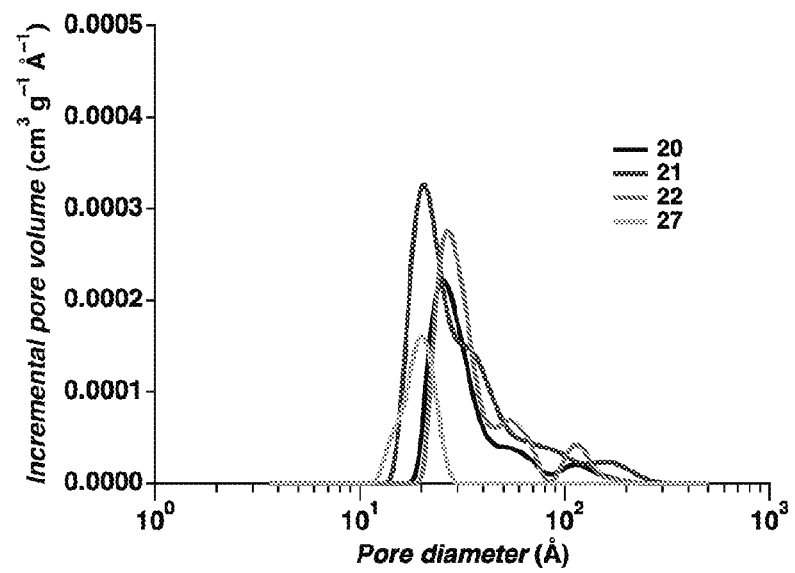
FIG. 9 shows the pore-size distribution of membranes fabricated from polymers 20, 21, 22, and 27.

20: To a solution of 19 (1.50 g, 2.6 mmol) in dimethyl sulfoxide (57 mL) was added a solution of lithium hydroxide monohydrate (0.478 g, 11.40 mmol) in MilliQ water (5.75 mL) dropwise over 1 min. After stirring for 1 h under nitrogen, the reaction mixture was placed on ice, and dimethyl sulfate (1.08 mL, 11.40 mmol) was added in two portions. The reaction was allowed to reach room temperature and stirred for 72 h, before quenching with sufficient sodium hydroxide to increase the pH above 7. The product was precipitated in MilliQ water (400 mL), filtered and rinsed with two portions of MilliQ water (100 mL each), and then dried in vacuo at 60° C. to give 20 as a dark yellow solid (1.28 g) in 81% yield. $^1$H NMR (DMSO-$d_6$, 500 MHz): δ (ppm) 6.67 (br s, 2H), 6.28 (br s, 2H), 5.83 (br s, 2H), 3.42-4.08 (br m, 6H), 2.79-3.38 (br m, 6H), 2.20 (br d, 4H), 1.28 (br s, 6H), 1.33 (br s, 6H); Elemental Analysis for $C_{33}H_{34}N_4O_6$ Calculated: C 68.03, H 5.88, N 9.62; Found: C 65.21 H 5.76, N 8.93; SEC (DMF): $M_n$=17.5 kg mol$^{-1}$, $M_w$=102 kg mol$^{-1}$, PDI=5.85; BET Surface area: 7 $m^2$ $g^{-1}$. Pore-size distribution is shown in FIG. 9.

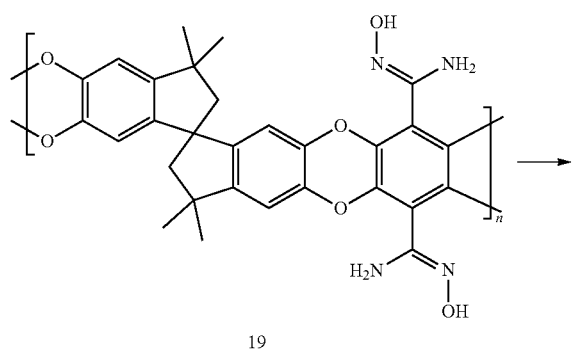

19

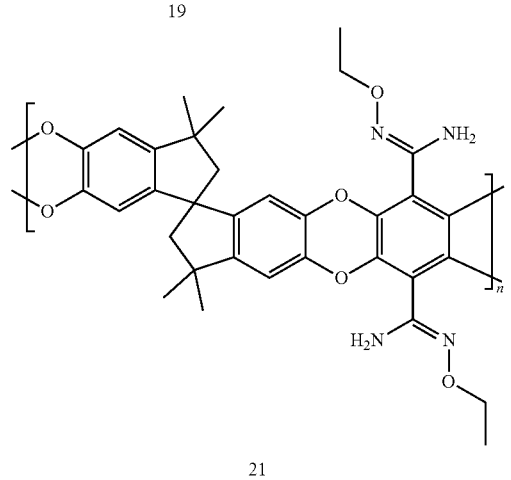

21

21: To a solution of 19 (1.50 g, 2.6 mmol) in dimethyl sulfoxide (57 mL) was added a solution of lithium hydroxide monohydrate (0.478 g, 11.40 mmol) in MilliQ water (5.75 mL) dropwise over 1 min. After stirring for 1 h under nitrogen, the reaction mixture was placed on ice, and diethyl sulfate (1.757 g, 11.40 mmol) was added in two portions. The reaction was allowed to reach room temperature and stirred for 72 h, before quenching with sufficient sodium hydroxide to increase the pH above 7. The product was precipitated in MilliQ water (400 mL), then filtered and rinsed with two portions of MilliQ water (100 mL each), and then dried in vacuo at 60° C. to give 21 as a dark yellow solid (1.34 g) in 84.8% yield. $^1$H NMR (DMSO-d$_6$, 500 MHz): h (ppm) 6.82 (br s, 2H), 6.18 (br s, 2H), 5.82 (br s, 4H), 3.88 (br t, 4H), 2.17 (br d, 4H), 0.76-1.72 (br m, 18H); Elemental Analysis for C$_{33}$H$_{34}$N$_4$O$_6$ Calculated: C 68.03, H 5.88, N 9.62; Found: C 66.17 H 6.08, N 8.85; SEC (DMF): M$_n$=45.4 kg mol$^{-1}$, M$_w$=222 kg mol$^{-1}$, PDI=4.87; BET Surface area: 10 m$^2$ g$^{-1}$. Pore-size distribution is shown in FIG. 9.

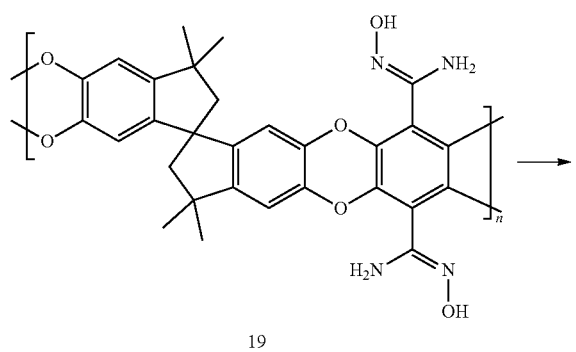

19

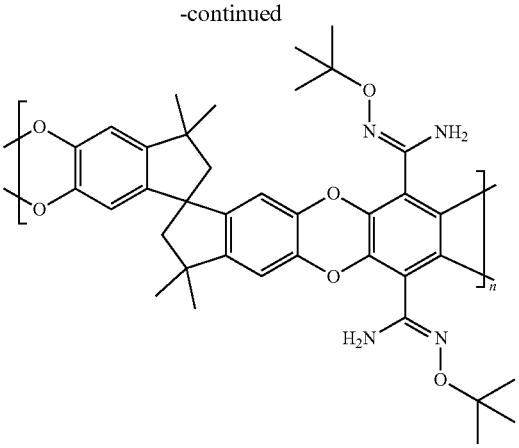

22

22: To a solution of 19 (1.00 g, 1.7 mmol) in dimethyl sulfoxide (38 mL) was added magnesium perchlorate (0.08 g, 0.38 mmol) and di-tert-butyl dicarbonate (2.14 g, 7.60 mmol). The reaction was stirred for 24 h at 40° C., then cooled and precipitated in MilliQ water (400 mL) with a few drops of sodium hydroxide and then filtered. The solid was rinsed with three portions of MilliQ water (50 mL each), and then two portions of chloroform (50 mL each) to remove excess di-tert-butyl dicarbonate, and then dried in vacuo at 60° C. to give 22 as a dark yellow solid (0.90 g) in 74% yield. $^1$H NMR (DMSO-d$_6$, 500 MHz): δ (ppm) 6.87 (br s, 4H), 6.25 (br s, 2H), 2.18 (br d, 4H), 0.93-1.73 (br m, 34H); Elemental Analysis for C$_{37}$H$_{42}$N$_4$O$_6$ Calculated: C 69.57, H 6.63, N 8.77; Found: C 61.29 H 5.47, N 8.09; SEC (DMF): M$_n$=43.2 kg mol$^{-1}$, M$_w$=154 kg mol$^{-1}$, PDI=3.56; BET Surface area: 11 m$^2$ g$^{-1}$. Pore-size distribution is shown in FIG. 9.

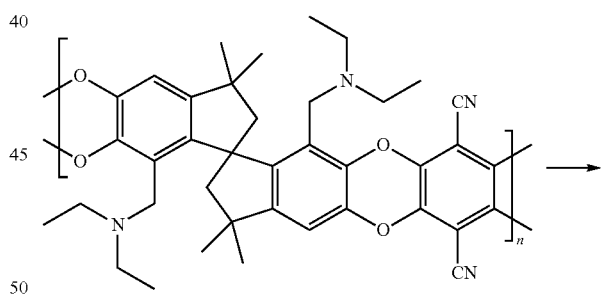

11

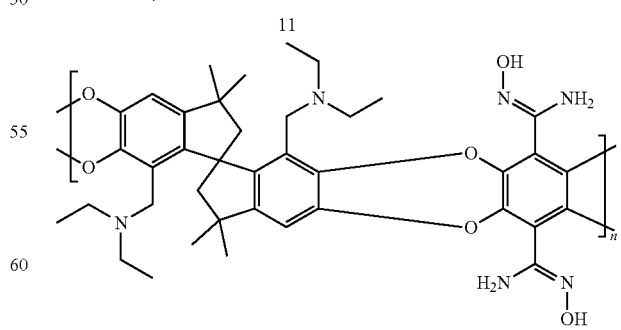

23

23: To a round bottom flask was added 11 (7.5 g, 12.5 mmol) and tetrahydrofuran (375 mL). The mixture was heated to at 60° C. to dissolve the polymer. A solution of 50 wt % aqueous hydroxylamine (60 mL, 875 mmol) was then added dropwise. The reaction mixture was stirred overnight and then cooled before precipitating the polymer into a 1:1 (v/v) solution of water and methanol (1875 mL). The solid was filtered and then rinsed twice with methanol (500 mL) before drying in vacuo at 50° C. to give 23 as a white powder (1.45 g) in 18% yield. $^1$H NMR (DMSO-dr, 500 MHz): δ (ppm) 9.48 (br s, 2H), 6.74 (br s, 2H), 5.81 (br s, 4H), 3.63 (br s, 4H), 2.91 (br s, 4H), 2.18 (br s, 8H), 1.31 (br s, 6H), 1.26 (br s, 6H), 0.69 (br s, 12H); SEC (DMF): $M_n$=5.0 kg mol$^{-1}$, $M_w$=14.2 kg mol$^{-1}$, PDI=2.83: BET surface area: 79 m$^2$ g$^{-1}$. Pore-size distribution is shown in FIG. 8.

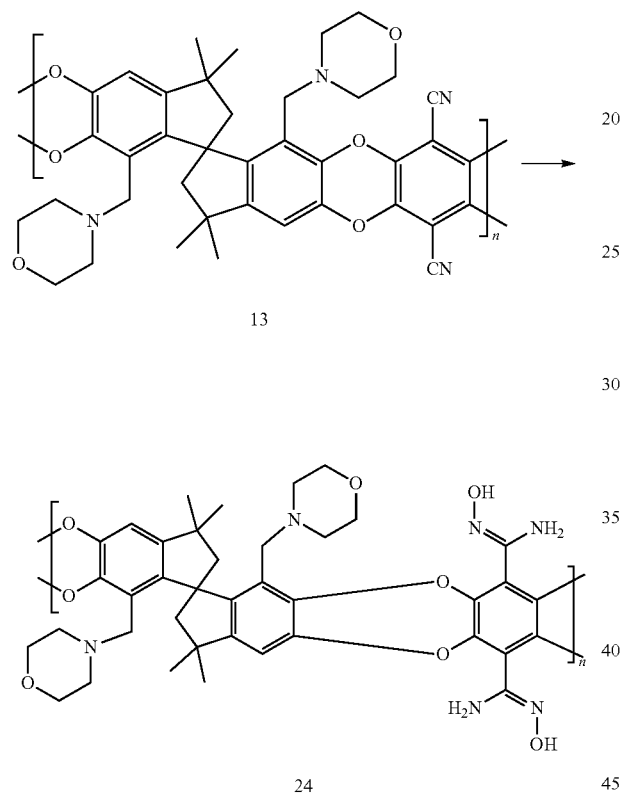

13

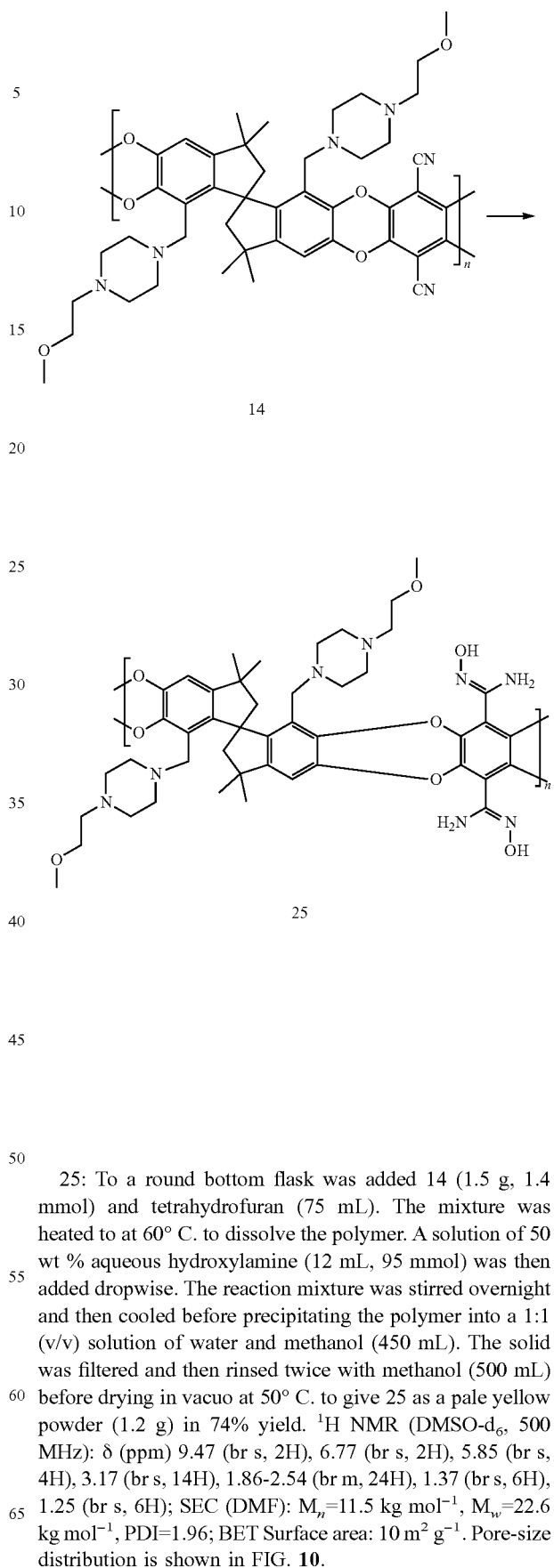

14

25

24: To a round bottom flask was added 13 (2.7 g, 3.8 mmol) and tetrahydrofuran (120 mL). The mixture was heated to at 60° C. to dissolve the polymer. A solution of 50 wt % aqueous hydroxylamine (20 mL, 280 mmol) was then added dropwise. The reaction mixture was stirred overnight and then cooled before precipitating the polymer into methanol (400 mL). The solid was filtered and then rinsed twice with methanol (500 mL) before drying in vacuo at 50° C. to give 24 as a white powder (2.0 g) in 68% yield. $^1$H NMR (DMSO-d$_6$, 500 MHz): δ (ppm) 9.50 (br s, 2H), 6.79 (br s, 2H), 5.86 (br s, 4H), 3.43 (br s, 4H), 3.02 (br s, 2H), 2.84 (br s, 2H) 2.11 (br s, 16H), 1.36 (br s, 6H), 1.26 (br s, 6H); SEC (DMF): $M_n$=29.7 kg mol$^{-1}$, $M_w$=62.8 kg mol$^{-1}$, PDI=2.12: BET Surface area: 152 m$^2$ g$^{-1}$. Pore-size distribution is shown in FIG. 8.

Figure 10:
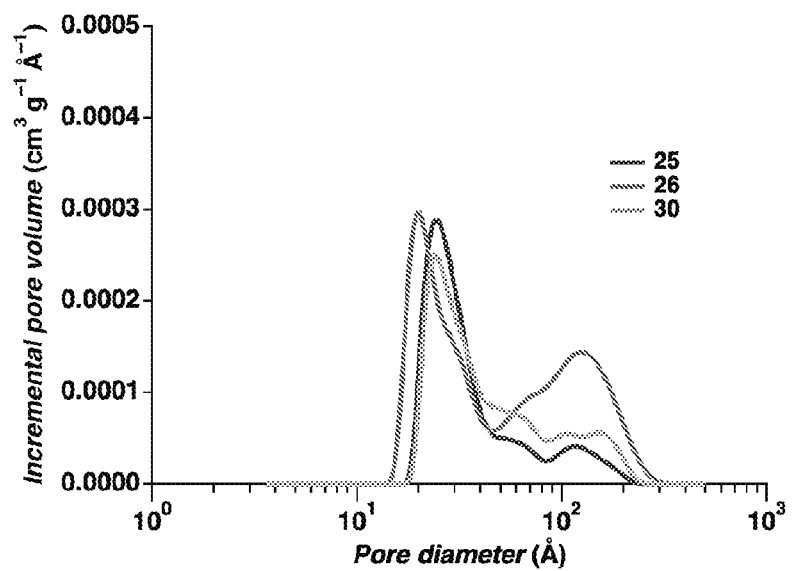
FIG. 10 shows the pore-size distribution of membranes fabricated from polymers 25, 26, and 30.

25: To a round bottom flask was added 14 (1.5 g, 1.4 mmol) and tetrahydrofuran (75 mL). The mixture was heated to at 60° C. to dissolve the polymer. A solution of 50 wt % aqueous hydroxylamine (12 mL, 95 mmol) was then added dropwise. The reaction mixture was stirred overnight and then cooled before precipitating the polymer into a 1:1 (v/v) solution of water and methanol (450 mL). The solid was filtered and then rinsed twice with methanol (500 mL) before drying in vacuo at 50° C. to give 25 as a pale yellow powder (1.2 g) in 74% yield. $^1$H NMR (DMSO-d$_6$, 500 MHz): δ (ppm) 9.47 (br s, 2H), 6.77 (br s, 2H), 5.85 (br s, 4H), 3.17 (br s, 14H), 1.86-2.54 (br m, 24H), 1.37 (br s, 6H), 1.25 (br s, 6H); SEC (DMF): $M_n$=11.5 kg mol$^{-1}$, $M_w$=22.6 kg mol$^{-1}$, PDI=1.96; BET Surface area: 10 m$^2$ g$^{-1}$. Pore-size distribution is shown in FIG. 10.

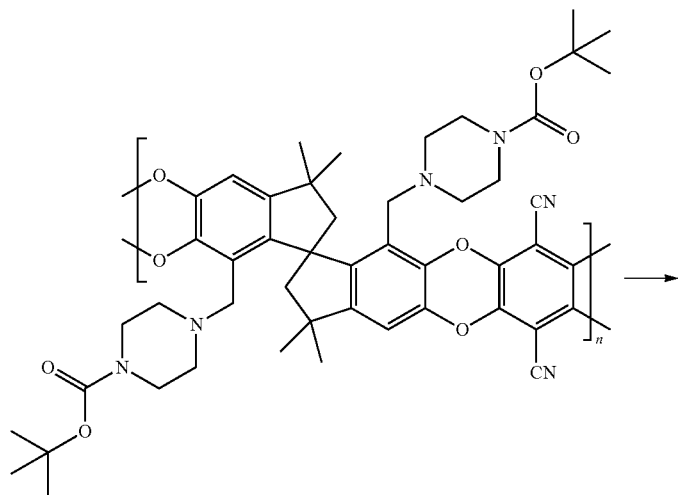

15

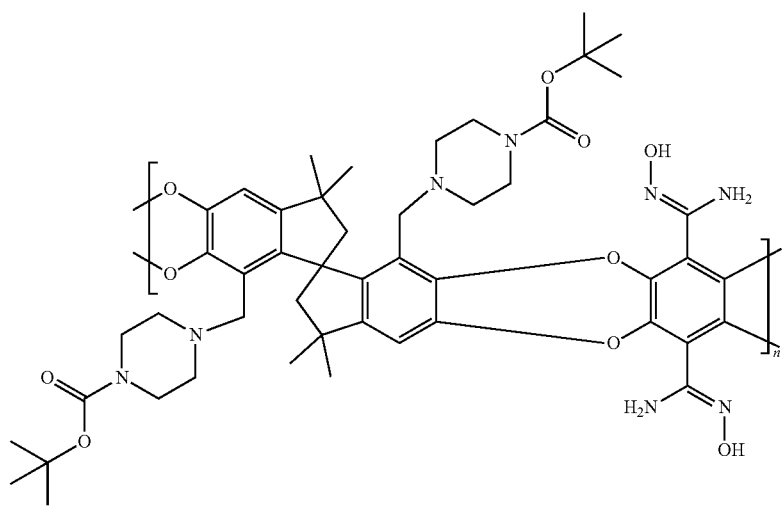

26

26: To a round bottom flask was added 15 (1.0 g, 1.2 mmol) and tetrahydrofuran (60 mL). The mixture was heated to at 60° C. to dissolve the polymer. A solution of 50 wt % aqueous hydroxylamine (11 mL, 163 mmol) was then added dropwise. The reaction mixture was stirred overnight and then cooled before precipitating the polymer into water (600 mL). The solid was filtered and then rinsed twice with methanol (500 mL) before drying in vacuo at 50° C. to give 26 as a pale yellow powder (950 mg) in 89% yield. $^1$H NMR (DMSO-$d_6$, 500 MHz): δ (ppm) 7.80 (br s, 2H), 6.81 (br s, 2H), 5.75 (br s, 4H), 3.12 (br s, 8H), 2.03 (br s, 16H), 1.18-1.46 (br m, 30H)); SEC (DMF): $M_n$=8.0 kg mol$^{-1}$, $M_w$=12.4 kg mol$^{-1}$, PDI=1.56; BET Surface area: 12 m$^2$ g$^{-1}$. Pore-size distribution is shown in FIG. 10.

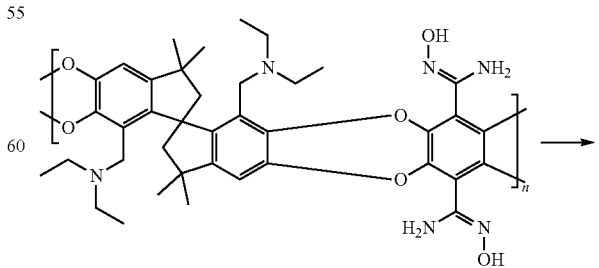

23

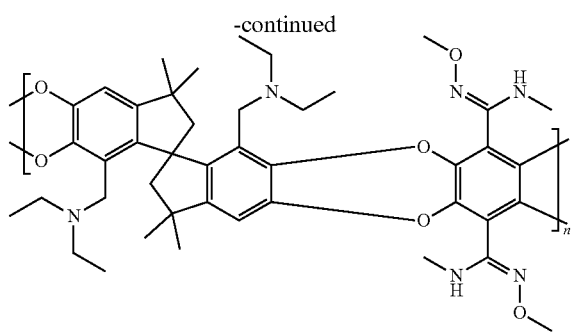

27

27: To a solution of 23 (1.50 g, 2.2 mmol) in dimethyl sulfoxide (43 mL) was added a solution of lithium hydroxide monohydrate (361 mg, 8.6 mmol) in MilliQ water (4 mL) dropwise over 1 min. After stirring for 1 h under nitrogen, the reaction mixture was placed on ice, and dimethyl sulfate (820 μL, 8.6 mmol) was added in two portions. The reaction was allowed to reach room temperature and stirred for 72 h, before quenching with 5 N sodium hydroxide (2 mL). The product was precipitated in MilliQ water (500 mL), filtered and rinsed with two portions of MilliQ water (100 mL each), followed by an additional precipitation from dimethyl sulfoxide into MilliQ water, and then dried in vacuo at 60° C. to give 27 as a dark yellow solid (940 mg) in 46% yield. $^1$H NMR (DMSO-$d_6$, 500 MHz): δ (ppm) 6.76 (br s, 2H), 5.82 (br s, 2H), 3.64 (br s, 4H), 2.91 (br s, 4H), 2.18 (br s, 20H), 1.32 (br s, 6H), 1.27 (br s, 6H), 0.69 (br s, 12H); SEC (DMF): $M_n$=6.9 kg mol$^{-1}$, $M_w$=13.8 kg mol$^{-1}$, PDI=1.99; BET Surface area: 8 m$^2$ g$^{-1}$. Pore-size distribution is shown in FIG. 9.

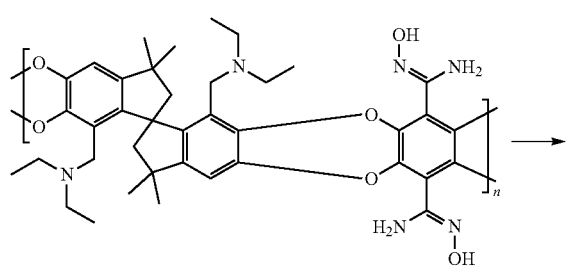

23

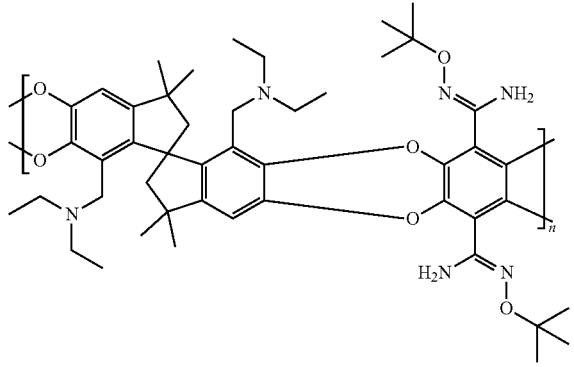

28

Figure 11:
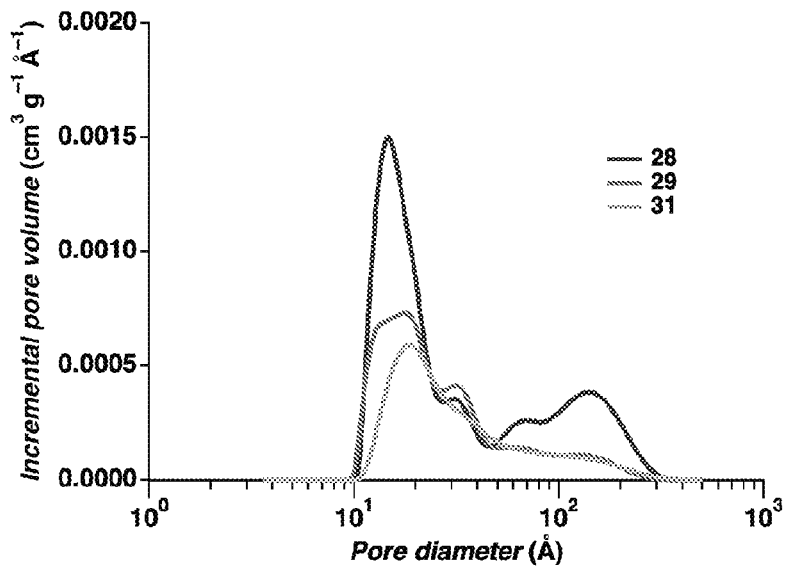
FIG. 11 shows the pore-size distribution of membranes fabricated from polymers 28, 29, and 31.

28: To a solution of 23 (1.5 g, 2.2 mmol) in dimethyl sulfoxide (43 mL) was added magnesium perchlorate (95 mg, 430 μmol) and di-tert-butyl dicarbonate (1.9 g, 8.6 mmol). The reaction was stirred for 24 h at 40° C., then cooled and precipitated in MilliQ water (430 mL) with a few drops of 5N sodium hydroxide and then filtered. The solid was rinsed with three portions of MilliQ water (50 mL each), and then two portions of chloroform (50 mL each) to remove excess di-tert-butyl dicarbonate, and then dried in vacuo at 60° C. to give 28 as a dark yellow solid (980 mg) in 49% yield. $^1$H NMR (DMSO-$d_6$, 500 MHz): δ (ppm) 6.80 (br s, 6H), 3.27 (br s, 4H), 2.93 (br s, 4H), 2.14 (br s, 8H), 1.37 (br m, 30H), 0.67 (br s, 12H); SEC (DMF): $M_n$=10.9 kg mol$^{-1}$, $M_w$=15.2 kg mol$^{-1}$, PDI=1.39; BET Surface area: 48 m$^2$ g$^{-1}$. Pore-size distribution is shown in FIG. 11.

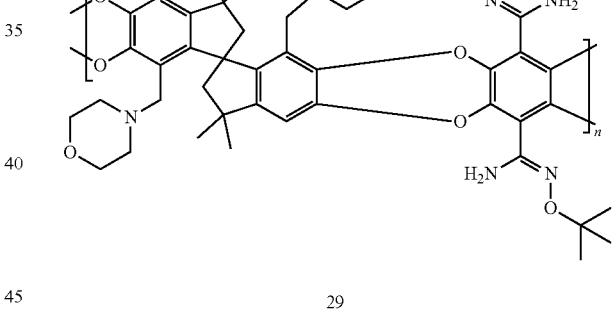

24

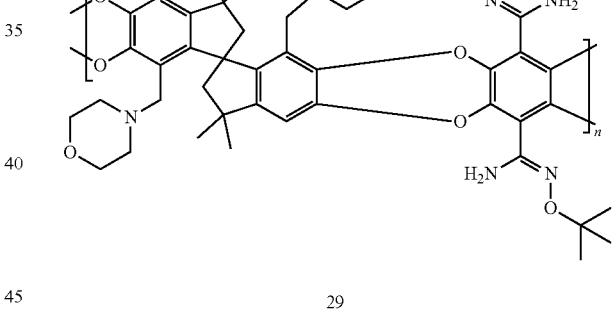

29

29: To a solution of 24 (1.5 g, 2.2 mmol) in dimethyl sulfoxide (43 mL) was added magnesium perchlorate (95 mg, 430 μmol) and di-tert-butyl dicarbonate (1.9 g, 8.6 mmol). The reaction was stirred for 24 h at 40° C., then cooled and precipitated in MilliQ water (400 mL) with a few drops of sodium hydroxide and then filtered. The solid was rinsed with three portions of MilliQ water (50 mL each), and then two portions of chloroform (50 mL each) to remove excess di-tert-butyl dicarbonate, and then dried in vacuo at 60° C. to give 29 as a dark yellow solid (1.2 g) in 56% yield. $^1$H NMR (DMSO-$d_6$, 500 MHz): δ (ppm) 6.84 (br s, 6H), 2.11 (br s, 24H), 1.14-1.55 (br m, 30H); SEC (DMF): $M_n$=43.0 kg mol$^{-1}$, $M_w$=137 kg mol$^{-1}$, PDI=3.19; BET Surface area: 31 m$^2$ g$^{-1}$. Pore-size distribution is shown in FIG. 11.

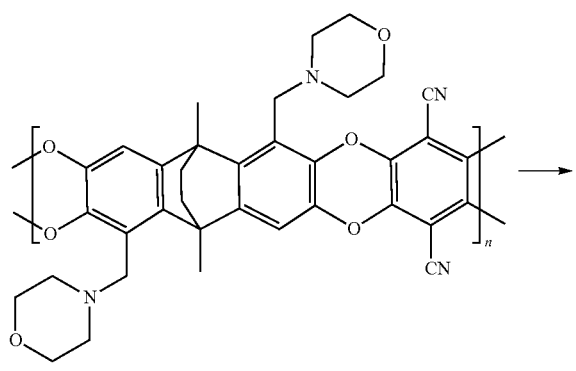

18

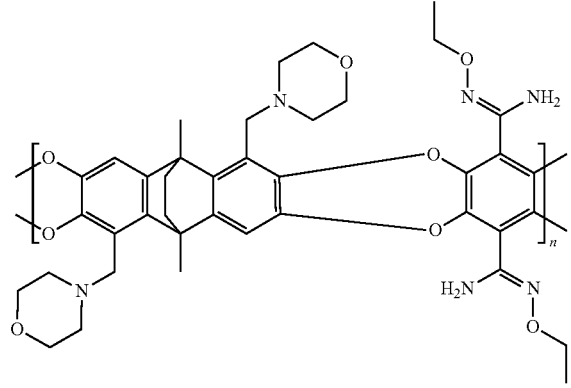

31

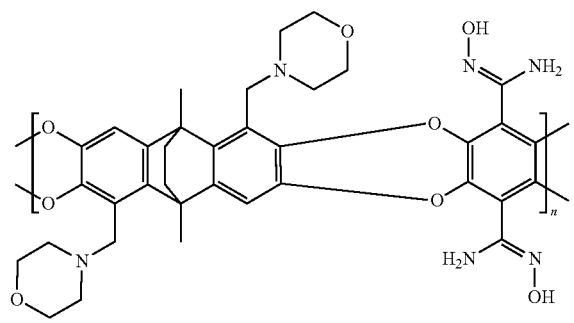

30

30: To a round bottom flask was added 18 (350 mg, 0.57 mmol) and tetrahydrofuran (22 mL). The mixture was heated to 70° C. to dissolve the polymer. A solution of 50 wt % aqueous hydroxylamine (2.623 mL, 39.7 mmol) was then added dropwise. The reaction was stirred for 72 h and then cooled before precipitating the polymer in methanol (120 mL). The solid was filtered and rinsed twice with methanol (50 mL) before drying in vacuo 50° C. to give 30 as a white powder (322.9 mg) in 82% yield. $^1$H NMR (DMSO-d$_6$, 500 MHz): δ (ppm) 9.57 (br s, 2H), 6.77 (br s, 4H), 5.83 (br s, 4H), 3.49 (br t, 8H), 2.23-1.33 (broad m, 22H); SEC (DMF): $M_n$=22.7 kg mol$^{-1}$, $M_w$=36.7 kg mol$^{-1}$, PDI=1.52; BET Surface area: 10 m$^2$ g$^{-1}$. Pore-size distribution is shown in FIG. 10.

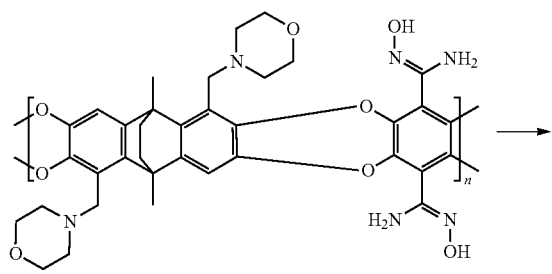

30

31: To a solution of 30 (200 mg, 0.32 mmol) in dimethyl sulfoxide was added lithium hydroxide monohydrate (53.4 mg, 1.27 mmol) in water (0.6 mL). The mixture was stirred for 1 h on ice before adding diethyl sulfate (0.164 mL, 1.27 mmol) and warming to room temperature. Reaction was stirred for two days, and then quenched by adding sufficient 5 N sodium hydroxide to increase the pH of the solution above 7. The polymer was precipitated in MilliQ water (100 mL) and then filtered, rinsed with an additional two portions of water (20 mL), and dried in vacuo at 50° C. to give 31 as a (231.2 mg) in 98% yield. $^1$H NMR (DMSO-d$_6$, 500 MHz): δ (ppm), 6.77 (br s, 4H), 6.05 (br s, 4H), 3.94 (br d, 4H), 3.48 (br s, 8H) 2.23-1.25 (broad in, 32H); SEC (DMF): $M_n$=16.6 kg mol$^{-1}$, $M_w$=41.9 kg mol$^{-1}$, PDI=2.54; BET Surface area: 24 m$^2$ g$^{-1}$. Pore-size distribution is shown in FIG. 11.

Example 4. Preparation of Microporous Polymer Membranes

Polymer inks were prepared in a suitable solvent, such as chloroform or NMP, at a concentration typically of 10-200 mg mL$^{-1}$. In certain cases, free-standing membranes were prepared in a desirable thickness from a user-defined volume of ink in a Teflon well under a crystallization dish, which aids in controlling the rate of solvent evaporation. Alternatively, freestanding membranes were cast onto a suitable substrate, such as glass, using a wet film applicator, such as a blade-coater. In such instances, glass substrates were prepared by washing with soap and water, followed by rinses with acetone and isopropanol, after which they were submerged in an aqueous bath of 0.1 M H$_2$SO$_4$ for a minimum of 12 h. Before membranes were cast, the glass substrates were quickly rinsed with deionized water to remove excess acid, pat-dried with lint-free wipers, and then placed on the bed of a blade coater heated to 40° C. Kapton tape was applied to the glass substrates to decrease ink migration. Ink was then applied within the well before it was blade coated at a 50-200 µm height. The ink was covered with a crystallization dish and left on the heated bed of the blade coater until it was no longer tacky (~16 h). The heated bed was turned off and the membrane was allowed to reach room temperature before being placed in a bath of Milli-Q water for delamination. All membranes were soaked overnight in the appropriate electrolyte before use.

Example 5. Preparation of Microporous Polymer Coated Separators

Thin films of microporous polymers on porous supports, such as a polyolefin battery separator (e.g., Celgard), can be prepared using a wet film applicator, such as an Elcometer 4340 Automatic Film Applicator. Inks of the polymers (25-500 mg mL$^{-1}$) were prepared in a suitable solvent, such as chloroform. An appropriate volume of ink was deposited onto the polyolefin battery separator and then applied across the separator surface as a thin film with an Elcometer wire-wound rod with a user-defined wet film height specification, typically 20 µm. The thickness of the polymer layer can be determined using a variety of methods, such as cross-sectional SEM, and thicknesses determined were typically 0.5-5 µm, depending on the choice of polymer and solvent, the concentration of polymer in the solvent, the viscosity of the ink, the wet film height specification, and other experimental parameters.

Figure 12:
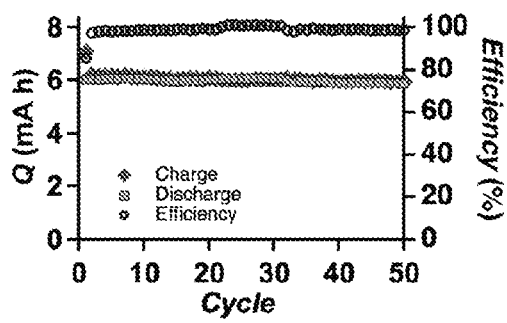
FIG. 12 shows charge, discharge, and efficiency curves for an aqueous electrochemical cell implementing a metallic Zinc anode, an organic cathode dissolved in electrolyte, and a separator fabricated with polymer 19.
Figure 13:
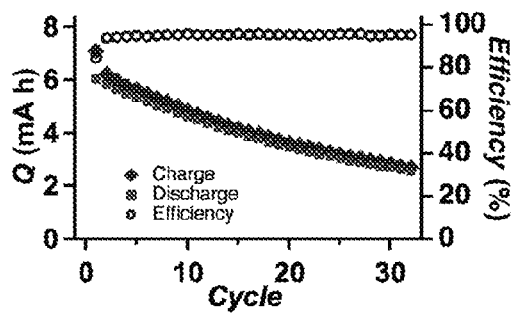
FIG. 13 shows charge, discharge, and efficiency curves for an aqueous electrochemical cell implementing a metallic Zinc anode, an organic cathode dissolved in electrolyte, and a Nafion 212 separator.
Figure 14:
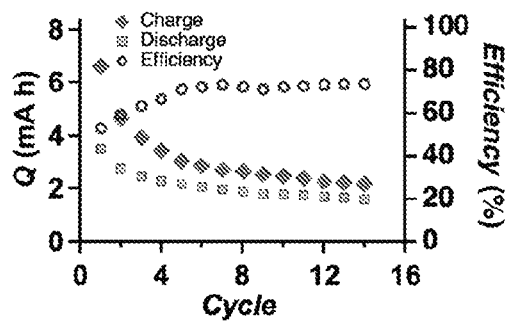
FIG. 14 shows charge, discharge, and efficiency curves for an aqueous electrochemical cell implementing a metallic Zinc anode, an organic cathode dissolved in electrolyte, and a Celgard 3501 separator.

Example 6. Aqueous Electrochemical Cells Implementing a Metallic Zinc Anode Alongside an Organic Cathode Dissolved in Electrolyte An interchangeable membrane glass H-cell was employed for battery testing. A membrane of 19 with a thickness of 90-100 µm was soaked in a solution of 1.0 M ammonium chloride overnight and then placed in between the two compartments. The catholyte was composed of aqueous 0.035 M sodium (2,2,6,6-tetramethylpiperidin-1-yl)oxyl-4-sulfate and 1.73 M ammonium chloride, with a reticulated vitreous carbon current collector. The anolyte was composed of aqueous 0.5 M zinc chloride and 1.0 M ammonium chloride, with a zinc foil current collector, cut to 1×2 cm and pre-treated with 1.0 M hydrochloric acid. 8.53 mL of electrolyte were added to each compartment, for a theoretical capacity of 8.0 mA h. The battery was cycled at a rate of C/4, with a current density of 0.5 mA cm$^{-2}$ with respect to the anode, at room temperature, in an inert argon atmosphere. See FIG. 12 for 19 as separator, FIG. 13 for a Nafion 212 as separator, and FIG. 14 for Celgard 3501 as separator.

Figure 15:
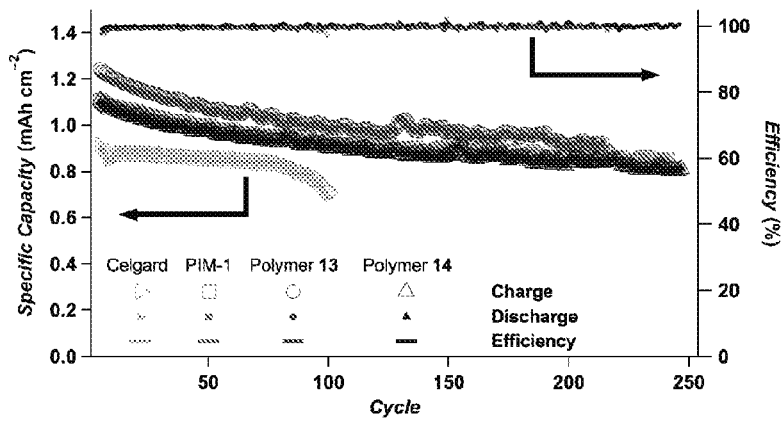
FIG. 15 shows charge, discharge, and efficiency curves for Li-NMC-622 cells using polymer 13, polymer 14, or PIM-1 interlayers on metallic Lithium anodes, or no interlayer (i.e., Celgard only).

Example 7. Electrochemical Cells Implementing a Metallic Lithium Anode Coated with a Microporous Polymer Interlayer Alongside a Composite Cathode CR2032 coin cells were assembled with a single spacer and spring pressed at 1000 psi, Celgard 2535 separators, 70 µL of liquid electrolyte (1.0 M LiPF$_6$ in EC:DMC (1:1) with 10% w/w fluoroethylene carbonate (FEC) and 1% w/w vinylene carbonate (VC)) and standard Li electrodes onto which PIMs were cast as inks in tetrahydrofuran (12.5 mg mL$^{-1}$), which were dried overnight before cell assembly. Li-NMC-622 cells were assembled with PIM-1, 13, or 14 cast onto 1.5-mm thick Li anodes (40 µL of ink, yielding ~15 µm-thick overlayers) alongside NMC-622 (LiNi$_{0.6}$Mn$_{0.2}$Co$_{0.2}$O$_2$) cathodes with areal capacity of 1.44 mAh cm$^{-2}$. Cycling was carried out at 25° C. with three initialization cycles at 0.1 mA cm$^{-2}$ before cycling at 1 mA cm$^{-2}$ until 70% of the initial capacity was observed. See FIG. 15 for cycling data for Li-NMC-622 cells using 13 and 14 as interlayers on Li, which access higher capacity than cells configured with no interlayer (i.e., Celgard only) and, in the case of interlayer 13, than cells configured with a positive control polymer, PIM-1.

Example 8. Neutral and Cation Exchange Membranes from Polymers of Intrinsic Microporosity for Crossover-Free Aqueous Electrochemical Devices Chemical Stability of Amidoximes and Structural Rigidity of Ladder Polymers can be Leveraged to Counteract Membrane Degradation at High pH. Aqueous alkaline electrochemical cells present formidable challenges for membrane stability and conductivity as well as transport selectivity for active materials and working ions for a given cell chemistry. With respect to stability, many organic functional groups (e.g., imides, benzimidazoles, quaternary ammoniums, phosphoniums, etc.) integrated into polymer membranes can be hydrolyzed or undergo elimination reactions at high pH. Such chemical transformations are often deleterious to membrane performance. In most cases, the conductivity of the membrane will evolve with the extent of transformation, as will the transport selectivity. In extreme cases, the membrane's pores collapse, which has been attributed to unintended hydrogen bonding or ion pairing between complementary functional groups newly generated along the polymer backbone (e.g., carboxylate-ammonium bridges), or to changes in conformational and configurational entropy of the polymer backbone (e.g., due to benzamide or benzimidazole ring-opening). The present studies are based on the hypothesis that alkaline-stable, ionizable functionality should be placed along the polymer backbone, rather than be a part of it, and that the backbone should have characteristically low conformational and configurational entropy (i.e., be endowed with structural rigidity) to avoid changes in packing across a broad range of pH or in response to adventitious chemical degradation. To meet the demands for working-ion conduction in many aqueous alkaline batteries, it is also desirable for the ionizable functionality to be anionic at high pH to afford cation exchange membranes.

Figure 16A:
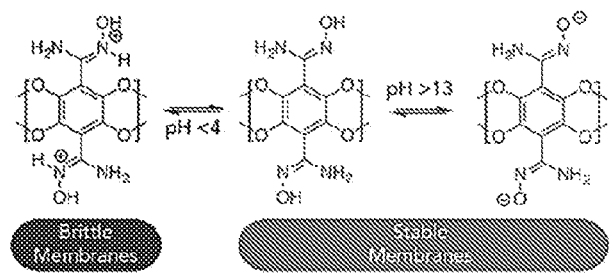
FIG. 16A shows a summary of AquaPIM membrane ionization across the spectrum of pH commonly encountered in aqueous electrochemical cells.

Amidoximes have unique characteristics that are useful for addressing the instability of chemical functionality appended to polymer backbones, used to promote membrane swelling and fast ion transport. Amidoximes are polar and ionizable at both low- and high pH (pK$_{a1}$~4.5 and pK$_{a2}$~13.3): at pH<4, they are cationic; at pH 5-13, they are primarily charge-neutral; and at pH>13, they are anionic (FIG. 16A). Such functionality grants expansive opportunities for cation exchange membrane development at high pH. Prior to their use, described herein, as pore-lining chemical functionality in microporous polymer membranes for electrochemical devices, amidoxime-based polymeric materials have been previously implemented in gas separations and in extracting lanthanides and actinides from processed ores, where their stability at pH>13 is a strict requirement.

To address the structural rigidity of the polymer backbone, an architectural platform based on ladder polymers was designed, where conformational and configurational entropy are low and where intrinsic microporosity can be high (10-30%), relative to other classes of polymers (e.g., cellulosics, polysulfones, polyamides, polyimides, polyolefins, etc.). Such ladder polymers are often referred to as polymers of intrinsic microporosity (PIMs). PIMs derive their unique sub-nm interconnected porosity from the frustrated packing of polymer chains in the condensed phase, which arises from primarily two macromolecular design characteristics: 1) severely restricted conformational degrees of freedom available to the polymer chain, through the incorporation of spirocyclic or polycyclic monomers into the main chain, or, alternatively, monomers whose bonds are hindered with respect to rotation (e.g., ortho-substituted arenes, atropisomers, etc.); and 2) persistent kinks along the main chain, in either 2D or 3D, depending on the nature of the site(s) of contortion embodied by the monomer(s).

By appending ionizable and high pH-stable amidoximes onto microporous ladder polymer backbones as described herein, a new family of aqueous-compatible polymers of intrinsic microporosity, or AquaPIMs, has been developed.

These materials serve effectively as ion-selective membranes in aqueous electrochemical devices. The studies described herein illustrate the foundational stability-conductivity-selectivity relationships for membranes that vary in the types and prevalence of both 2D and 3D contortion sites along the polymer backbone, as well as the state of ionization of the amidoxime in aqueous electrolytes spanning pH 4.5-15, with the high-pH extreme consisting of 40% aqueous KOH (w/w). The behavior of these new materials is contrasted with the behavior of two commercially available membranes: non-selective, mesoporous Celgard 3501 separators and ion-selective Nafion 212 membranes.

Figure 16B:
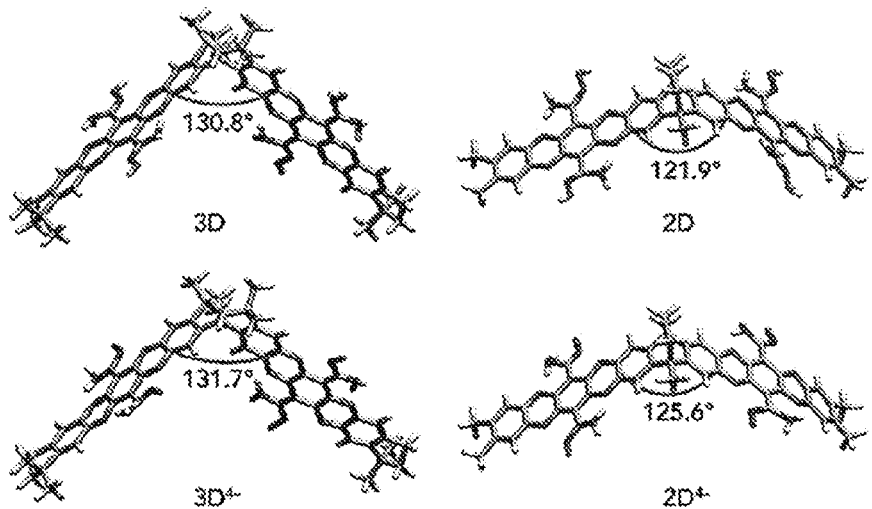
FIG. 16B shows the optimal configurations from quantum mechanical calculations of 3D (spirocyclic) and 2D (bridged bicyclic) contortion sites showing that protonation state has negligible impact on the contortion angle.
Figure 16C:
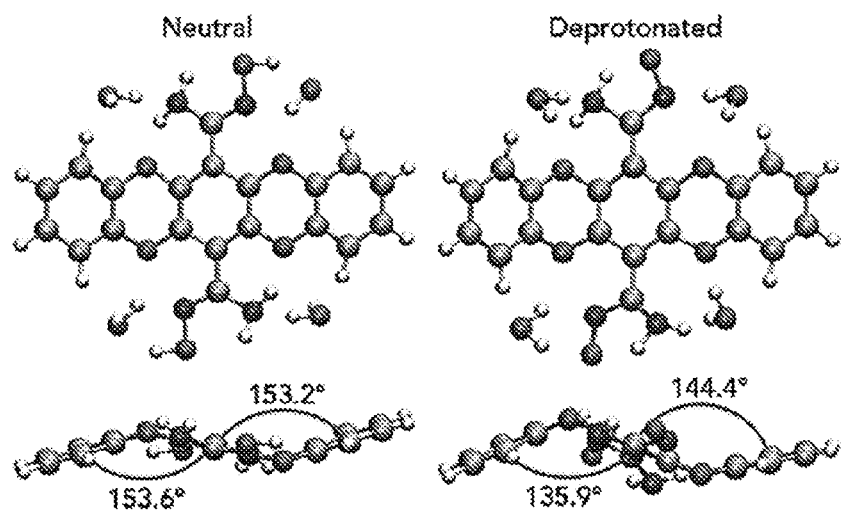
FIG. 16C shows configurations obtained from quantum mechanical calculations showing the effect of interactions between amidoximes and water on dibenzodioxane rigidity.

To demonstrate that the amidoxime functionality allows for the formation of stable pores under alkaline conditions, the optimal structures of bridged bicyclic (2D) and spirocyclic (3D) dimers were explored in various states of deprotonation, and the free energy landscape was assessed for chain flexibility for both 2D- and 3D-contortion sites using quantum mechanical calculations and classical molecular dynamics (FIG. 16B). Optimal configurations of these contortion sites (FIG. 16B) show only subtle changes in backbone dihedral angles as a function of the state of deprotonation (~1° and ~4° for the spirocyclic and the bridged dimers, respectively). Both absolute dihedral angles and their changes with deprotonation were well reproduced in classical molecular dynamics simulations with explicit consideration of a high pH (~2.3 M aqueous solution of NaOH). In the absence of ionic and dielectric screening, the center-of-mass separation of dimer branches increases, upon deprotonation, by ~3 Å (from 11.6 Å to 14.5 Å) and ~1 Å (from 13.2 Å to 14.4 Å) for the spirocyclic and the bridged bicyclic dimers, respectively (FIG. 16F). Additional quantum mechanical studies revealed flexibility of the dimer branches caused by changes in the electronic structures of the amidoxime groups induced by explicit, hydrogen-bonded water molecules (FIG. 16C). However, classical MD simulations showed no significant changes of the average branch separations due to ionic screening. With the actual separation between the dimer branches being ~10 Å or more, at high pH, the centers of charge in the amidoxime groups are effectively decoupled due to the very short Debye screening length (<2 Å), which explains the insensitivity of the dimer structures to different states of deprotonation.

Figure 16D:
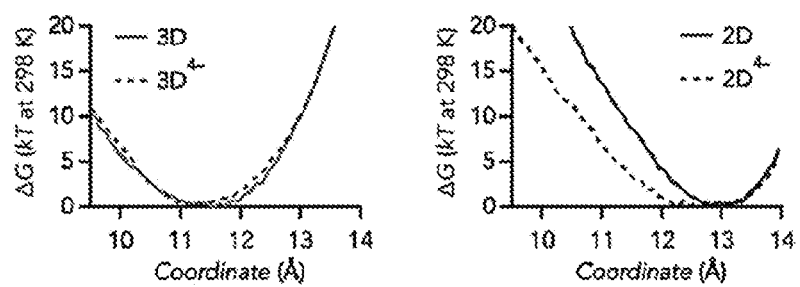
FIG. 16D shows free-energy profiles of the 3D (spirocyclic) and 2D (bridged bicyclic) contortion sites in the neutral and fully deprotonated states. The "Coordinate" refers to the distance between the centers of the two amidoxime functionalized phenyl rings.
Figure 16E:
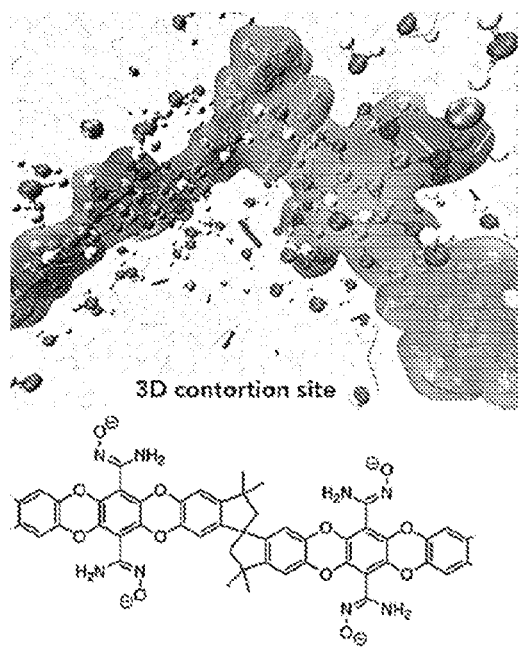
FIG. 16E shows molecular representations of 3D AquaPIM contortion sites, with electrostatic surfaces denoted, and the first solvation shells indicated with ball-and-stick water molecules.
Figure 16F:
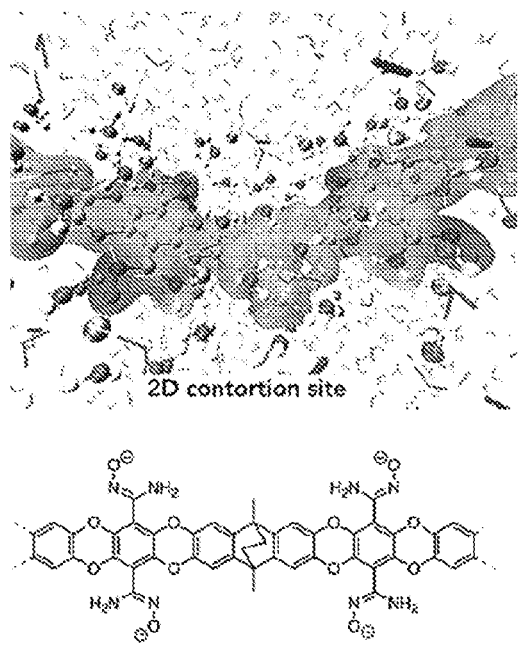
FIG. 16F shows molecular representations of 2D AquaPIM contortion sites, with electrostatic surfaces denoted, and the first solvation shells indicated with ball-and-stick water molecules.

To understand the likelihood for pore network reconfigurability at different pH (and therefore degree of amidoxime ionization), the free energy was calculated as a function of center-of-mass separation of dimer branches for each dimer in the neutral and fully deprotonated states (FIG. 16D). Due to the difference in the mutual orientation of the branches in the 2D and 3D dimers, the equilibrium separations are slightly different, yet largely independent of the degree of ionization. The curvatures of the free-energy profiles at the equilibrium separations reflect the overall softness of dimers, mostly related to the bending of the dimer branches. To change the equilibrium separation between branches by ~±1.5 Å requires ~10 $k_BT$ of free energy at room temperature; however, it was found that further changes require modification to the dihedral angles at the contortion sites, making such changes highly unlikely. As a result, the proposed polymer structures appeared sufficiently rigid to maintain porosity under both neutral and highly alkaline conditions.

Figure 17A:
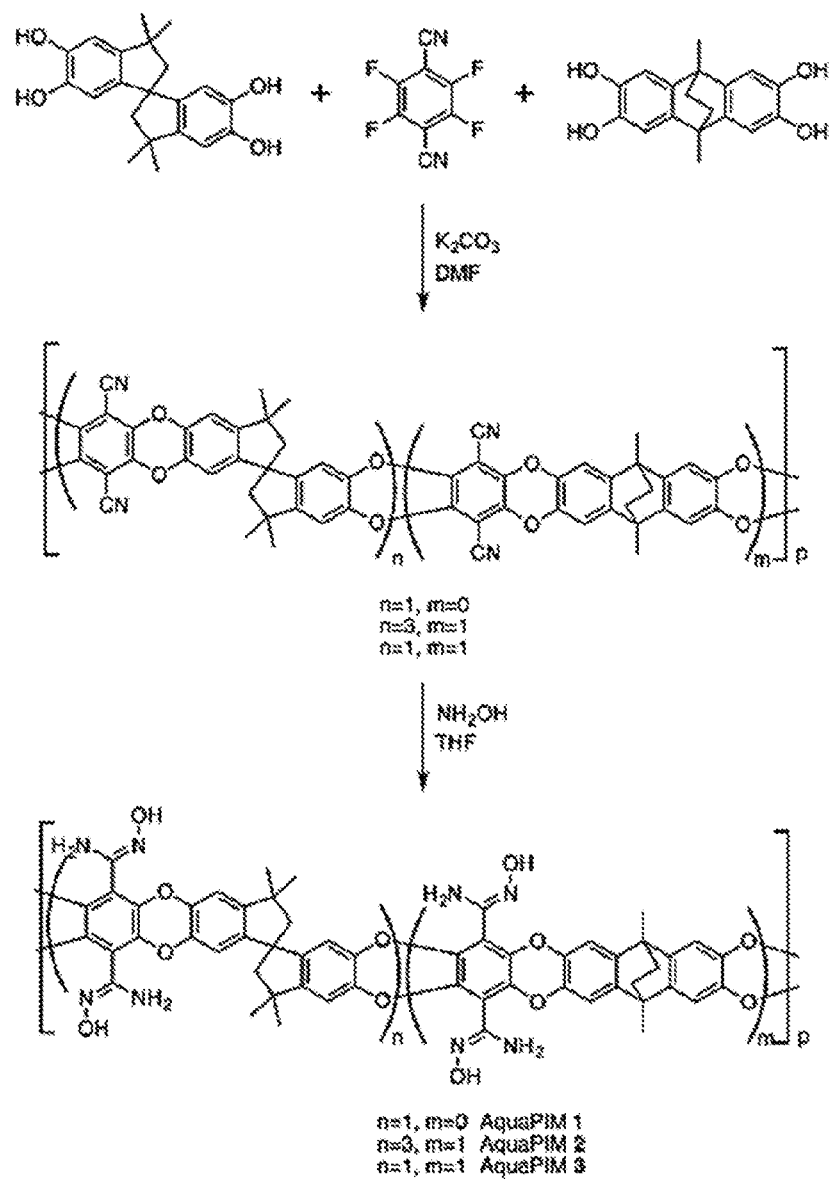
FIG. 17A shows Synthetic scheme for the synthesis of AquaPIMs 1-3. The proportion of spirocyclic and bridged bicyclic biscatechol monomers are varied to diversify the membrane pore architectures. Notably, the amidoxime functionality is introduced in a quantitative, post-polymerization modification.

To explore the impact of a given monomer's contortion-site geometry and occurrence on the properties of AquaPIM membranes, amidoxime-functionalized AquaPIMs 1-3 were synthesized using a high-yielding, scalable two-step sequence (FIG. 17A). Here, tetrafluoroterephthalonitrile was polymerized under basic conditions in DMF with varying proportions of bridged bicyclic and spirocyclic biscatechol monomers, which feature 2D and 3D contortion sites, respectively. Then, the cyano groups on the polymers were quantitatively interconverted to amidoximes using hydroxylamine under refluxing conditions, yielding AquaPIMs 1-3. While AquaPIMs 1-3 were soluble polymers, suitable for casting membranes, those incorporating more than 50I% of the bridged bicyclic monomer were not immediately; therefore, the analysis detailed below was restricted to these three.

Figure 17B:
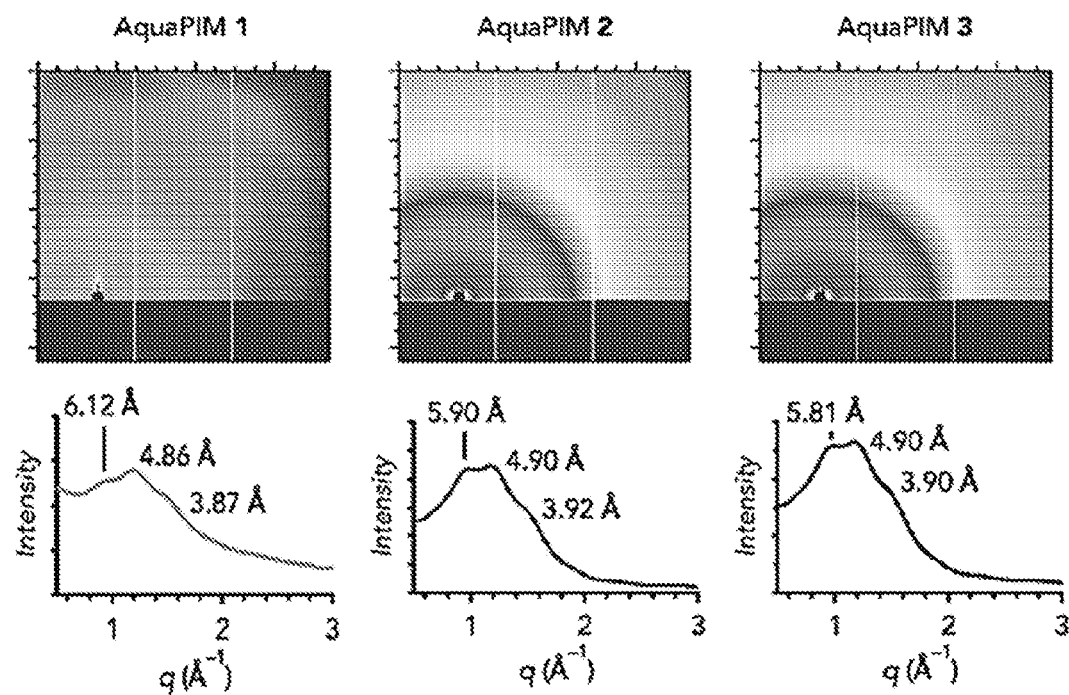
FIG. 17B shows Grazing-incidence wide-angle x-ray scattering of AquaPIMs 1-3.
Figure 17C:
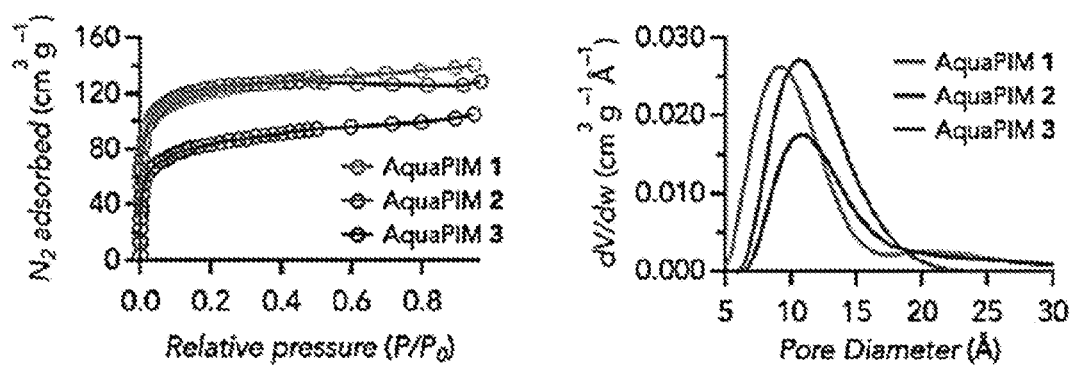
FIG. 17C shows Nitrogen adsorption isotherms and pore-size distributions for AquaPIMs 1-3. Pore-size distributions are modeled from the adsorption data using NLDFT.

To understand the pore-size distribution of AquaPIMs 1-3, $N_2$ (FIG. 17C) and $CO_2$ (data not shown) adsorption isotherms were collected. Pronounced $N_2$ adsorption at low pressure reveals intrinsic microporosity (pores <20 Å) in all three polymers. NLDFT pore size distributions fit to these data reveal how the spirocyclic and bridged bicyclic biscatechol residues direct pore architecture. When exclusively spirocyclic residues are present in AquaPIM 1, a high surface area of 454 $m^2$ $g^{-1}$ and pores approximately 8.6 Å wide are observed. As bridged bicyclic residues are introduced into the polymer backbone in AquaPIM 2, an increase in pore size to 10.5 Å was observed, while the surface area was very similar (472 $m^2$ $g^{-1}$). Further increasing the proportion of bridged bicyclic residues into AquaPIM 3 led to a loss of surface area, to only 309 $m^2$ $g^{-1}$, without any change in pore size (10.5 Å pores). Ultra-microporosity (pores <7 Å) was also observed in the gas uptake in the low-pressure regions of the $CO_2$ isotherms, which showed similar porosity for all three polymers in this size regime, at ~5.6 Å.

Further investigation of the pore structure was undertaken using grazing-incidence wide-angle x-ray scattering (GI-WAXS) before (data not shown) and after (FIG. 17B) the introduction of the amidoxime functionality. Prior studies on PIM WAXS patterns indicate that a broad, low-q scattering feature peaking below 0.5 $Å^{-1}$ is indicative of microporosity. A broad scattering feature at q~1-1.1 $Å^{-1}$ (4.9-6.1 Å in real-space) was observed for AquaPIMs 1-3. By comparison, hydrophobic PIMs 1-3 exhibited a scattering feature at q~0.6 $Å^{-1}$ (9.8-10.8 Å in real-space), as well as peaks at larger q, which track those observed for the AquaPIMs. The lack of low-q intensity in the AquaPIM scattering patterns suggested that the polymer network was more densely packed than some other PIMs, which was expected given the hydrogen bond accepting and donating nature of amidoxime groups. This microstructural analysis of the pore network was consistent with that obtained from the $N_2$ adsorption experiments.

The architectural attributes for AquaPIMs 1-3 take form as a microporous polymer membrane for aqueous electrochemical devices by solvent casting, since the $T_g$ for PIMs is higher than their temperature of decomposition (i.e., PIMs are not thermally processable). Both freestanding and supported membranes were prepared using solvent-casting techniques from inks formulated in N-methyl-2-pyrrolidone (100-300 mg $mL^{-1}$). Of the three polymers, membranes cast from AquaPIM 1 were the most robust to handling for a wide range of electrolyte formulations and membrane thicknesses, on or off a support such as Celgard 3501. It was noted that membranes from AquaPIMs 1-3 were brittle after equilibration in harshly acidic electrolytes (pH<4), while under mildly acidic (1.0 M $NH_4Cl$, pH 4.5) to extreme alkaline (40% w/w KOH) conditions, the membranes were handled easily. Hydrogen bonding preferences for pendant amidoximes at various states of ionization are likely responsible for the observed differences in brittleness (FIG. 16A).

To confirm the chemical stability of the polymer membranes after equilibration in highly alkaline media, FT-IR and $^1$H NMR spectroscopic analysis was conducted for each membrane, and strikingly similar spectral features for membranes soaked in either deionized water or 40% aqueous KOH (w/w) were observed.

Figure 18A:
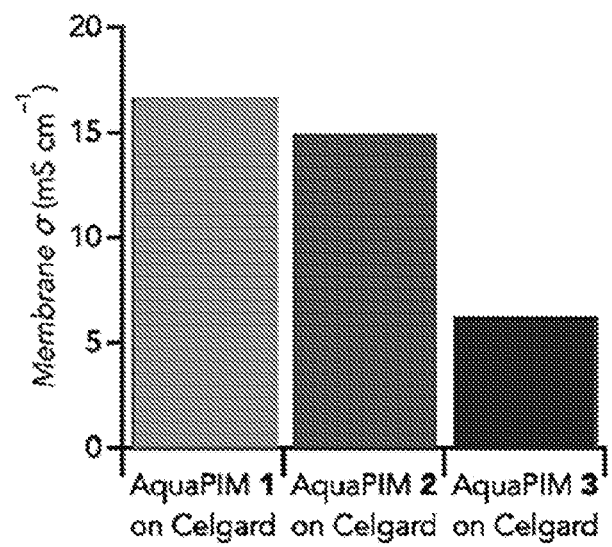
FIG. 18A shows membrane ionic conductivity (σ) for AquaPIMs 1-3 supported on Celgard 3501 as measured in 40% aqueous KOH (w/w).

Ionizability of Amidoximes at High pH Amplifies the Ionic Conductivity of AquaPIM Membranes. To quantify the membrane ionic conductivity for AquaPIMs 1-3 in highly alkaline aqueous electrolyte, supported membranes were equilibrated in 40% aqueous KOH (w/w) and assembled in custom-purposed Swagelok cells without additional electrolyte. Analysis of the Nyquist plots obtained by electrochemical impedance spectroscopy (EIS) of these cells allowed for the resistance of the AquaPIM overlayer to be extracted, after subtracting the contribution from the underlying Celgard 3501 support (FIG. 18A). The intrinsic membrane ionic conductivity was then calculated by considering the thickness of the AquaPIM overlayer: σ values of 16.7, 15.0, 6.3 mS cm$^{-1}$ differentiated the transport properties of AquaPIMs 1-3, respectively. The observed changes were consistent with the relative pore architecture of the three polymers (FIG. 17C), which are evidently dictated by the ratio of 2D and 3D monomers incorporated into the polymer chains. While all three polymers exhibited high conductivity under these conditions, AquaPIM 1 membranes were particularly promising for direct comparison to other membranes, considering their ease of processability and superior mechanical integrity.

Figure 18B:
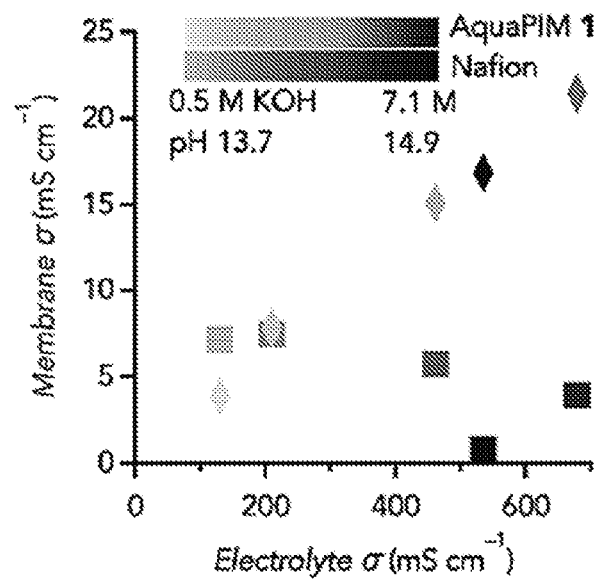
FIG. 18B shows membrane ionic conductivity (σ) for freestanding AquaPIM 1 as measured in 0.5 M, 1.0 M, 2.5 M, 5.0 M, and 7.1 M aqueous KOH.
Figure 18C:
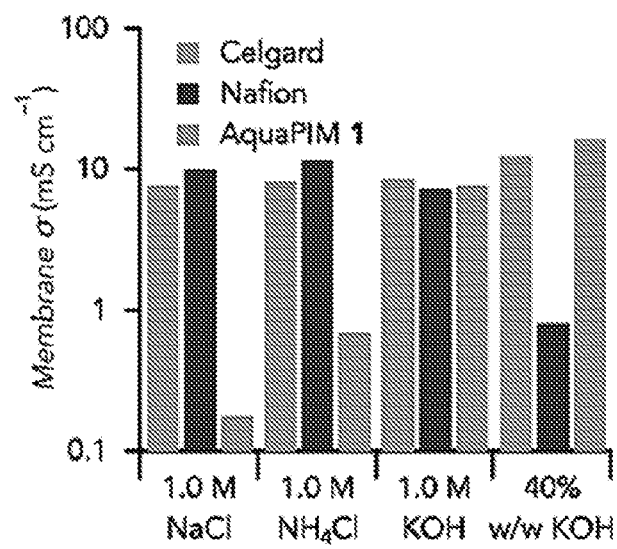
FIG. 18C shows membrane ionic conductivity (σ) for freestanding AquaPIM 1 as measured in 1.0 M NaCl, 1.0 M $NH_4Cl$, 1.0 M KOH, and 40% aqueous KOH (w/w), relative to mesoporous Celgard 3501 and Nafion 212 ion-exchange membranes.

The ionic conductivity of AquaPIMs 1-3 in aqueous alkaline electrolyte is on par or higher when compared to other polymer membranes—however, most of these membranes have been developed as anion-exchange membranes for fuel cells and other devices. The intentional design of AquaPIMs as cation exchange membranes begins to resolve technology gaps for polymer membranes suitable for use in aqueous alkaline electrochemical devices, where the working ions are cations rather than hydroxide or chloride. This led to the further consideration of the foundations for ion transport by AquaPIM 1 in other aqueous electrolytes, which was studied by varying the chemical identity of the supporting salt as well as pH, all of which influence the extent of ionization of the amidoxime and in turn the structure and dynamic properties of water and ions confined to amidoxime-lined pores at the sub-nm scale. The ionic conductivity for free-standing AquaPIM 1 membranes (~100 μm) was evaluated for infiltrating electrolytes consisting of 1.0 M NaCl, 1.0 M NH$_4$Cl, 0.5 M KOH, 1.0 M KOH, 2.5 M KOH, 5.0 M KOH, and 40% aqueous KOH (w/w) (FIGS. 18B and C) from Nyquist plots obtained by EIS as described above. These data were also acquired for Celgard 3501 separators as well as Nafion 212 membranes for comparison. For mesoporous Celgard 3501, which wets but does not swell in aqueous electrolytes, a monotonic increase was observed in the separator ionic conductivity with increasing ionic conductivity of the electrolyte, as expected. On the other hand, for Nafion 212, there was an initial increase in membrane ionic conductivity with increasing electrolyte ionic conductivity (i.e., for 1.0 M NaCl, 1.0 M NH$_4$Cl, and 1.0 M KOH electrolytes), but also a notable decrease in conductivity when infiltrated with alkaline electrolytes (FIG. 18B). The determinations of the membrane ionic conductivity of Nafion 212 in aqueous alkaline electrolytes are consistent with measurements elsewhere.

There have been several explanations postulated for the observed behavior: the partitioning of ions in the electrolyte does not track the bulk electrolyte for high KOH concentrations: the increased ionic strength more effectively screens the repulsive interactions between the perfluoroalkylsulfonates, constricting the membrane's pores, the dynamics of water and ions in the pores are comparably slow for concentrated liquid electrolytes; or, the low degree of phase separation in the KOH resulting in fewer regions of high hydrophillicity to allow for ion shuttling. Contrasting this behavior. AquaPIM 1 membranes exhibit their highest membrane ionic conductivity for electrolytes whose pH is greater than the pK$_a$ of the amidoxime (FIGS. 18B and C). Thus, while AquaPIM 1's membrane ionic conductivity is 0.18 mS cm$^{-1}$ for the 1.0 M NaCl electrolyte and 0.70 mS cm$^{-1}$ for the 1.0 M NH$_4$Cl electrolyte, its conductivity jumps orders of magnitude to 7.9 mS cm$^{-1}$ for the 1.0 M KOH electrolyte and advances further to 21.5 mS cm$^{-1}$ at 5.0 M KOH, and eventually backtracks to 16.9 mS cm$^{-1}$ in 40% aqueous KOH (w/w) due to its high viscosity. AquaPIM conductivity therefore quickly meets and eventually exceeds that of Nafion 212 with increasing KOH in the electrolyte. The resilience of AquaPIM 1 membranes to both high pH and high ionic strength suggests more effective partitioning of ions from the concentrated liquid electrolyte into the membrane's network of pores, less pore constriction, and more favorable dynamics of water and ions in the pore network compared to Nafion 212. This further indicates that sub-nm porous AquaPIM 1 membranes may be well-suited to serve as membranes in aqueous electrochemical devices requiring high conductivity and high transport selectivity for working ions over active materials.

Figure 19:
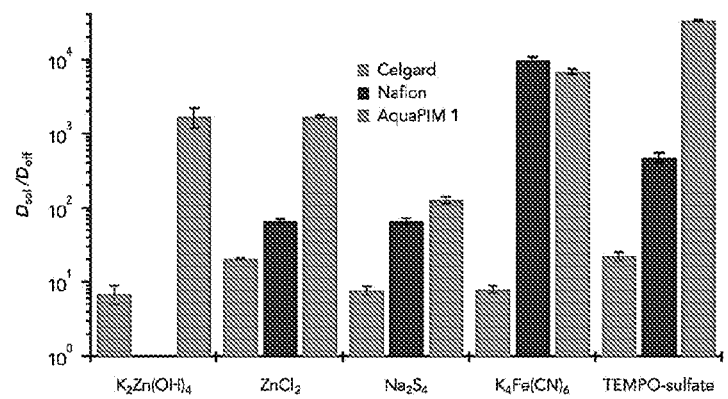
FIG. 19 shows a quantification of the extent to which AquaPIM 1, Celgard 3501, and Nafion 212 membranes restrict the diffusive transport of various battery active materials in aqueous electrolytes. Higher ratios for a given active material's diffusive permeability in the membrane ($D_{eff}$) to its diffusion in electrolyte ($D_{sol}$) indicate better blocking by a given membrane. AquaPIM 1 outperforms both commercial membranes for most active materials, often by orders of magnitude for this figure of merit.
Figure 20A:
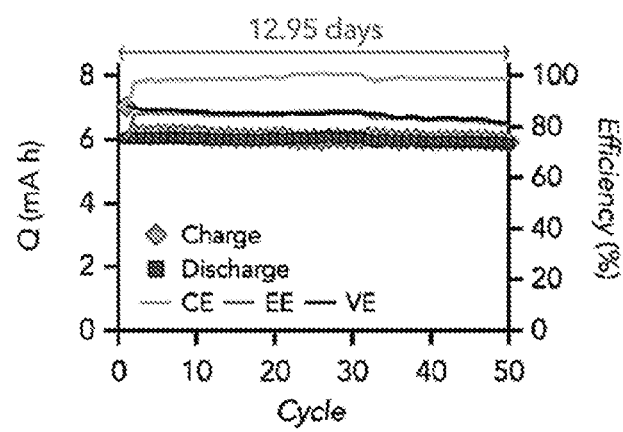
FIG. 20A shows charge and discharge capacity (Q) with corresponding Coulombic efficiency (CE), energy efficiency (EE), and voltage efficiency (VE) for Zn-TEMPO-sulfate battery cells configured with AquaPIM 1 membranes. Theoretical capacity=8 mA h.
Figure 20B:
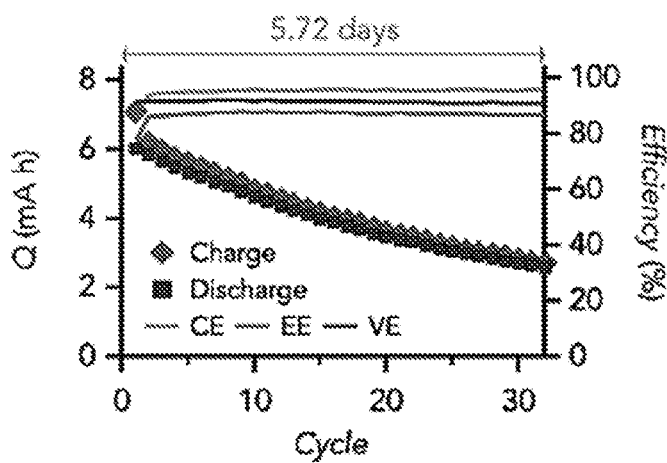
FIG. 20B shows charge and discharge capacity (Q) with corresponding Coulombic efficiency (CE), energy efficiency (EE), and voltage efficiency (VE) for Zn-TEMPO-sulfate battery cells configured with Nafion 212 membranes. Theoretical capacity=8 mA h.
Figure 20C:
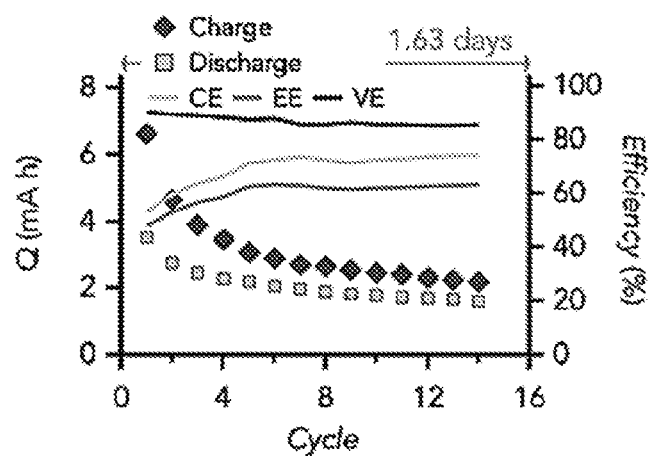
FIG. 20C shows charge and discharge capacity (Q) with corresponding Coulombic efficiency (CE), energy efficiency (EE), and voltage efficiency (VE) for Zn-TEMPO-sulfate battery cells configured with Celgard 3501 membranes. Theoretical capacity=8 mA h.
Figure 20D:
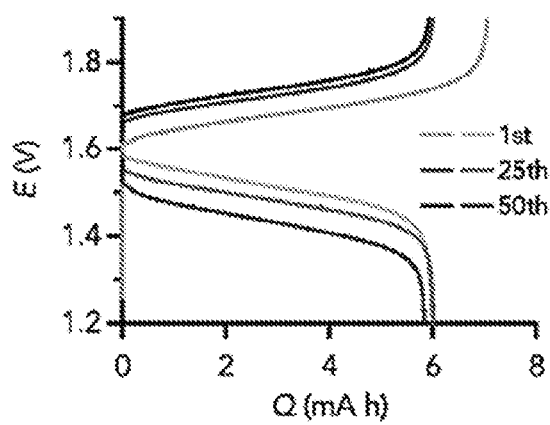
FIG. 20D shows charge and discharge curves of the first, middle, and last cycles for Zn-TEMPO-sulfate battery cells configured with AquaPIM 1 membranes.
Figure 20E:
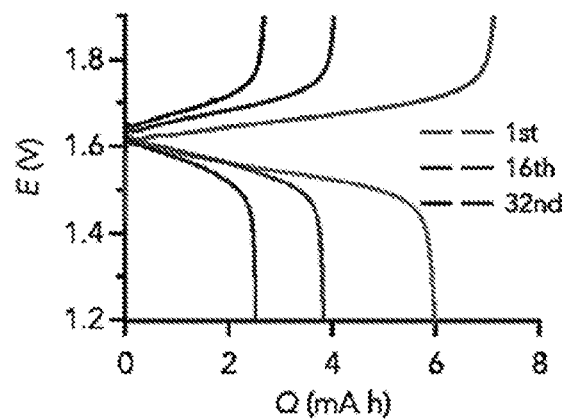
FIG. 20E shows charge and discharge curves of the first, middle, and last cycles for Zn-TEMPO-sulfate battery cells configured with Nafion 212 membranes.
Figure 20F:
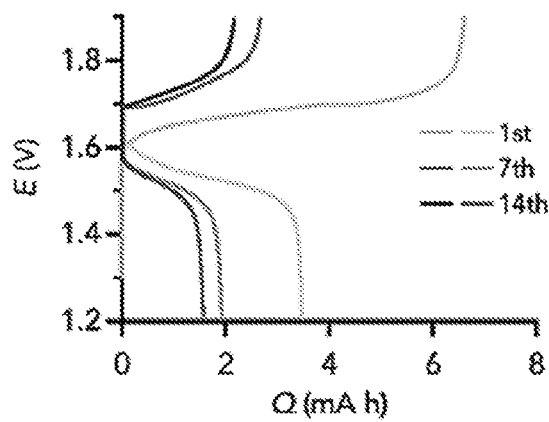
FIG. 20F shows charge and discharge curves of the first, middle, and last cycles for Zn-TEMPO-sulfate battery cells configured with Celgard 3501 membranes.
Figure 21A:
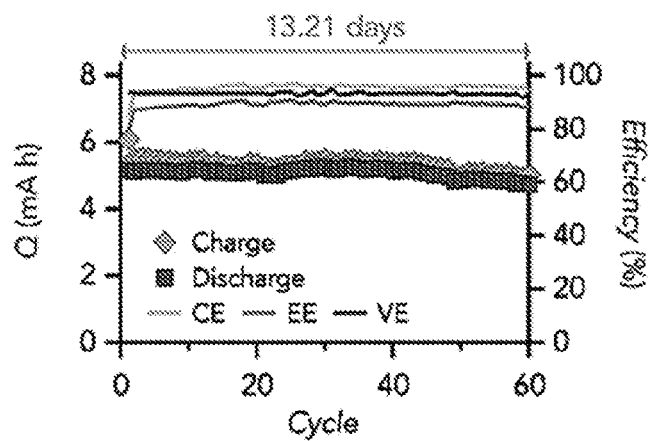
FIG. 21A shows charge and discharge capacity (Q) with corresponding Coulombic efficiency (CE), energy efficiency (EE), and voltage efficiency (VE) for Zn—$K_4Fe(CN)_6$ battery cells configured with AquaPIM 1 membranes. Theoretical capacity=8 mA h.
Figure 21B:
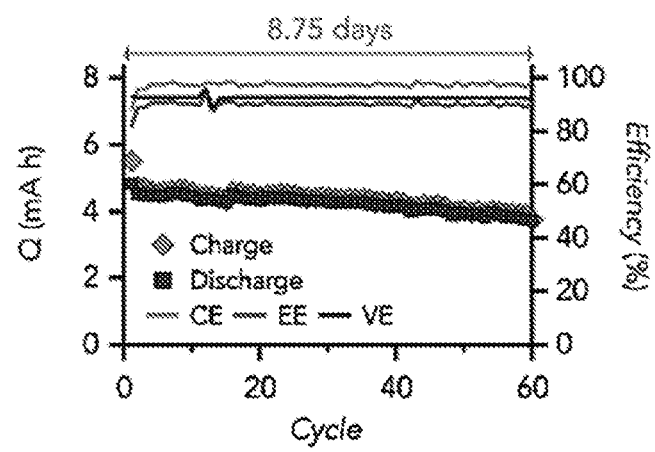
FIG. 21B shows charge and discharge capacity (Q) with corresponding Coulombic efficiency (CE), energy efficiency (EE), and voltage efficiency (VE) for Zn—$K_4Fe(CN)_6$ battery cells configured with Nafion 212 membranes. Theoretical capacity=8 mA h.
Figure 21C:
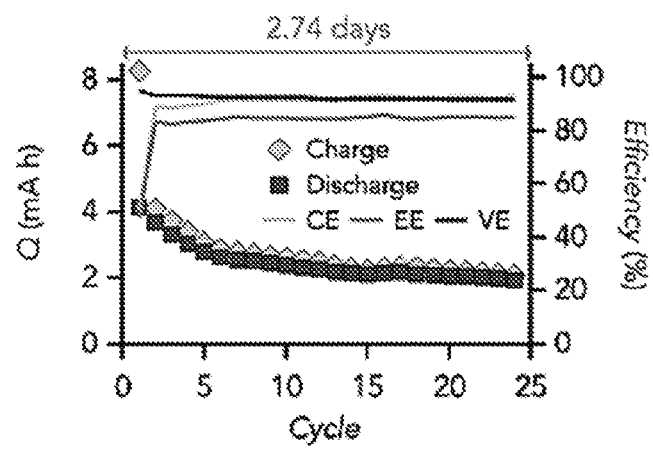
FIG. 21C shows charge and discharge capacity (Q) with corresponding Coulombic efficiency (CE), energy efficiency (EE), and voltage efficiency (VE) for Zn—$K_4Fe(CN)_6$ battery cells configured with Celgard 3501 membranes. Theoretical capacity=8 mA h.
Figure 21D:
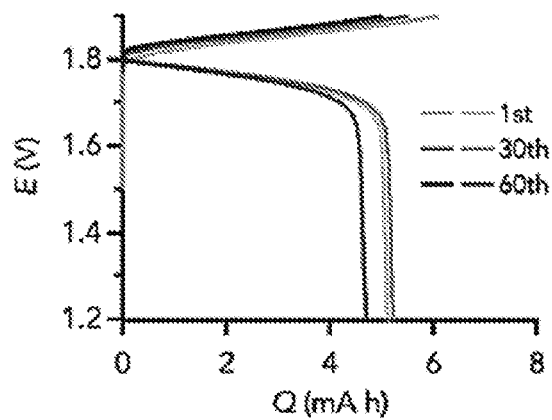
FIG. 21D shows charge and discharge curves of the first, middle, and last cycles for Zn—$K_4Fe(CN)_6$ battery cells configured with AquaPIM 1 membranes.
Figure 21E:
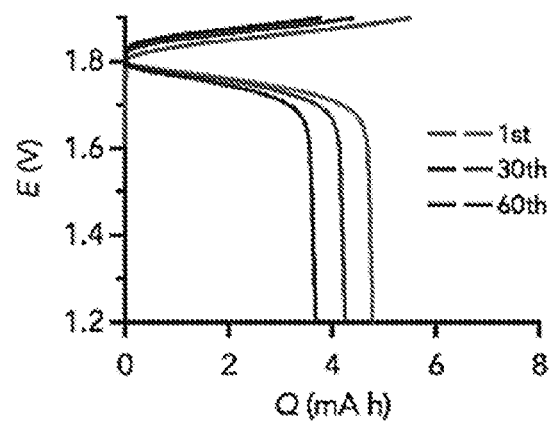
FIG. 21E shows charge and discharge curves of the first, middle, and last cycles for Zn—$K_4Fe(CN)_6$ battery cells configured with Nafion 212 membranes.
Figure 21F:
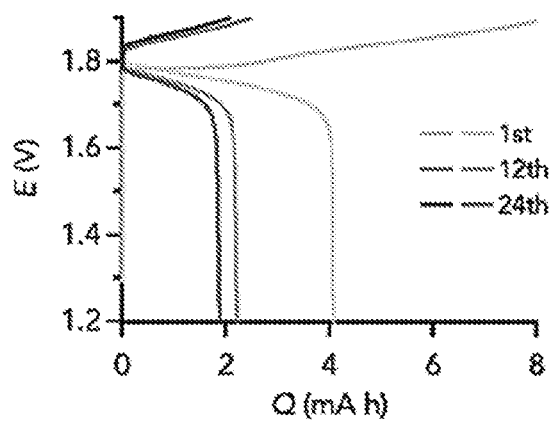
FIG. 21F shows charge and discharge curves of the first, middle, and last cycles for Zn—$K_4Fe(CN)_6$ battery cells configured with Celgard 3501 membranes.
Figure 22A:
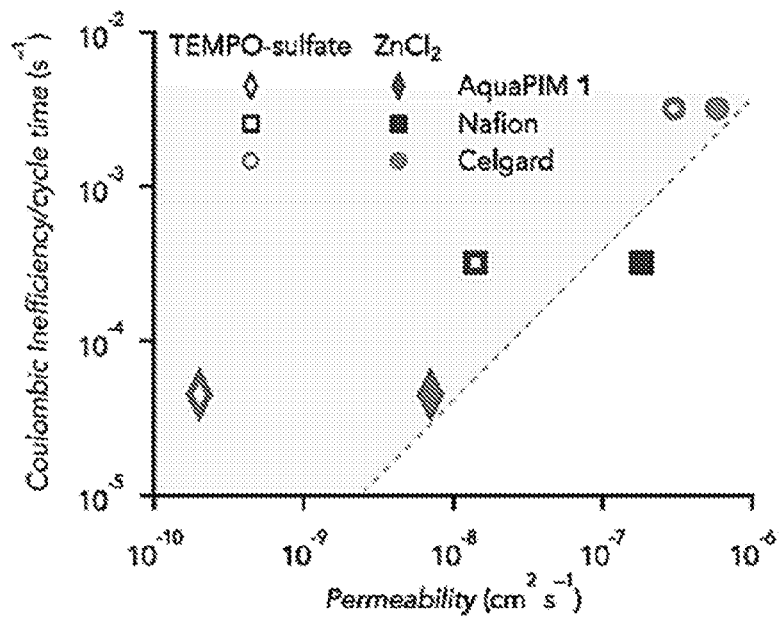
FIG. 22A shows a plot of permeability vs Coulombic inefficiency/time for Zn-TEMPO-sulfate cell chemistry reported in FIG. 20.
Figure 22B:
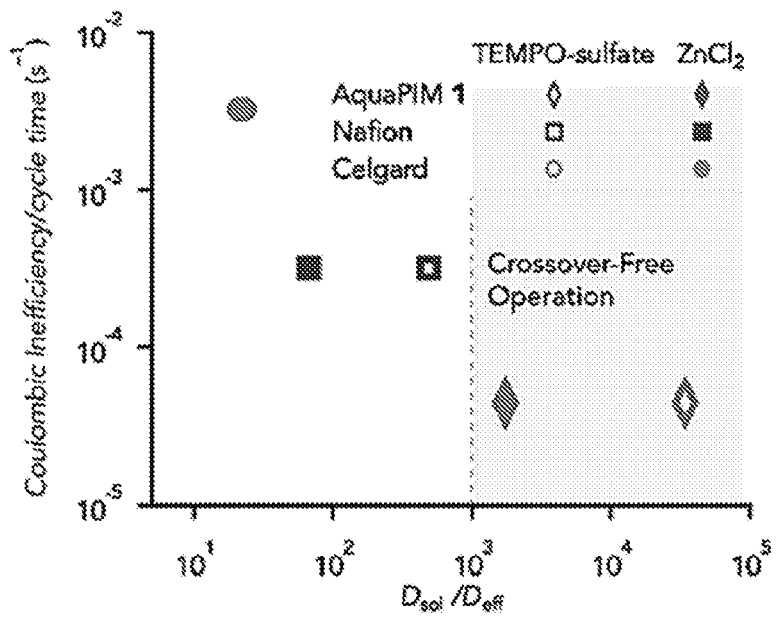
FIG. 22B shows a plot of $D_{sol}/D_{eff}$ vs Coulombic inefficiency/time for Zn-TEMPO-sulfate cell chemistry reported in FIG. 20.
Figure 22C:
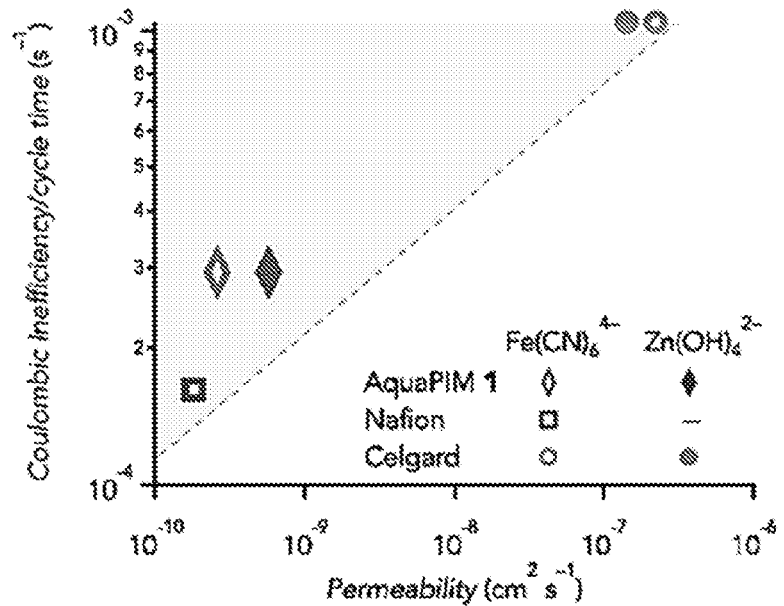
FIG. 22C shows a plot of permeability vs Coulombic inefficiency/time for Zn—$K_4Fe(CN)_6$ cell chemistry reported in FIG. 21.
Figure 22D:
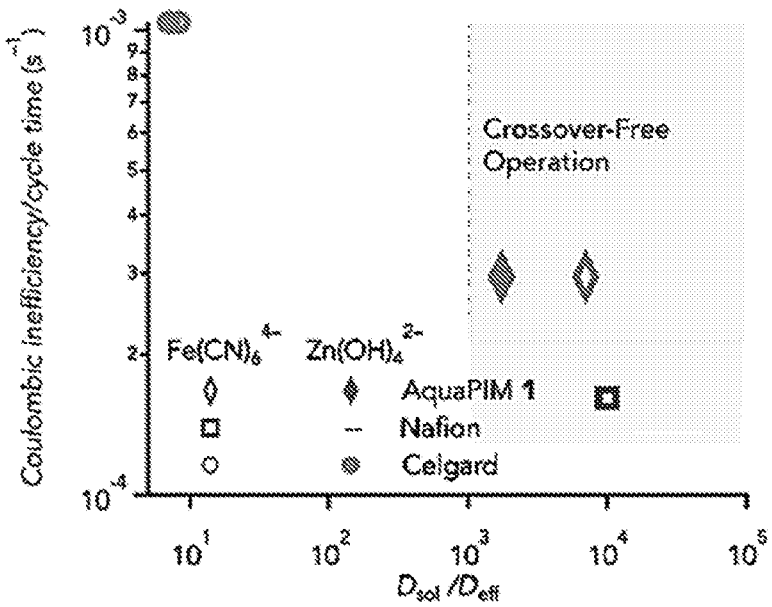
FIG. 22D shows a plot of $D_{sol}/D_{eff}$ vs Coulombic inefficiency/time for Zn—$K_4Fe(CN)_6$ cell chemistry reported in FIG. 21.

Sub-Nanometer Pore Architectures Inherent to AquaPIM Membranes Strictly Enforces Membrane Transport Selectivity. A variety of cell chemistries based on inorganics, metal coordination complexes, organometallics, polyoxometalates, redox-active organic molecules have recently emerged, setting the stage for membrane development given the challenges faced in managing active-material crossover in cells implementing them. As an initial survey of opportunities, three cell chemistries were explored: Zn-TEMPO-sulfate, Zn—K$_4$Fe(CN)$_6$, and Zn—Na$_2$S$_4$. The extrinsic rates of crossover were evaluated for K$_2$Zn(OH)$_4$ (i.e., zincate), ZnCl$_2$, Na$_2$S$_4$ (i.e., polysulfides), K$_4$Fe(CN)$_6$, and sodium TEMPO-4-sulfate (i.e., TEMPO-sulfate) using a diffusion cell equipped with either AquaPIM 1, Nafion 212, or Celgard 3501 membranes. From these data, their intrinsic diffusive permeability in each membrane ($D_{eff}$) were calculated. To compare the blocking properties for each active material, $D_{eff}$ values were normalized to the diffusion coefficient of the actives in electrolyte ($D_{sol}$), which were separately determined by cyclic voltammetry (FIG. 19). Higher values for $D_{sol}/D_{eff}$ indicate better active-material blocking by the membrane in a given electrolyte.

Notably, AquaPIM 1 membranes give $D_{sol}/D_{eff}$ of 1.7×10$^3$ for both zincate and ZnCl$_2$, thereby more effectively managing crossover than either Nafion 212 ($D_{sol}/D_{eff}$=6.7×10$^1$ for ZnCl$_2$) or Celgard 3501 ($D_{sol}/D_{eff}$=7.1×10$^0$ and 2.1×10$^1$ for zincate and ZnCl$_2$, respectively). For the catholytes, differentiating the blocking ability by the membranes was subtler. AquaPIM 1 gave the highest $D_{sol}/D_{eff}$ of all of the active materials explored for TEMPO-sulfate ($D_{sol}/D_{eff}$=3.4×10$^4$), outperforming by orders of magnitude Nafion 212 ($D_{sol}/D_{eff}$=4.9×10$^2$) and Celgard 3501 ($D_{sol}/D_{eff}$=2.3×10$^1$). However, for K$_4$Fe(CN)$_6$, AquaPIM 1 and Nafion 212 were comparable and high—$D_{sol}/D_{eff}$=1.0×10$^4$ and 6.9×10$^3$, respectively—with both outperforming Celgard 3501 ($D_{sol}/D_{eff}$=8.2×10$^0$). Finally, for Na$_2$S$_4$, crossover was only modestly managed by AquaPIM 1 and Nafion 212 under highly alkaline conditions, with both outperforming Celgard 3501: $D_{sol}/D_{eff}$=1.3×10², 6.7×10¹, and 7.8×10⁰, respectively.

AquaPIM Membrane Stability, Conductivity, and Transport Selectivity Dictate Prospects for Crossover-Free Cell Operation. A further aim was to determine how $D_{sol}/D_{eff}$ for a given membrane, electrolyte, and pair of active materials for anolyte and catholyte, in turn, dictate key aspects of aqueous cell performance, including accessible capacity. Coulombic efficiency, and cycle-life. Given the high $D_{sol}/D_{eff}$ for both $ZnCl_2$ and TEMPO-sulfate for AquaPIM 1 in 1.0 M $NH_4Cl$ electrolyte, it was hypothesized that Zn-TEMPO-sulfate cells (~1.70 V) would perform best with the AquaPIM 1 membrane in place. To test this hypothesis, 8 mAh-capacity Zn-TEMPO-sulfate cells were assembled (FIG. 20) consisting of a Zn anode, a 0.50 M $ZnCl_2$ anolyte in 1.0 M $NH_4Cl$, any one of the three membranes under consideration, a 35 mM TEMPO-sulfate catholyte in 1.7 M $NH_4Cl$, and a reticulated vitreous carbon current collector. All cells were cycled at 25° C. at a rate of C/4. Both AquaPIM 1 and Nafion cells accessed ~75% of the theoretical capacity in the first cycle; however, non-selective Celgard 3501 only accessed 44%. Thereafter, the AquaPIM 1 cell maintained 97% of its initial capacity after 50 cycles over ~13 days (0.06% loss per cycle) with Coulombic efficiencies steady at ~99%. On the other hand, for Nafion 212 and Celgard 3501 cells, after the first cycle, rapid capacity fade was noted for both: Nafion 212 retained only 43% of its initial capacity after 34 cycles over 5.7 days (~1.8% loss per cycle) with Coulombic efficiencies steady at ~95%, and Celgard 3501 retained only 46% over 13 cycles over 1.6 days (~3.9% loss per cycle) with Coulombic efficiencies of 50-70%. Either the retention or loss in cell capacity was tied to TEMPO-sulfate crossover. Specifically, analysis of the anolytes after cycling revealed that TEMPO-sulfate did not crossover for cells equipped with AquaPIM 1, while crossover was rampant for Nafion 212 and Celgard 3501.

To make explicit the correlation between active material permeability across the membranes and cell performance, the Coulombic inefficiencies multiplied by the inverse of the cumulative cycle-time of the cells were plotted against either the absolute permeability or $D_{sol}/D_{eff}$ for each active material and membrane (FIG. 22). From these plots, it is evident that high Coulombic inefficiencies and short cycle-lives are strongly and inversely correlated with membrane permeability for $ZnCl_2$ and TEMPO-sulfate, confirming the hypothesis detailed above. It was further concluded that cells for which $D_{sol}/D_{eff}$~10³ for both active materials granted crossover-free operation, yielding longer cycle-life and higher Coulombic efficiency, as evidenced by the superior performance of Zn-TEMPO-sulfate cells with AquaPIM 1 membranes in place.

To further demonstrate that $D_{sol}/D_{eff}$>10³ for a given membrane, electrolyte, and pair of active materials for anolyte and catholyte grants stable, crossover-free aqueous cell performance, the demonstrably high $K_2Zn(OH)_4$ and $K_4Fe(CN)_6$ blocking ability by AquaPIM 1 and Nafion 212 membranes in 40% aqueous KOH (w/w) was studied. However, it should be noted that poor conductivity, owing to reduced phase separation, in part, prevented an accurate determination for $D_{sol}/D_{eff}$ for zincate by Nafion 212 in our hands. Nevertheless, based on their comparable $K_4Fe(CN)_6$ blocking ability, it was hypothesized that Zn—$K_4Fe(CN)_6$ cells (~1.74 V) could perform similarly well for cells configured with either AquaPIM 1 or Nafion 212 membranes, and that each of these should outperform cells configured with non-blocking Celgard 3501 separators. To test these hypotheses, 8 mAh-capacity Zn—$K_4Fe(CN)_6$ cells were assembled (FIG. 21) consisting of a Zn anode, a 175 mM $Na_2Zn(OH)_4$ anolyte in 5.0 M NaOH, any one of the three membranes under consideration, a 35 mM $K_4Fe(CN)_6$ catholyte in 5.0 M NaOH, and a reticulated vitreous carbon current collector. All cells were cycled at 25° C. at a rate of C/4. The AquaPIM 1 cell attained the highest initial capacity, 65% of theoretical, and maintained 95% of this initial capacity over 60 cycles spanning 13 days (0.13% loss per cycle) with a Coulombic efficiency ~95% throughout cycling. The Nafion 212 performed nearly, but not quite, as well, reaching 60% of its theoretical capacity initially, and over 60 cycles spanning 8.75 days, maintaining 80% of that initial capacity (0.38% loss per cycle) with a Coulombic efficiency of ~98%. In contrast, as expected given the $D_{sol}/D_{eff}$<10³ for both active materials, the cell configured with Celgard 3501 showed 2.2% capacity fade per cycle, with only 47% capacity retention over 24 cycles. Furthermore, only 52% of the theoretical capacity was accessed in the first cycle, and the Coulombic efficiency was consistently lower (~90%). As was noted previously, plotting the quotient of the Coulombic inefficiency and cumulative cycle-time for each cell against either the absolute permeability or $D_{sol}/D_{eff}$ for each active material and a given membrane (FIG. 21), cell performance was concluded to track active-material permeability, inversely, and $D_{sol}/D_{eff}$>10³ allowed for stable cycling outcome for both active materials.

In each of the examples above, the chosen cell chemistries afforded $D_{sol}/D_{eff}$>10³ for both active materials in the cell for at least one of the membranes, most consistently for AquaPIM 1. However, a cell chemistry for which only one of the actives falls above the 10³ threshold for $D_{sol}/D_{eff}$ had not yet been considered. To resolve this outstanding question, an 8 mAh-capacity Zn—$Na_2S_4$ cell was assembled with a Zn anode, an anolyte consisting of 70 mM $Na_2Zn(OH)_4$ in 1.0 M NaOH, an AquaPIM 1 membrane, a catholyte consisting of 5.8 mM $Na_2S_4$ in 1.0 M NaOH, and a reticulated vitreous carbon current collector. In such a cell, the AquaPIM 1 membrane can be expected based on the results above to block zincate crossover effectively ($D_{sol}/D_{eff}$=1.7×10³), but permit to an extent polysulfide crossover ($D_{sol}/D_{eff}$=1.3×10²). The crossover of polysulfides in such cells could lead to the formation of zinc sulfide either in the anolyte, or on the Zn electrode, if left unchecked. Complete passivation of the Zn electrode by ionically insulating ZnS would render it inoperable, which would prevent the cell from functioning. Indeed, after cell assembly, only 1% of the 8 mAh theoretical capacity was accessed in the initial cycle, fading to 0.6% of the theoretical capacity after 100 cycles. Cyclic voltammetry of the catholyte revealed a shift in cathodic peak to higher potential, indicative of smaller polysulfides crossing over to the anode. Concomitantly, the formation of a precipitate on the zinc metal anode was observed, which was concluded to be ZnS after analysis by XRD. The poor performance of the Zn—$Na_2S_4$ cell supports the conclusion that $D_{sol}/D_{eff}$ should be greater than 10³ for both active materials in the cell for a given cell chemistry, electrolyte, and choice of membrane to afford stable, crossover-free operation.

In the foregoing specification, the invention has been described with reference to specific embodiments. However, one of ordinary skill in the art will appreciate that various modifications and changes can be made without departing from the scope of the invention as set forth in the claims. Accordingly, the specification and figures are to be regarded in an illustrative sense rather than a restrictive sense, and all such modifications are intended to be included within the scope of invention. In addition, each reference provided herein is incorporated by reference in its entirety to the same extent as if each reference was individually incorporated by reference.

What is claimed is:
1. A microporous polymer according to the formula:
   -[A-AB-B]$_n$—,
   or a salt thereof,
   wherein:
   n is an integer ranging from 10 to 10,000;
   each monomer segment A-A is independently a monomer segment according to Formula (A), (B), (C), (D), (E), (F), (G) or (H):
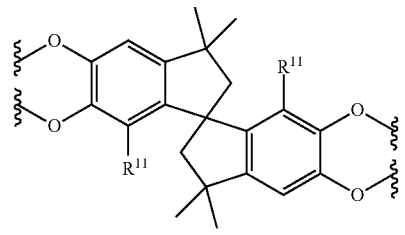
(A)
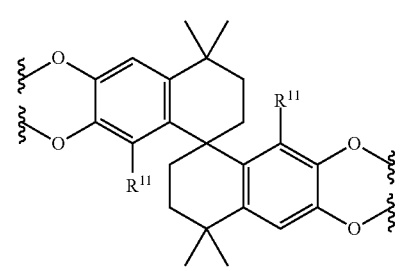
(B)
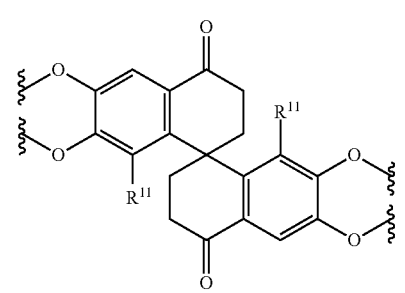
(C)
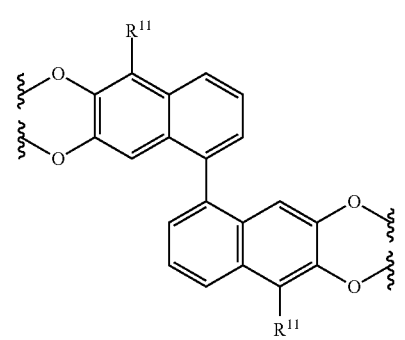
(D)
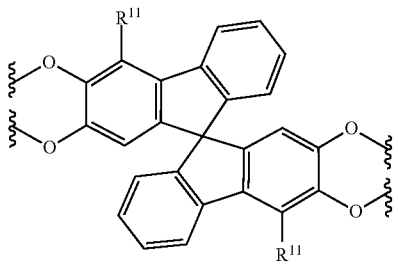
(E)
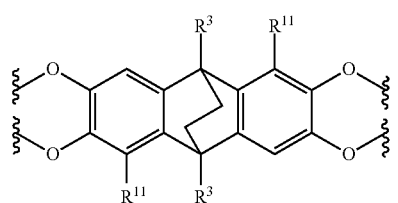
(F)
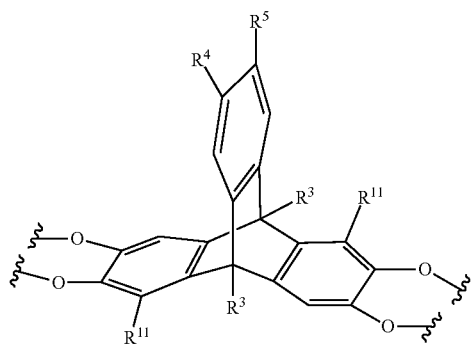
(G)
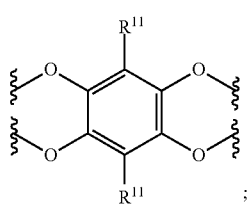
(H)
;
each monomer segment B-B is independently a monomer segment according to Formula (a), (b), (c), (d), (e), or (f):
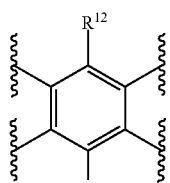
(a)
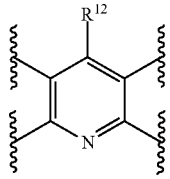
(b)

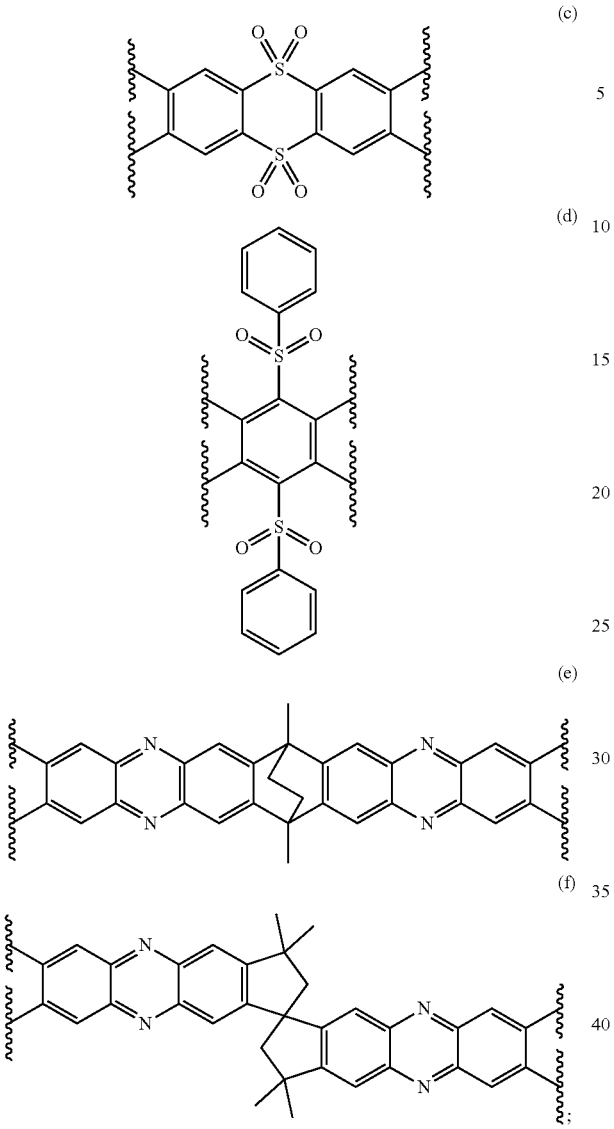

each R¹¹ is independently selected from the group consisting of —CH₂NR¹R² and H;
each R¹² is independently selected from the group consisting of —C(NOR¹³)N(R¹⁴)₂ and —CN;
at least one R¹¹ in at least one monomer segment A-A is —CH₂NR¹R², or at least one R¹² in at least one monomer segment B-B is —C(NOR¹³)N(R¹⁴)₂;
each R¹ and R² is independently selected from the group consisting of (C₁₋₂₀)alkyl, (C₂₋₂₀)alkenyl, (C₂₋₂₀)alkynyl, (C₆₋₁₂)aryl, (C₃₋₈)cycloalkyl, (C₆₋₁₂)aryl(C₁₋₂₀)alkyl, (C₃₋₈)cycloalkyl(C₁₋₂₀)alkyl, hetero(C₁₋₂₀)alkyl, 3- to 8-membered heterocyclyl, 3- to 8-membered heterocyclyl-(C₁₋₂₀)alkyl, 5- to 8-membered heteroaryl, heteroaryl(C₁₋₂₀)alkyl,
wherein each R¹ and R² is optionally and independently substituted with one or more Z¹,
wherein each (C₁₋₂₀)alkyl, (C₂₋₂₀)alkenyl, and (C₂₋₂₀) alkynyl in R¹ and R² optionally and independently comprises one or more heteroatoms independently selected from silicon, a chalcogenide, and a pnictide, and wherein one or more atoms in R¹ and R² are optionally and independently present in oxidized form as C=O, C=S, N=O, N=S, S=O or S(O)₂; or
alternatively, each R¹ is optionally and independently taken together with R², and the nitrogen atom to which both are attached, to form 3- to 8-membered heterocyclyl or 5- to 8-membered heteroaryl, each of which is optionally substituted with one or more Z²;
each Z¹ and Z² is independently selected from the group consisting of halogen, —OH, —NO₂, —CN, (C₁₋₂₀) alkyl, (C₂₋₂₀)alkenyl, (C₂₋₂₀)alkynyl, (C₆₋₁₂)aryl, (C₃₋₈) cycloalkyl, (C₆₋₁₂)aryl(C₁₋₂₀)alkyl, hetero(C₁₋₂₀)alkyl, 3- to 8-membered heterocyclyl, 5- to 8-membered heteroaryl, (C₃₋₈)cycloalkyl-(C₁₋₂₀)alkyl, 3- to 8-membered heterocyclyl-(C₁₋₂₀)alkyl, 5- to 8-membered heteroaryl-(C₁₋₂₀)alkyl, halo(C₁₋₂₀)alkyl, halo(C₁₋₂₀)alkyloxy, —OR⁶, —SR⁶, —S(O)R⁶, —S(O)₂R⁶, —SO₂NR⁶R⁷, —NR⁶C(O)R⁷, —NR⁶S(O)₂R⁷, —NR⁶C(O)NR⁷R⁸, —NR⁶R⁷, —CO₂R⁶, —C(O)NR⁶R⁷, and —C(O)R⁶;
each R³, R⁴, R⁵, R⁶, R⁷, and R⁸ is independently selected from the group consisting of (C₁₋₂₀)alkyl, (C₂₋₂₀)alkenyl, (C₂₋₂₀)alkynyl, (C₆₋₁₂)aryl, (C₃₋₈)cycloalkyl, (C₆₋₁₂)aryl(C₁₋₂₀)alkyl, (C₃₋₈)cycloalkyl(C₁₋₂₀)alkyl, hetero(C₁₋₂₀)alkyl, 3- to 8-membered heterocyclyl, 3- to 8-membered heterocyclyl-(C₁₋₂₀)alkyl, 5- to 8-membered heteroaryl, 5- to 8-membered heteroaryl-(C₁₋₂₀) alkyl; or
alternatively, R⁴ and R⁵ are taken together to form (C₄₋₈) cycloalkyl, (C₆₋₁₂)aryl, 4- to 8-membered heterocyclyl, or 5- to 8-membered heteroaryl; or
alternatively, R⁶ and R⁷ are taken together to form 4- to 8-membered heterocyclyl or 5- to 8-membered heteroaryl; or
alternatively, R⁷ and R⁸ are taken together to form 4- to 8-membered heterocyclyl or 5- to 8-membered heteroaryl;
each R¹³ is selected from the group consisting of H, (C₁₋₂₀)alkyl, and (C₃₋₈)cycloalkyl, wherein (C₁₋₂₀)alkyl and (C₃₋₈)cycloalkyl are optionally and independently substituted with one or more Z³,
provided that R¹³ is (C₁₋₂₀)alkyl or (C₃₋₈)cycloalkyl, each of which is optionally and independently substituted with one or more Z³, when all R¹¹ groups in monomer segments according to Formula (A) are H;
each R¹⁴ is independently selected from the group consisting of H, (C₁₋₂₀)alkyl, and (C₃₋₈)cycloalkyl; and
each Z³ is independently selected from the group consisting of halogen, —NO₂, —CN, —OH, —SO₃H, —NH₂, (C₁₋₂₀)alkyl, (C₂₋₂₀)alkenyl, (C₂₋₂₀)alkynyl, (C₆₋₁₂)aryl, (C₃₋₈) cycloalkyl, (C₆₋₁₂)aryl(C₁₋₂₀)alkyl, hetero(C₁₋₂₀)alkyl, 3- to 8-membered heterocyclyl, 5- to 8-membered heteroaryl, (C₃₋₈)cycloalkyl-(C₁₋₂₀)alkyl, 3- to 8-membered heterocyclyl-(C₁₋₂₀)alkyl, 5- to 8-membered heteroaryl-(C₁₋₂₀)alkyl, halo(C₁₋₂₀)alkyl, halo(C₁₋₂₀)alkyloxy, —OR⁶, —SR⁶, —S(O)R⁶, —S(O)₂R⁶, —SO₂NR⁶R⁷, —NR⁶C(O)R⁷, —NR⁶S(O)₂R⁷, —NR⁶C(O)NR⁷R⁸, —NR⁶R⁷, —CO₂R⁶, —C(O)NR⁶R⁷, and —C(O)R⁶.

2. The microporous polymer of claim 1, or the salt thereof, wherein:
each monomer segment A-A is independently a monomer segment according to Formula (A-i), (B-i), (C-i), (D-i), (E-i), (F-i), (G-i) or (H-i):

(A-i)
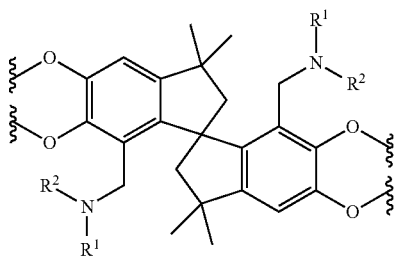
(B-i)
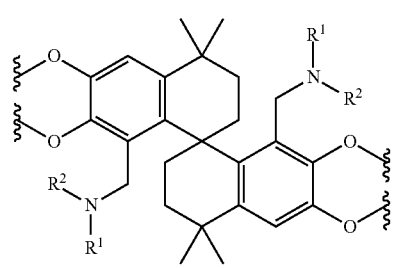
(C-i)
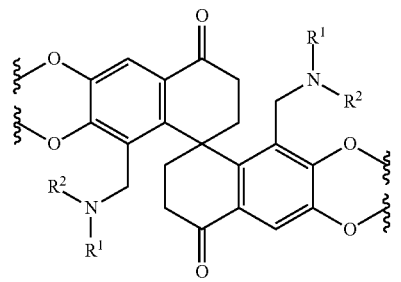
(D-i)
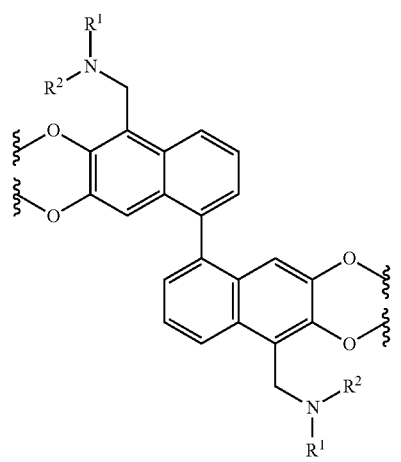
(E-i)
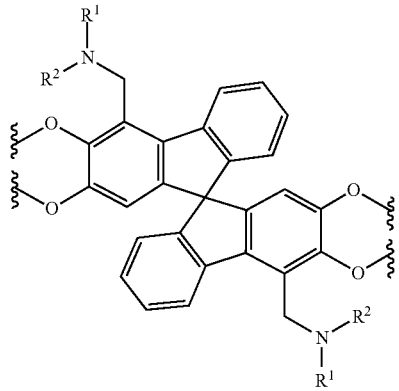
(F-i)
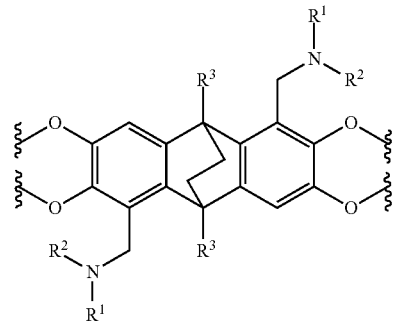
(G-i)
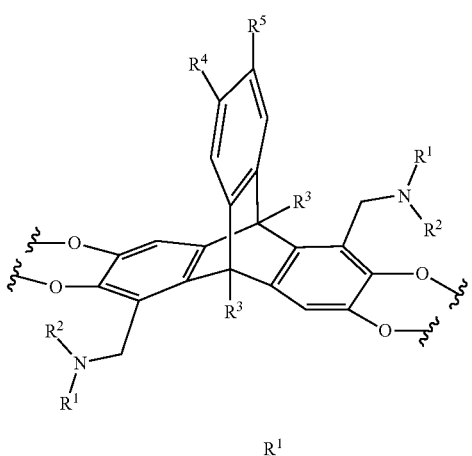
(H-i)
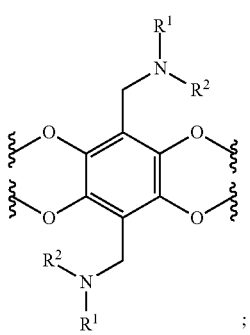
and each monomer segment B-B is independently a monomer segment according to Formula (a-i), (b-i), (c), (d), (e), or (f):

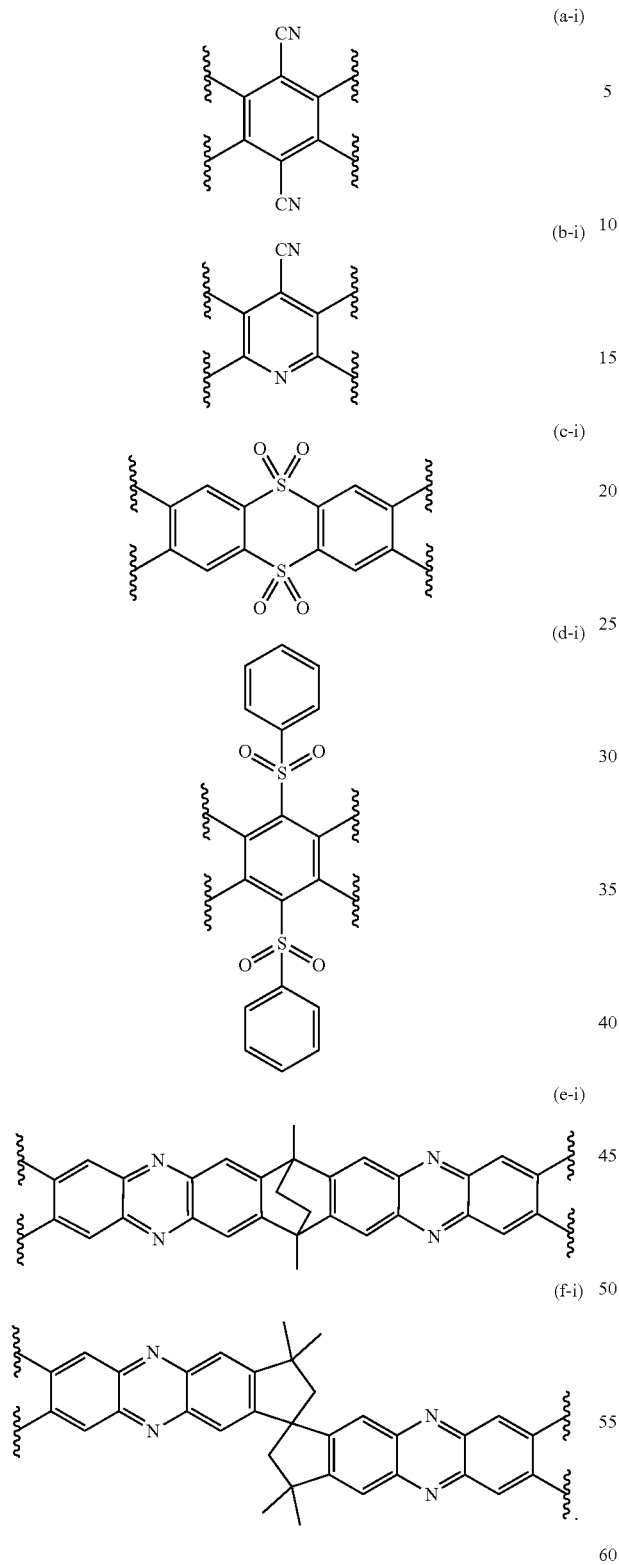
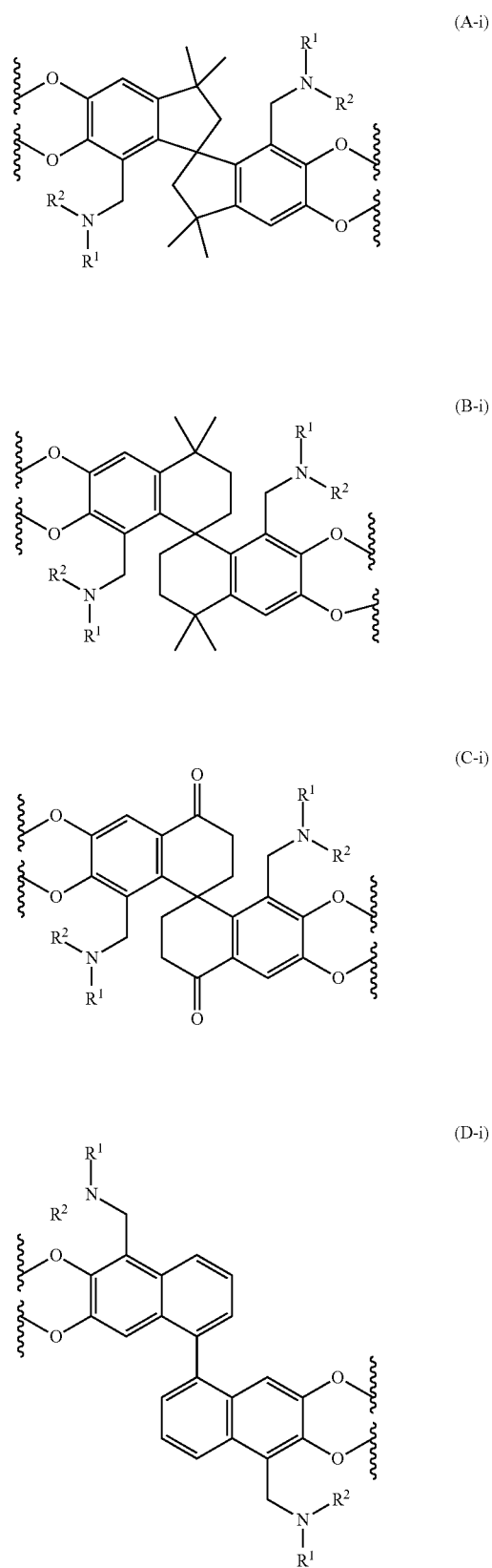
3. The microporous polymer of claim 1, or the salt thereof, wherein:
each monomer segment A-A is independently a monomer segment according to Formula (A-i), (B-i), (C-i), (D-i), (E-i), (F-i), (G-i), (H-i), (B-ii), (C-ii), (C-ii), (E-ii), (F-ii), (G-ii), or (H-ii):

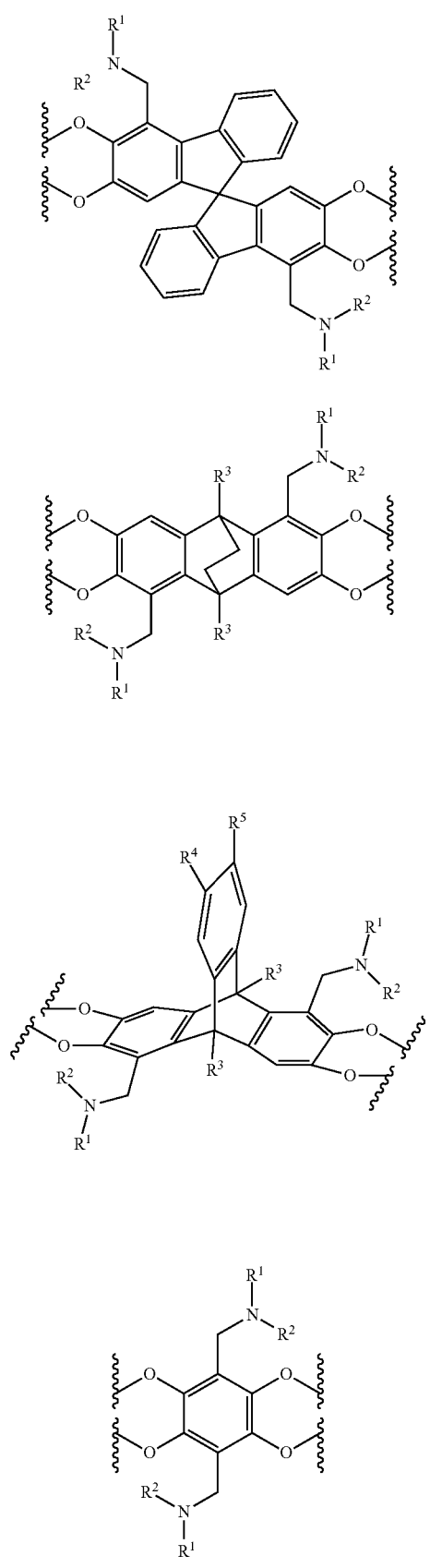
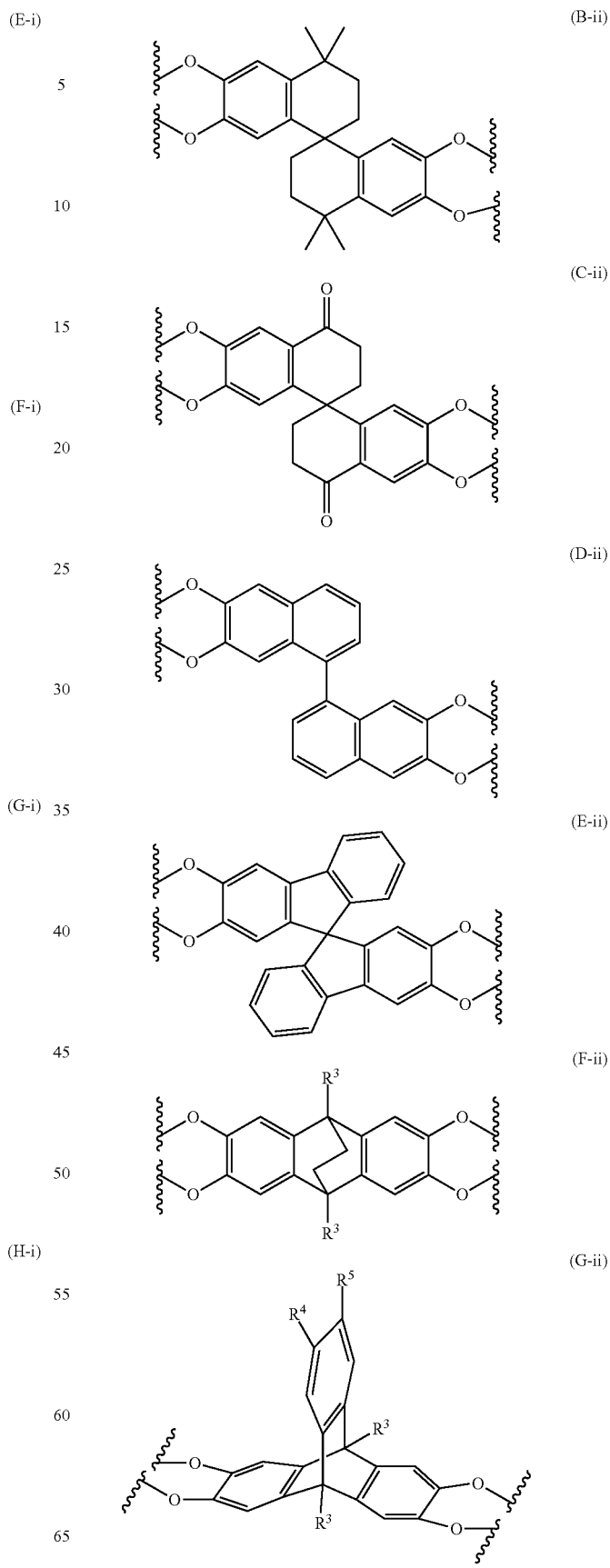

(H-ii)
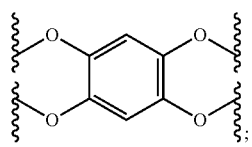
and each monomer segment B-B is independently a monomer segment according to Formula (a-ii) or (b-ii):
(a-ii)
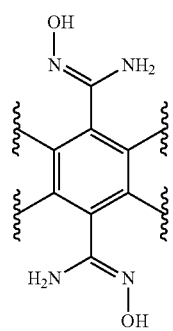
(b-ii)
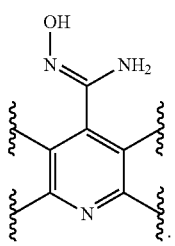
4. The microporous polymer of claim 1, or the salt thereof, wherein:
each monomer segment A-A is independently a monomer segment according to Formula (A-i), (B-i), (C-i), (D-i), (E-i), (F-i), (G-i), (H-i), (B-ii), (C-ii), (D-ii), (E-ii), (F-ii), (G-ii), (H-ii), or (A-ii):
(A-i)
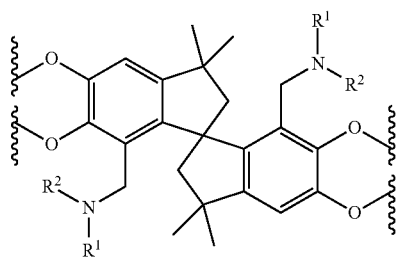
(B-i)
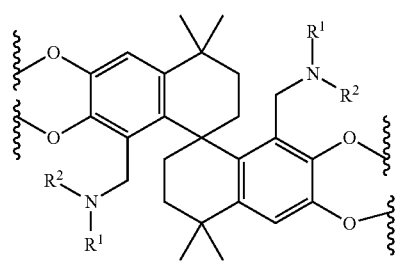
(C-i)
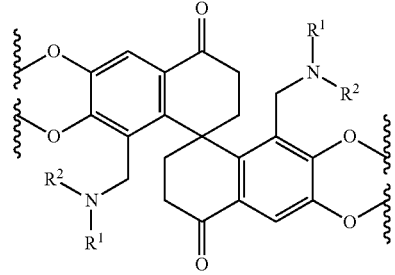
(D-i)
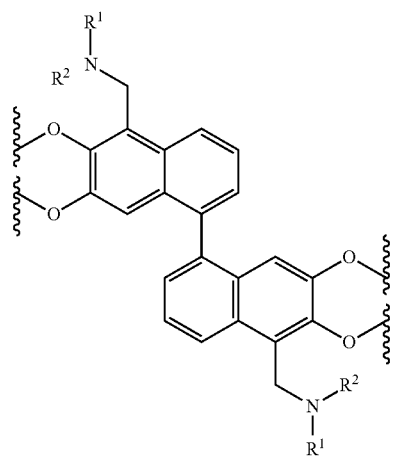
(E-i)
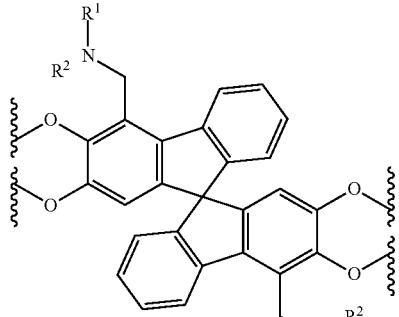
(F-i)
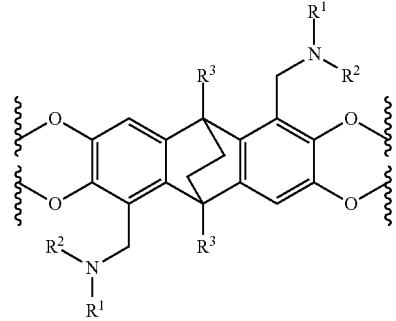

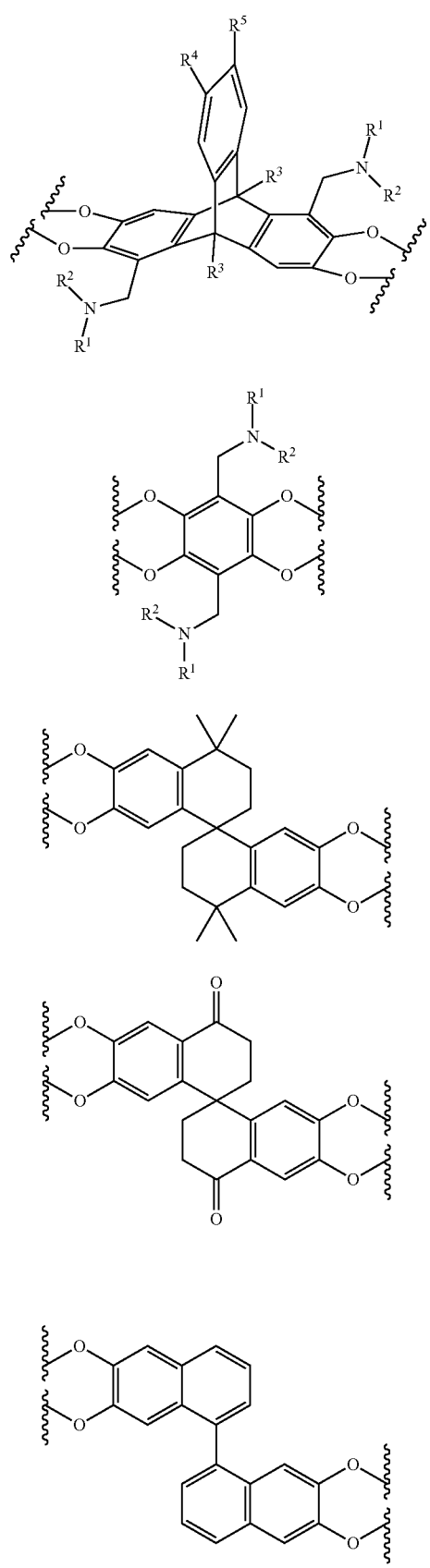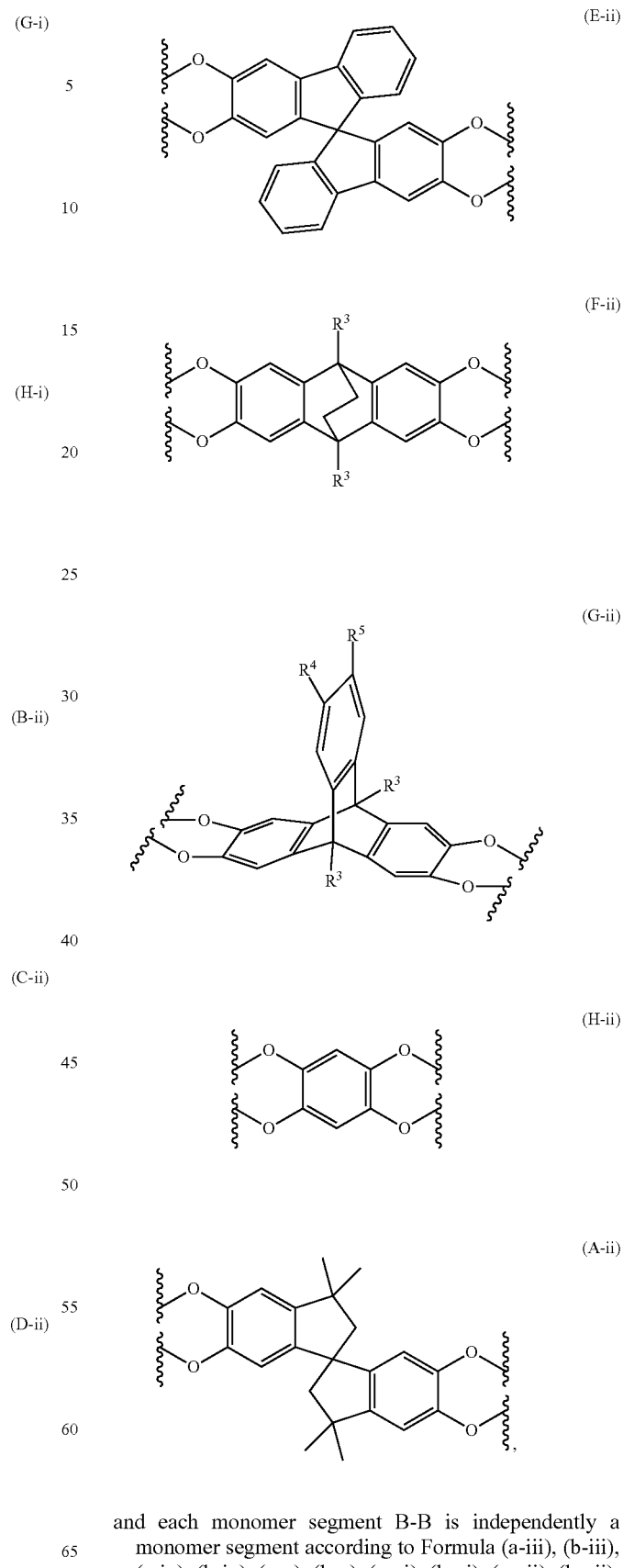
and each monomer segment B-B is independently a monomer segment according to Formula (a-iii), (b-iii), (a-iv), (b-iv), (a-v), (b-v), (a-vi), (b-vi), (a-vii), (b-vii), (a-viii), or (b-viii):

(a-iii)
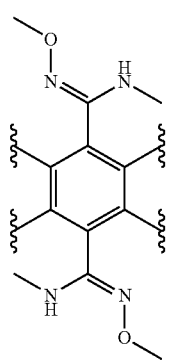
(b-iii)
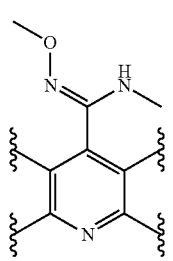
(a-iv)
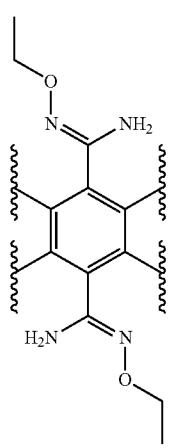
(b-iv)
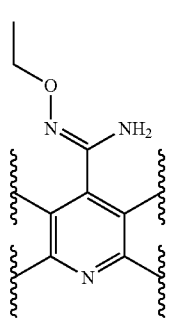
(a-v)
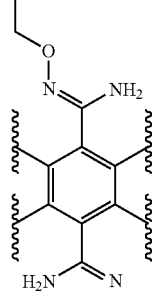
(b-v)
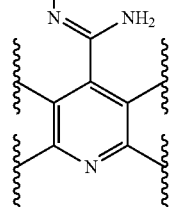

-continued (a-vi)

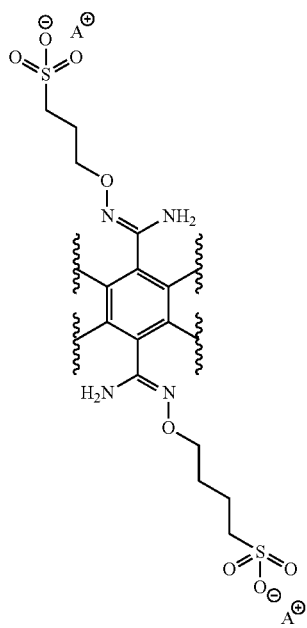

(b-vi)

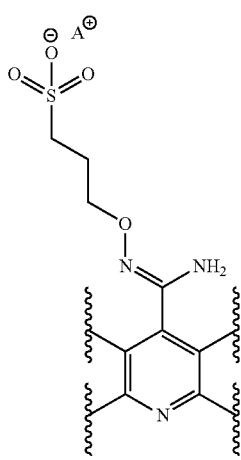

(a-vii)

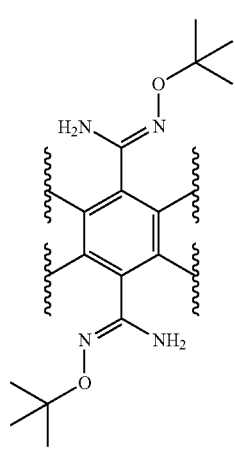

-continued (b-vii)

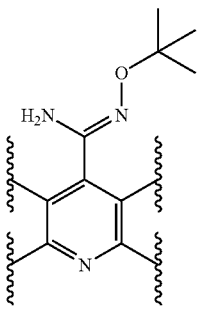

(a-viii)

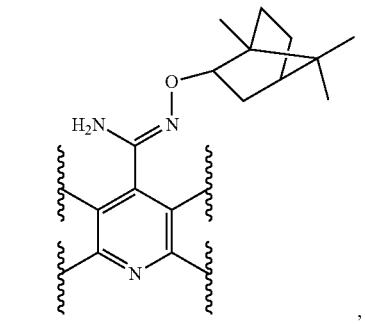

(b-viii)

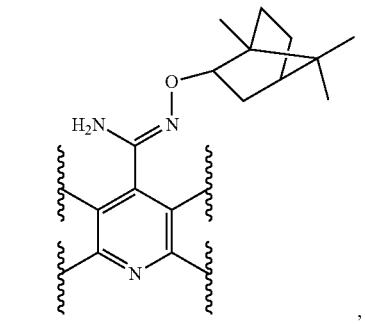

, wherein $A^+$ is an inorganic cation or an organic cation.

5. The microporous polymer of claim 4, or the salt thereof, wherein each monomer segment B-B is independently a monomer segment according to Formula (a-iii), (b-iii), (a-iv), (b-iv), (a-v), (b-v), (a-vi), or (b-vi).

6. The microporous polymer of claim 4, or the salt thereof, wherein each monomer segment B-B is independently a monomer segment according to Formula (a-vii), (b-vii), (a-viii), or (b-viii).

7. The microporous polymer of claim 1, or the salt thereof, wherein the microporous polymer has a surface area ranging from about 5 m² g⁻¹ to about 1000 m² g⁻¹.

8. The microporous polymer of claim 1, or the salt thereof, wherein the microporous polymer has pore sizes ranging from about 0.4 nm to about 5 nm.

9. The microporous polymer of claim 1, or the salt thereof, wherein the microporous polymer has a porosity ranging from about 5% to about 40%.

10. A method for preparing a microporous polymer according to claim 1, the method comprising
forming a polymerization mixture comprising
(1) a plurality of A-A monomers, wherein each A-A monomer is independently a compound according to Formula (I), (II), (III), (IV), (V), (VI), (VII), or (VIII)
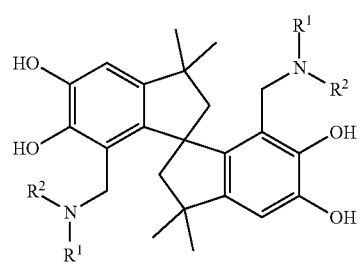
(I)
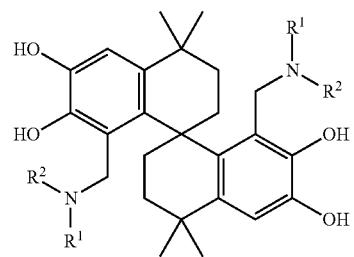
(II)
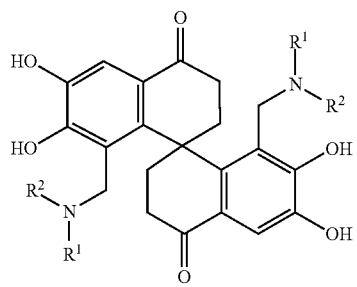
(III)
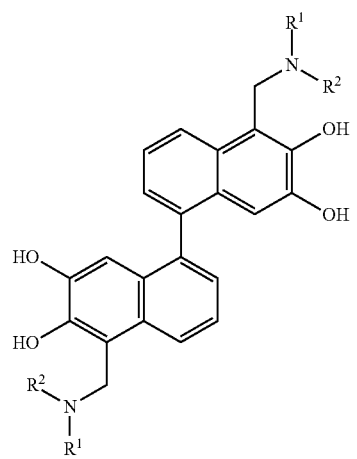
(IV)
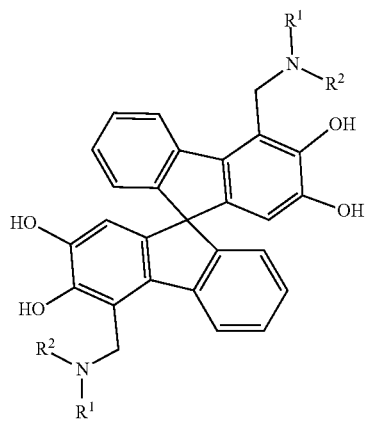
(V)
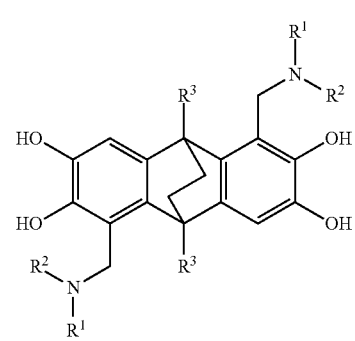
(VI)
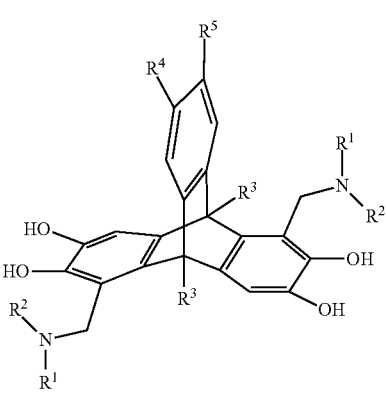
(VII)
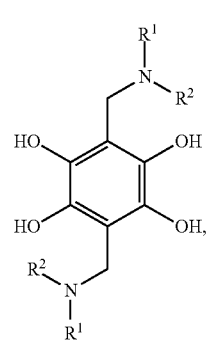
(VIII)
or Formula (Ia), (IIa), (IIIa), (IVa), (Va), (VIa), (VIIa), or (VIIIa)

(Ia)
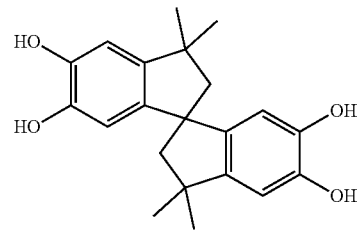
(IIa)
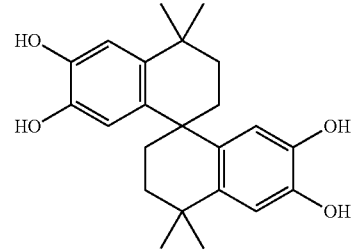
(IIIa)
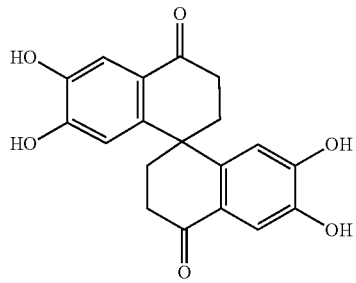
(IVa)
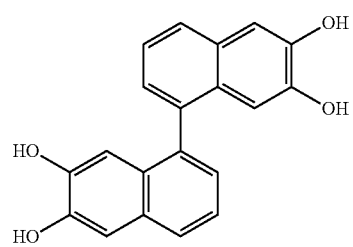
(Va)
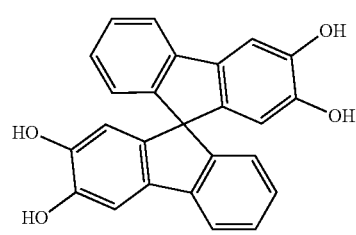
(VIa)
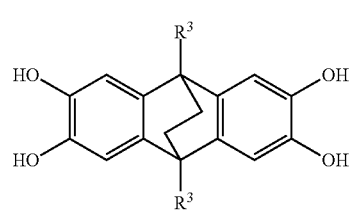
(VIIa)
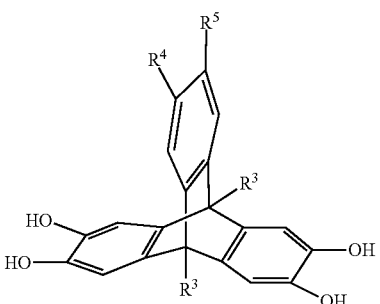
(VIIIa)
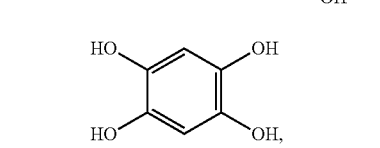
(2) a plurality of B-B monomers, wherein each B-B monomer is independently a compound according to Formula (i), (ii), (iii), (iv), (v), or (vi):
(i)
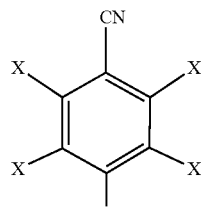
(ii)
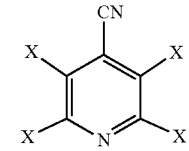
(iii)
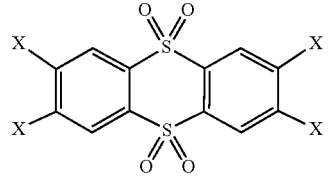
(iv)
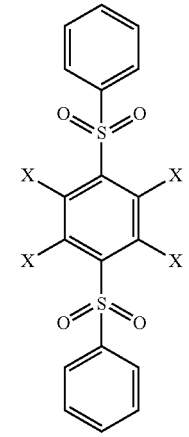

-continued

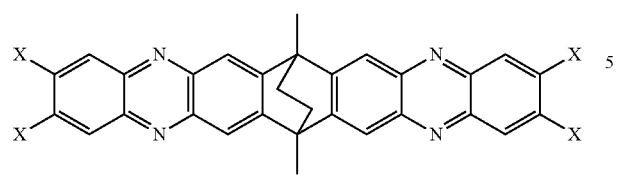
(v)

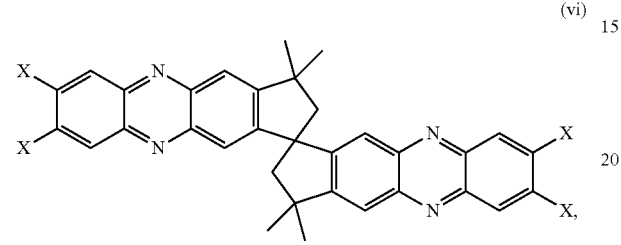
(vi)

wherein X is a halide, and (3) a base, and heating the polymerization mixture, thereby forming the microporous polymer.

11. The method of claim 10, wherein the polymerization mixture further comprises solid grinding media, liquid grinding media, or a combination thereof.

12. The method of claim 10, wherein at least one monomer segment B-B in the microporous polymer is a monomer segment according to Formula (a-i) or Formula (b-i):

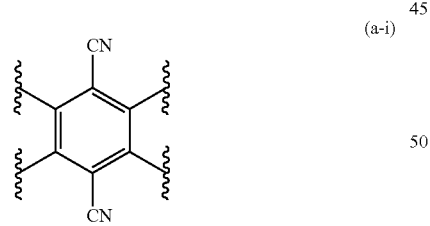
(a-i)

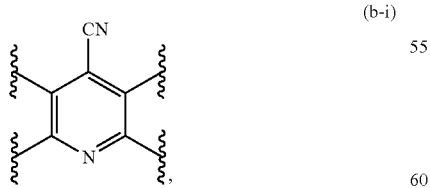
(b-i)

and the method further comprises combining the microporous polymer with hydroxyl amine under conditions sufficient to form a modified microporous copolymer having at least one monomer segment B-B according to Formula (a-ii) or Formula (b-ii):

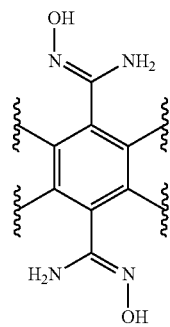
(a-ii)

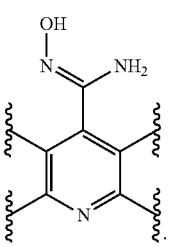
(b-ii)

13. The method of claim 12, further comprising:

combining the modified microporous copolymer with a base and an alkylating agent under conditions sufficient to form an alkylated microporous polymer having at least one monomer segment B-B according to Formula (a-iii), (b-iii), (a-iv), (b-iv), (a-v), (b-v), (a-vi), or (b-vi):

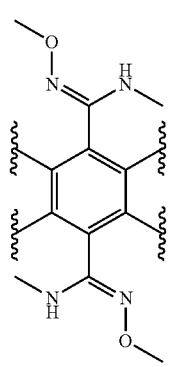
(a-iii)

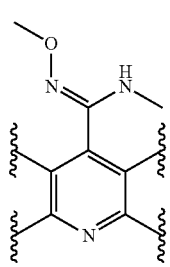
(b-iii)

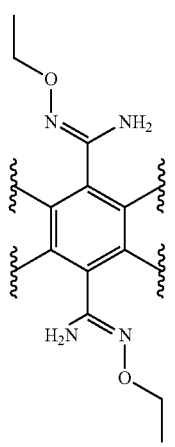
(a-iv)
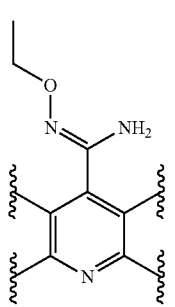
(b-iv)
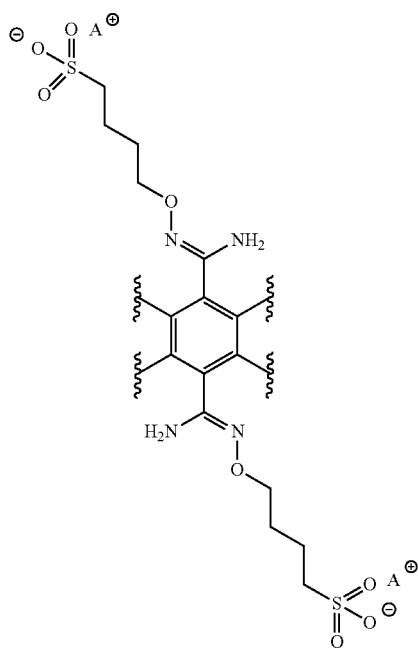
(a-v)
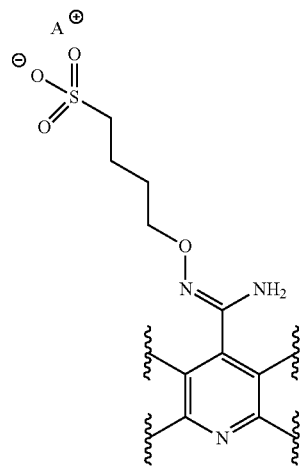
(b-v)
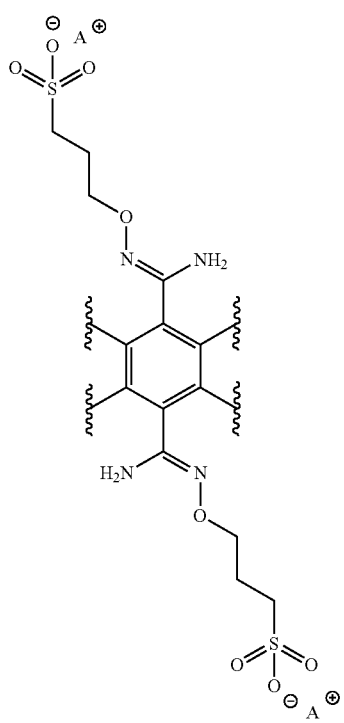
(a-vi)
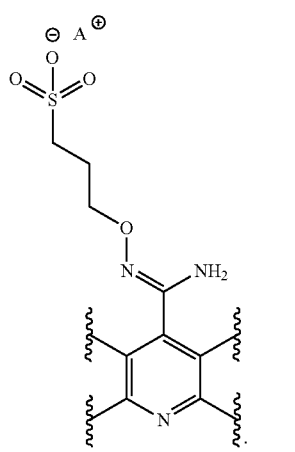
(b-vi)

14. The method of claim 13, wherein the alkylating agent is selected from the group consisting of dimethyl sulfate, diethyl sulfate, propane sultone, and butane sultone.

15. The method of claim 13, wherein:
the alkylated microporous polymer comprises at least one monomer segment B-B according to Formula (a-v), (b-v), (a-vi), or (b-vi); and
the method further comprises combining the alkylated microporous polymer with a salt A⁺X⁻ under conditions sufficient to form a cation-exchanged microporous polymer, wherein the cation $A^+$ is a metal cation or an organic cation, and the anion $X^-$ is an organic anion or an inorganic anion.

16. The method of claim 12, further comprising combining the modified microporous copolymer with an acid and carbocation-generating compound to form an alkylated microporous polymer having at least one B-B segment according to Formula (a-vii), (b-vii), (a-viii), or (b-viii):

(a-vii)
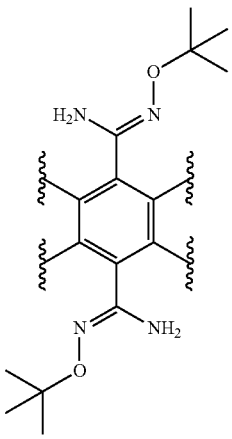

(b-vii)
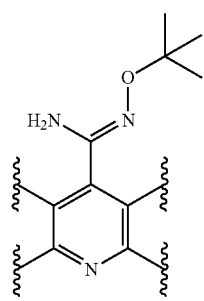

(a-viii)
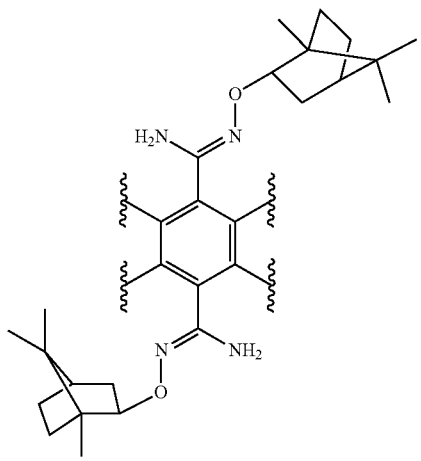

(b-viii)
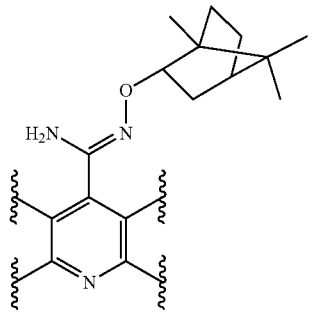

17. An electrochemical cell comprising:
an anode;
an anode electrolyte in contact with h anode;
a separator in contact with the anode electrolyte, wherein said separator comprises a membrane comprising one or more microporous polymers according to claim 1, or salts thereof, wherein said membrane has a thickness ranging from 0.1-1000 micrometers;
a cathode;
a cathode electrolyte in contact with the separator; and
a cathode electrolyte in contact with the cathode.

18. The electrochemical cell of claim 17, wherein at least one repeat unit of the membrane is crosslinked with a non-adjacent repeat unit by a crosslinker.

19. The electrochemical cell of claim 18, wherein the crosslinker is selected from the group consisting of 2,6-bis (4-azidobenzylidene)cyclohexanone, oxygen, 2,6-bis(4-azidobenzylidene)-4-methylcyclohexanone, 2,6-bis(4-azidobenzylidene)-4-ethylcyclohexanone, 4-azidophenylsulfone, and combinations thereof.

20. The electrochemical cell of claim 17, wherein the membrane is in contact with a support comprising a poly (arylether), a poly(arylether) copolymer, a poly(arylether sulfone) copolymer, polyethylene, a polyethylene copolymer, polypropylene, a polypropylene copolymer, polyacrylonitrile, a polyacrylonitrile copolymer, poly(vinylidene fluoride), poly(tetrafluoroethylene), poly(vinyl chloride), a poly(vinylchloride) copolymer, poly(hexafluoropropylene), a poly(hexafluoropropylene) copolymer, a polyaramide, a polyaramide copolymer, a porous metal, a porous alloyed metal, a porous metal oxide, or a combination thereof.

21. The microporous polymer of claim 1, wherein
each $R^{11}$ is independently selected from the group consisting of —CH$_2$NR$^1$R$^2$;

each $R^{12}$ is —CN;

each $R^1$ and $R^2$ is independently $(C_{1-20})$alkyl; or alternatively, each $R^1$ is optionally and independently taken together with $R^2$, and the nitrogen atom to which both are attached, to form 3- to 8-membered heterocyclyl, each of which is optionally substituted with one or more $Z^2$;

each $Z^2$ is independently selected from the group consisting of halogen, —OH, —NO$_2$, —CN, $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, hetero$(C_{1-20})$alkyl, 3- to 8-membered heterocyclyl, 5- to 8-membered heteroaryl, $(C_{3-8})$cycloalkyl-$(C_{1-20})$alkyl, 3- to 8-membered heterocyclyl-$(C_{1-20})$alkyl, 5- to 8-membered heteroaryl-$(C_{1-20})$alkyl, halo$(C_{1-20})$alkyl, halo$(C_{1-20})$alkyloxy, —OR$^6$, —SR$^6$, —S(O)R$^6$, —S(O)$_2$R$^6$, —SO$_2$NR$^6$R$^7$, —NR$^6$C(O)R$^7$, —NRS(O)$_2$R$^7$, —NR$^6$C(O)NR$^7$R$^8$, —NR$^6$R$^7$, —CO$_2$R$^6$, —C(O)NR$^6$R$^7$, and —C(O)R$^6$; and each $R^6$, $R^7$, and $R^8$ is independently selected from the group consisting of $(C_{1-20})$alkyl, $(C_{2-20})$alkenyl, $(C_{2-20})$alkynyl, $(C_{6-12})$aryl, $(C_{3-8})$cycloalkyl, $(C_{6-12})$aryl$(C_{1-20})$alkyl, $(C_{3-8})$cycloalkyl$(C_{1-20})$alkyl, hetero$(C_{1-20})$alkyl, 3- to 8-membered heterocyclyl, 3- to 8-membered heterocyclyl-$(C_{1-20})$alkyl, 5- to 8-membered heteroaryl, 5- to 8-membered heteroaryl-$(C_{1-20})$alkyl; or alternatively, $R^6$ and $R^7$ are taken together to form 4- to 8-membered heterocyclyl or 5- to 8-membered heteroaryl; or alternatively, $R^7$ and $R^8$ are taken together to form 4- to 8-membered heterocyclyl or 5- to 8-membered heteroaryl.

22. The microporous polymer of claim 1, having the structure of:

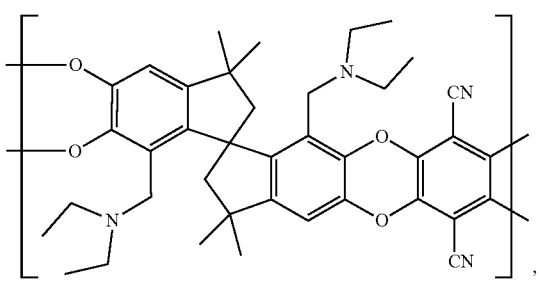

,

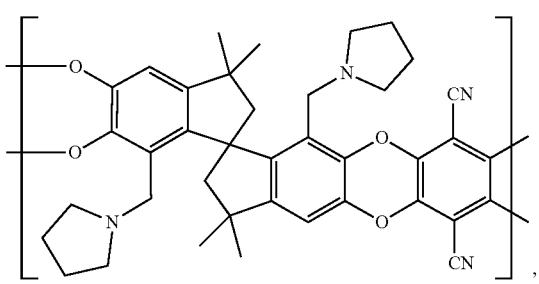

,

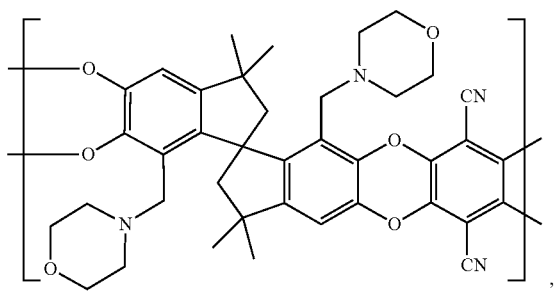

,

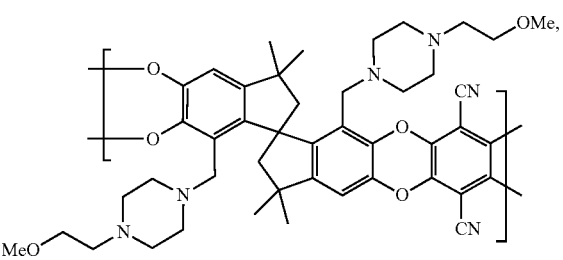

,

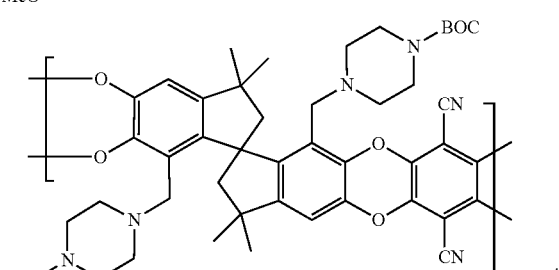

, and

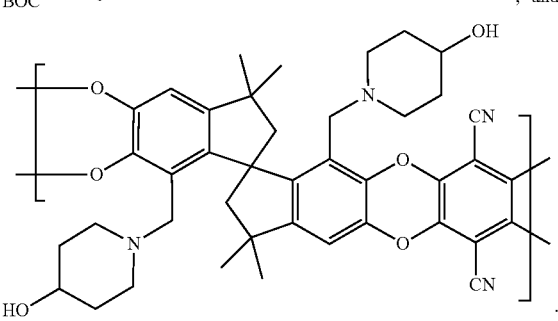

.

23. The microporous polymer of claim 1, having the structure of:

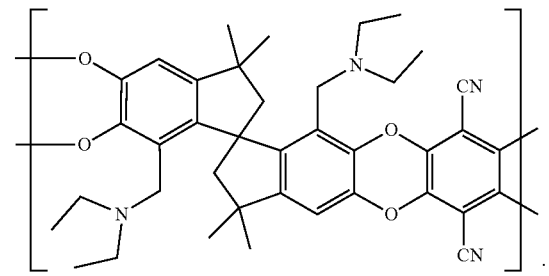

.

24. The microporous polymer of claim 1, having the structure of:

25. The microporous polymer of claim 1, having the structure of:
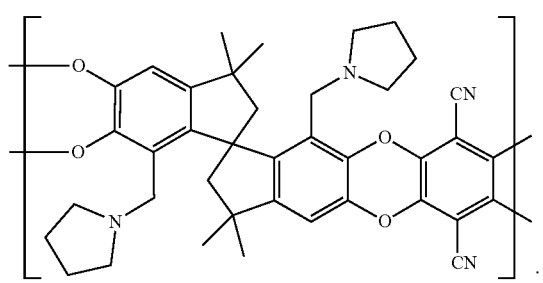
26. The microporous polymer of claim 1, having the structure of:
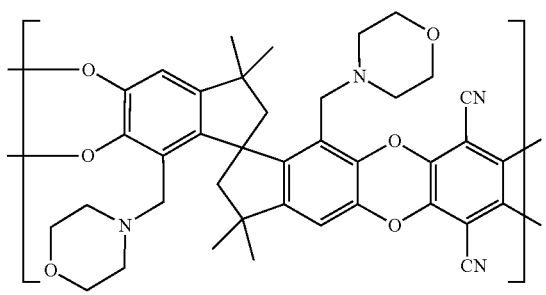
27. The microporous polymer of claim 1, having the structure of:
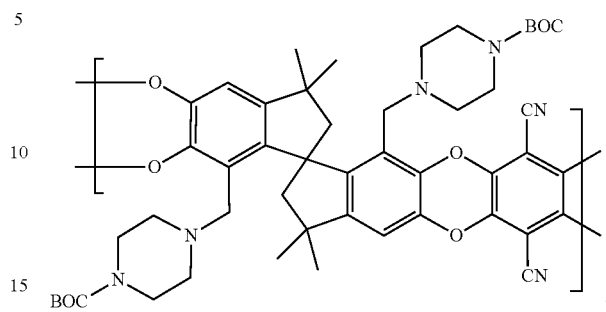
28. The microporous polymer of claim 1, having the structure of:
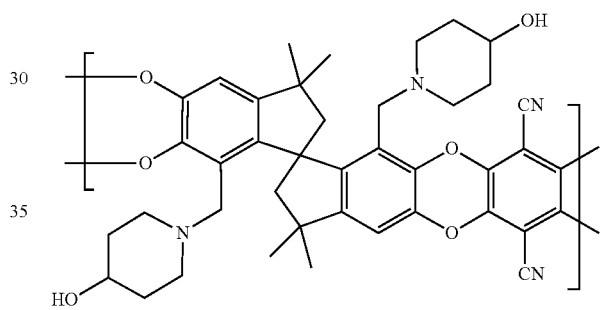
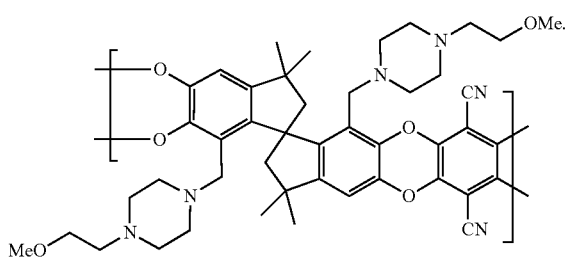
* * * * *